(12) United States Patent
Jain et al.

(10) Patent No.: US 9,173,567 B2
(45) Date of Patent: Nov. 3, 2015

(54) TRIGGERING USER QUERIES BASED ON SENSOR INPUTS

(75) Inventors: Jawahar Jain, Los Altos, CA (US); David Loren Marvit, San Francisco, CA (US); Albert H. M. Reinhardt, Albany, CA (US)

(73) Assignee: Fujitsu Limited, Kawasaki-shi (JP)

( * ) Notice: Subject to any disclaimer, the term of this patent is extended or adjusted under 35 U.S.C. 154(b) by 409 days.

(21) Appl. No.: 13/107,022

(22) Filed: May 13, 2011

(65) Prior Publication Data
US 2012/0289788 A1   Nov. 15, 2012

(51) Int. Cl.
*A61B 5/00* (2006.01)
*G06F 19/00* (2011.01)
*A61B 5/16* (2006.01)

(52) U.S. Cl.
CPC .............. *A61B 5/0022* (2013.01); *A61B 5/165* (2013.01); *G06F 19/3418* (2013.01); *A61B 5/7232* (2013.01); *A61B 2560/0242* (2013.01)

(58) Field of Classification Search
CPC .............. A61B 5/165; A61B 5/02438; A61B 5/02055; A61B 5/02416; A61B 5/486; A61B 5/7232; A61B 5/0022; A61B 2560/0242; G06F 19/00; G06F 19/3418; G06F 19/3431; G06F 19/345; G06F 3/015
See application file for complete search history.

(56) References Cited

U.S. PATENT DOCUMENTS

| | | | | |
|---|---|---|---|---|
| 6,001,065 | A * | 12/1999 | DeVito | 600/544 |
| 6,607,484 | B2 * | 8/2003 | Suzuki et al. | 600/300 |
| 6,623,427 | B2 * | 9/2003 | Mandigo | 600/300 |
| 7,766,828 | B2 * | 8/2010 | Ishii et al. | 600/300 |
| 7,774,388 | B1 | 8/2010 | Runchey | |
| 7,955,259 | B2 * | 6/2011 | Lee et al. | 600/301 |
| 7,988,630 | B1 * | 8/2011 | Osorio et al. | 600/365 |
| 8,529,447 | B2 * | 9/2013 | Jain et al. | 600/300 |
| 8,540,629 | B2 * | 9/2013 | Jain et al. | 600/300 |
| 8,617,067 | B2 * | 12/2013 | Jain et al. | 600/300 |
| 8,622,899 | B2 * | 1/2014 | Jain et al. | 600/300 |
| 8,622,900 | B2 * | 1/2014 | Jain et al. | 600/300 |
| 8,622,901 | B2 * | 1/2014 | Jain et al. | 600/300 |
| 2001/0049471 | A1 * | 12/2001 | Suzuki et al. | 600/300 |
| 2003/0236451 | A1 | 12/2003 | El-Nokaly | |
| 2004/0236234 | A1 | 11/2004 | Fuchs | |
| 2007/0225614 | A1 * | 9/2007 | Naghavi et al. | 600/549 |
| 2008/0081963 | A1 | 4/2008 | Naghavi | |
| 2008/0195980 | A1 | 8/2008 | Morris | |
| 2008/0208015 | A1 * | 8/2008 | Morris et al. | 600/301 |
| 2008/0214903 | A1 | 9/2008 | Orbach | |
| 2009/0069641 | A1 | 3/2009 | Cho | |
| 2010/0292545 | A1 | 11/2010 | Berka | |

OTHER PUBLICATIONS

U.S. Appl. No. 13/107,615, filed May 13, 2011, Jawahar Jain.
U.S. Appl. No. 13/107,746, filed May 13, 2011, Jawahar Jain.
U.S. Appl. No. 13/107,432, filed May 13, 2011, Jawahar Jain.
U.S. Appl. No. 13/107,644, filed May 13, 2011, Jawahar Jain.

(Continued)

*Primary Examiner* — Gary Jackson
*Assistant Examiner* — Shirley Jian
(74) *Attorney, Agent, or Firm* — Baker Botts L.L.P.

(57) ABSTRACT

In particular embodiments, a method includes accessing one or more physiological data streams, analyzing each physiological data stream in reference to a set of control parameters, and, if a data stream deviates from its control parameters, then transmitting a query to a mood sensor or a behavioral sensor.

68 Claims, 14 Drawing Sheets

(56) References Cited

OTHER PUBLICATIONS

U.S. Appl. No. 13/107,211, filed May 13, 2011, Jawahar Jain.
U.S. Appl. No. 13/107,540, filed May 13, 2011, B. Thomas Adler.
U.S. Appl. No. 13/107,605, filed May 13, 2011, Jawahar Jain.
U.S. Appl. No. 13/107,697, filed May 13, 2011, Jawahar Jain.
Albrecht, P., et al., "Estimation of heart rate power spectrum bands from real-world data," *In Proceedings of computers in cardiology*, 311-314. IEEE, 1988.
"A Sea of Sensors," *The Economist*, www.economist.com/node/17388356, 2010.
Bernardi, L., et al., "Effects of controlled breathing, mental activity and mental stress with or without verbalization on heart rate variability," *Journal of the American College of Cardiology*, 35, 1462-1469, 2000.
Bigger, J. T., et al., "Frequency domain measure of heart period variability and mortality after myocardial infarction," *Circulation*, 85, 164-171, 1992.
Clifford, G. D., "Signal processing methods for heart rate variability," *University of Oxford, thesis submitted to the Department of Engineering Science*, 2002.
Dikecligil, G. N., et al., "Ambulatory and challenge-associated heart rate variability measures predict cardiac responses to real-world acute emotional stress," *Biol. Psychiatry*, 67, 1185-1190, 2010.
Egelund, N., "Spectral analysis of heart rate variability as an indicator of driver fatigue," *Ergonomics*, 25, 663-672, 1982.
Filaire, E., et al., "Effect of lecturing to 200 students on heart rate variability and alpha-amylase activity," *Eur. J. Appl. Physiol.*, 108, 1035-1043, 2010.
Hjortskov, N., et al., "The effect of mental stress on heart rate variability and blood pressure during computer work," *Eur. J. Appl. Physiol.*, 92, 84-89, 2004.
Langelotz, C., et al., "Stress and heart rate variability in surgeons during a 24-hour shift," *Arch Surg*, 143, 751-755, 2008.
Pagani, M., et al., "Power spectral analysis of heart rate and arterial pressure variabilities as a marker of sympathovagal interaction in man and conscious dog," *Circulation Research.*, 59, 178-193, 1986.
Parati, G., et al., "Spectral analysis of blood pressure and heart rate variability in evaluating cardiovascular regulation," *Hypertension*, 25, 1276-1286, 1995.
Rottman, J. N., et al., "Efficient estimation of the heart period power spectrum suitable for physiologic or pharmacologic studies," *American Journal of Cardiology*, 66(20), 1522-1524, 1990.
Russoniello, C. V., et al., "EEG, HRV and psychological correlates while playing Bejeweled II: A randomized controlled study," *Stud Health Technol Inform*, 144, 189-92, 2009.
Salahuddin, L., et al., "Detection of acute stress by heart rate variability using a prototype mobile ECG sensor," *Hybrid Information Technology, International Conference on*, 2, 453-459, 2006.
Vempati, R. P., et al., "Baseline occupational stress levels and physiological responses to a two day stress management program," *Journal of Indian Psychology*, 18(1), 33-37, 2000.
Yang, H. K., et al., "Application for the wearable heart activity monitoring system: analysis of the autonomic function of HRV," *Conf Proc IEEE Eng Med Biol Soc*, 2008, 1258-1261.
"Autonomic nervous system," Wikipedia.com, http://en.wikipedia.org/wiki/Autonomic_nervous_system, 2012.
"Kidney," Wikipedia.com, http://en.wikipedia.org/wiki/kidney, 2012.
Office Action for U.S. Appl. No. 13/107,615, Aug. 10, 2012.
Office Action for U.S. Appl. No. 13/107,746, Aug. 13, 2012.
Office Action for U.S. Appl. No. 13/107,432, Aug. 6, 2012.
Office Action for U.S. Appl. No. 13/107,697, Aug. 6, 2012.
Office Action for U.S. Appl. No. 13/107,211, Aug. 10, 2012.
Office Action for U.S. Appl. No. 13/107,022, Jul. 23, 2012.
Office Action for U.S. Appl. No. 13/107,644, Aug. 10, 2012.
Non-Final Office Action for U.S. Appl. No. 13/107,746, Apr. 1, 2013.
Final Office Action for U.S. Appl. No. 13/107,022, Feb. 8, 2013.
Final Office Action for U.S. Appl. No. 13/107,697, Jan. 17, 2013.
Office Action for U.S. Appl. No. 13/107,432, May 9, 2013.
Office Action for U.S. Appl. No. 13/107,644, May 9, 2013.
Office Action for U.S. Appl. No. 13/107,211, May 9, 2013.
Office Action for U.S. Appl. No. 13/107,605, May 9, 2013.
Office Action for U.S. Appl. No. 13/107,615, Dec. 21, 2012.
Office Action for U.S. Appl. No. 13/107,746, Dec. 7, 2012.
Office Action for U.S. Appl. No. 13/107,432, Dec. 6, 2012.
Office Action for U.S. Appl. No. 13/107,644, Dec. 19, 2012.
Office Action for U.S. Appl. No. 13/107,211, Dec. 19, 2012.
Office Action for U.S. Appl. No. 13/107,605, Dec. 7, 2012.
Office Action for U.S. Appl. No. 13/107,697, Jan. 17, 2013.

\* cited by examiner

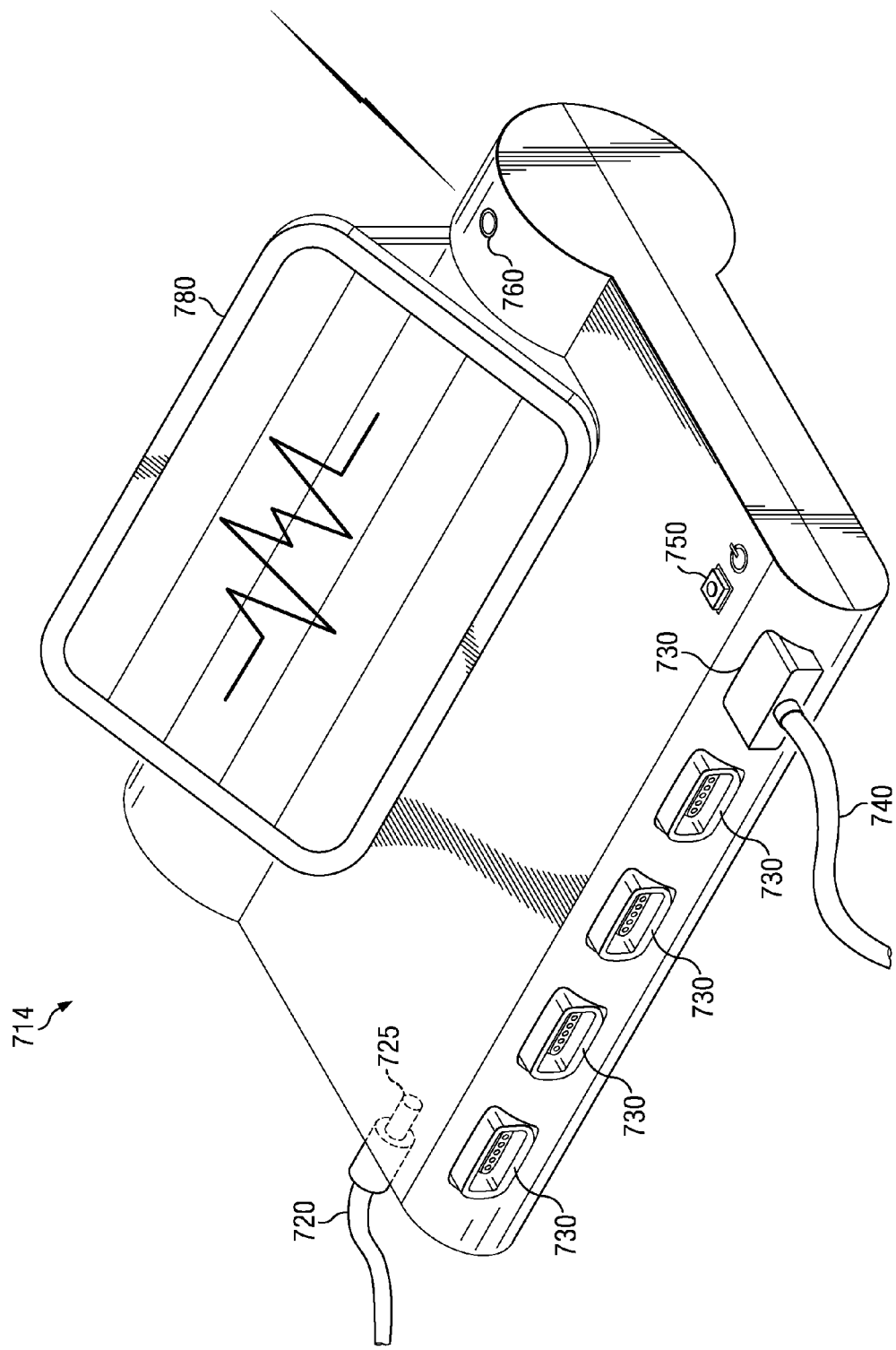

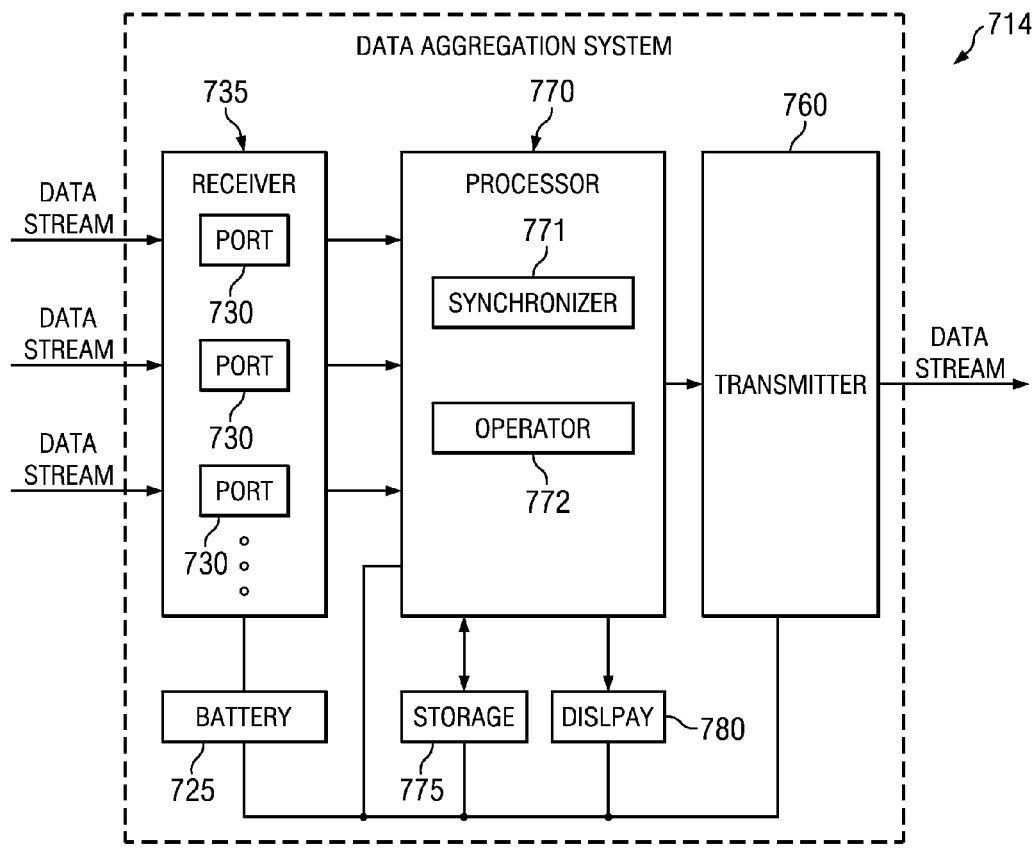

810 — ACCESSING AN ORIGINAL DATA STREAM FROM EACH OF ONE OR MORE SENSORS, EACH OF THE ORIGINAL DATA STREAMS COMPRISING A SERIES OF SAMPLES THAT EACH REPRESENT A MEASUREMENT OF A STIMULUS SENSED BY THE SENSOR THAT THE ORIGINAL DATA STREAM IS FROM, ONE OR MORE OF THE SENSORS BEING AFFIXED TO THE PERSON'S BODY

820 — ASSOCIATING A SYSTEM TIMESTAMP WITH EACH OF THE SAMPLES BASED ON A SYSTEM CLOCK, THE SYSTEM CLOCK OPERATING INDEPENDENT OF THE PLURALITY OF SENSORS

830 — RECORDING THE ORIGINAL DATA STREAMS WITH THE SYSTEM TIMESTAMPS ASSOCIATED WITH THEIR SAMPLES FOR CORRELATION OF THE ORIGINAL DATA STREAMS WITH EACH OTHER OR WITH INFORMATION OUTSIDE THE DATA STREAMS

┌─────────────────────────────────────────────────────────┐
│ ACCESSING ONE OR MORE DATA STREAMS FROM A PLURALITY OF │
│ SENSORS, THE SENSORS COMPRISING A RENAL DOPPLER SONOGRAPH │
│ AND ONE OR MORE OF A HEART-RATE MONITOR, A BLOOD-PRESSURE │
│ MONITOR, A PULSE OXIMETER, OR A MOOD SENSOR, THE DATA │ — 910
│ STREAMS COMPRISING RENAL-DOPPLER DATA OF A PERSON FROM THE │
│ RENAL DOPPLER SONOGRAPH AND ONE OR MORE OF HEART-RATE │
│ DATA OF THE PERSON FROM THE HEART-RATE MONITOR, │
│ BLOOD-PRESSURE DATA OF THE PERSON FROM THE BLOOD-PRESSURE │
│ MONITOR, PULSE-OXIMETRY DATA OF THE PERSON FROM THE PULSE │
│ OXIMETER, OR MOOD DATA OF THE PERSON FROM THE MOOD SENSOR │
└─────────────────────────────────────────────────────────┘
                              ↓
        ┌──────────────────────────────────────┐
        │ GENERATING A STRESS MODEL OF THE     │ — 920
        │ PERSON BASED ON THE DATA STREAMS     │
        └──────────────────────────────────────┘

1010 — ACCESSING ONE OR MORE DATA STREAMS FROM A PLURALITY OF SENSORS, THE SENSORS COMPRISING ONE OR MORE OF A HEART-RATE MONITOR, A BLOOD-PRESSURE MONITOR, A PULSE OXIMETER, A MOOD SENSOR, OR AN ACCELEROMETER, THE DATA STREAMS COMPRISING ONE OR MORE OF HEART-RATE DATA OF A PERSON FROM THE HEART-RATE MONITOR, BLOOD-PRESSURE DATA OF THE PERSON FROM THE BLOOD-PRESSURE MONITOR, PULSE OXIMETRY DATA OF THE PERSON FROM THE PULSE OXIMETER, MOOD DATA OF THE PERSON FROM THE MOOD SENSOR, OR ACCELEROMETER DATA OF THE PERSON FROM THE ACCELEROMETER

1020 — ACCESSING A STRESS MODEL, THE STRESS MODEL COMPRISING BASELINE RENAL-DOPPLER DATA AND TWO OR MORE OF BASELINE HEART-RATE DATA, BASELINE BLOOD-PRESSURE DATA, BASELINE PULSE OXIMETRY DATA, OR BASELINE MOOD DATA

1030 — ANALYZING THE DATA STREAMS WITH RESPECT TO THE STRESS MODEL

1040 — DETERMINING BASED ON THE ANALYSIS A CURRENT STRESS INDEX OF THE PERSON

| ACCESSING ONE OR MORE DATA STREAMS FROM A PLURALITY OF SENSORS, THE SENSORS COMPRISING A MOOD SENSOR AND ONE OR MORE OF A HEART-RATE MONITOR, A BLOOD-PRESSURE MONITOR, A PULSE OXIMETER, OR AN ACCELEROMETER, WHEREIN:   THE DATA STREAMS COMPRISE MOOD DATA OF A PERSON FROM THE MOOD SENSOR AND ONE OR MORE OF HEART-RATE DATA OF THE PERSON FROM THE HEART-RATE MONITOR, BLOOD-PRESSURE DATA OF THE PERSON FROM THE BLOOD-RESSURE MONITOR, PULSE-OXIMETRY DATA OF THE PERSON FROM THE PULSE OXIMETER, OR ACCELEROMETER DATA OF THE PERSON FROM THE ACCELEROMETER;   A FIRST DATA SET FROM THE DATA STREAMS WAS COLLECTED FROM THE PERSON AT A FIRST TIME, THE PERSON BEING SUBSTANTIALLY STRESSED AT THE FIRST TIME; AND   A SECOND DATA SET FROM THE DATA STREAMS WAS COLLECTED FROM THE PERSON AT A SECOND TIME, THE PERSON BEING SUBSTANTIALLY UNSTRESSED AT THE SECOND TIME | 1110 |

↓

| ANALYZING THE FIRST DATA SET AND SECOND DATA SET WITH RESPECT TO EACH OTHER | 1120 |

↓

| DETERMINING A CURRENT STRESS INDEX OF THE PERSON BASED ON THE ANALYSIS OF THE FIRST DATA SET AND SECOND DATA SET WITH RESPECT TO EACH OTHER | 1130 |

| |
|---|
| ACCESSING ONE OR MORE DATA STREAMS FROM A PLURALITY OF SENSORS, THE SENSORS COMPRISING AN ACCELEROMETER AND ONE OR MORE OF A HEART-RATE MONITOR, A BLOOD-PRESSURE MONITOR, A PULSE OXIMETER, OR A MOOD SENSOR, WHEREIN: <br><br> THE DATA STREAMS COMPRISE ACCELEROMETER DATA OF A PERSON FROM THE ACCELEROMETER AND ONE OR MORE OF HEART-RATE DATA OF THE PERSON FROM THE HEART RATE MONITOR, BLOOD-PRESSURE DATA OF THE PERSON FROM THE BLOOD-PRESSURE MONITOR, PULSE-OXIMETRY DATA OF THE PERSON FROM THE PULSE OXIMETER, AND MOOD DATA OF THE PERSON FROM THE MOOD SENSOR; <br><br> A FIRST DATA SET FROM THE DATA STREAMS WAS COLLECTED FROM THE PERSON AT A FIRST TIME, THE PERSON BEING ENGAGED IN A FIRST ACTIVITY AT THE FIRST TIME; AND <br><br> A SECOND DATA SET FROM THE DATA STREAMS WAS COLLECTED FROM THE PERSON AT A SECOND TIME, THE PERSON BEING ENGAGED IN A SECOND ACTIVITY AT THE SECOND TIME — 1210 |
| ANALYZING THE FIRST DATA SET AND SECOND DATA SET WITH RESPECT TO EACH OTHER — 1220 |
| DETERMINING A CURRENT STRESS INDEX OF THE PERSON BASED ON THE ANALYSIS OF THE FIRST DATA SET AND SECOND DATA SET WITH RESPECT TO EACH OTHER — 1230 |

ACCESSING ONE OR MORE DATA STREAMS FROM A PLURALITY OF SENSORS, THE SENSORS COMPRISING AN ENVIRONMENTAL SENSOR AND ONE OR MORE OF A MOOD SENSOR, A HEART-RATE MONITOR, A BLOOD-PRESSURE MONITOR, A PULSE OXIMETER, OR AN ACCELEROMETER, WHEREIN:
    THE DATA STREAMS COMPRISE ENVIRONMENTAL DATA FROM THE ENVIRONMENTAL SENSOR AND ONE OR MORE OF MOOD DATA OF A PERSON FROM THE MOOD SENSOR, HEART-RATE DATA OF THE PERSON FROM THE HEART-RATE MONITOR, BLOOD-PRESSURE DATA OF THE PERSON FROM THE BLOOD-PRESSURE MONITOR, PULSE-OXIMETRY DATA OF THE PERSON FROM THE PULSE OXIMETER, AND ACCELEROMETER DATA OF THE PERSON FROM THE ACCELEROMETER;
    A FIRST DATA SET FROM THE DATA STREAMS WAS COLLECTED FROM THE PERSON AT A FIRST TIME, THE ENVIRONMENTAL DATA IN THE FIRST DATA SET INDICATING A FIRST STATE AT THE FIRST TIME; AND
    A SECOND DATA SET FROM THE DATA STREAMS WAS COLLECTED FROM THE PERSON AT A SECOND TIME, THE ENVIRONMENTAL DATA IN THE SECOND DATA SET INDICATING A SECOND STATE AT THE SECOND TIME
    —1310

ANALYZING THE FIRST DATA SET AND SECOND DATA SET WITH RESPECT TO EACH OTHER —1320

DETERMINING A CURRENT STRESS INDEX OF THE PERSON BASED ON THE ANALYSIS OF THE FIRST DATA SET AND SECOND DATA SET WITH RESPECT TO EACH OTHER —1330

```
┌─────────────────────────────────────────────────────────────────┐
│ ACCESSING ONE OR MORE DATA STREAMS FROM A PLURALITY OF SENSORS, │
│ WHEREIN:                                                         │
│     THE SENSORS COMPRISE:                                        │
│         ONE OR MORE FIRST SENSORS SELECTED FROM A FIRST          │
│         GROUP OF SENSOR TYPES CONSISTING OF A HEART-RATE MONITOR,│
│         A BLOOD-PRESSURE MONITOR, A PULSE OXIMETER, AND AN       │
│         ACCELEROMETER;                                           │
│         ONE OR TWO SECOND SENSORS SELECTED FROM A SECOND         │
│         GROUP OF SENSOR TYPES CONSISTING OF A MOOD SENSOR, A     │
│         BEHAVIORAL SENSOR, AND AN ENVIRONMENTAL SENSOR;          │
│         ONE THIRD SENSOR ALSO SELECTED FROM THE SECOND           │
│         GROUP OF SENSOR TYPES, THE THIRD SENSOR BEING DIFFERENT IN│
│         SENSOR TYPE FROM EACH OF THE TWO SECOND SENSORS;         │
│     THE DATA STREAMS COMPRISE ONE OR MORE OF HEART-RATE DATA OF A│──1410
│ PERSON FROM THE HEART-RATE MONITOR, BLOOD-PRESSURE DATA OF THE   │
│ PERSON FROM THE BLOOD-PRESSURE MONITOR, PULSE-OXIMETRY DATA OF THE│
│ PERSON FROM THE PULSE OXIMETER, ACCELEROMETER DATA OF THE PERSON │
│ FROM THE ACCELEROMETER, MOOD DATA OF THE PERSON FROM THE MOOD    │
│ SENSOR, BEHAVIORAL DATA OF THE PERSON FROM THE BEHAVIORAL SENSOR, OR│
│ ENVIRONMENTAL DATA FROM THE ENVIRONMENTAL SENSOR;                │
│     A FIRST DATA SET FROM THE DATA STREAMS WAS COLLECTED FROM THE│
│ PERSON AT A FIRST TIME, THE PERSON HAVING BEEN EXPOSED TO A STRESSOR│
│ AT THE FIRST TIME, AS INDICATED BY DATA IN THE FIRST DATA SET FROM THE│
│ THIRD SENSOR; AND                                                │
│     A SECOND DATA SET FROM THE DATA STREAMS WAS COLLECTED FROM   │
│ THE PERSON AT A SECOND TIME, THE PERSON NOT HAVING BEEN EXPOSED TO│
│ THE STRESSOR AT THE SECOND TIME, AS INDICATED BY DATA IN THE SECOND│
│ DATA SET FROM THE THIRD SENSOR                                   │
└─────────────────────────────────────────────────────────────────┘
                                 ↓
┌─────────────────────────────────────────────────────────────────┐
│           ANALYZING THE FIRST DATA SET AND SECOND                │──1420
│           DATA SET WITH RESPECT TO EACH OTHER                    │
└─────────────────────────────────────────────────────────────────┘
                                 ↓
┌─────────────────────────────────────────────────────────────────┐
│       DETERMINING A CURRENT STRESS FACTOR FOR THE STRESSOR WITH  │
│       RESPECT TO THE PERSON BASED ON THE ANALYSIS OF THE FIRST   │──1430
│       DATA SET AND SECOND DATA SET WITH RESPECT TO EACH OTHER    │
└─────────────────────────────────────────────────────────────────┘
```

ACCESSING ONE OR MORE DATA STREAMS FROM A PLURALITY OF SENSORS, THE SENSORS COMPRISING TWO OR MORE OF AN ACCELEROMETER, A HEART-RATE MONITOR, A BLOOD-PRESSURE MONITOR, A PULSE OXIMETER, OR A MOOD SENSOR, WHEREIN:
    THE DATA STREAMS COMPRISE TWO OR MORE OF ACCELEROMETER DATA OF A PERSON FROM THE ACCELEROMETER, HEART-RATE DATA OF THE PERSON FROM THE HEART RATE MONITOR, BLOOD-PRESSURE DATA OF THE PERSON FROM THE BLOOD-PRESSURE MONITOR, PULSE-OXIMETRY DATA OF THE PERSON FROM THE PULSE OXIMETER, OR MOOD DATA OF THE PERSON FROM THE MOOD SENSOR;
    A FIRST DATA SET FROM THE DATA STREAMS WAS COLLECTED FROM THE PERSON AT A FIRST TIME, THE PERSON HAVING ENGAGED IN A THERAPY AT THE FIRST TIME; AND
    A SECOND DATA SET FROM THE DATA STREAMS WAS COLLECTED FROM THE PERSON AT A SECOND TIME, THE PERSON NOT HAVING ENGAGED IN THE THERAPY AT THE SECOND TIME ⟶1510

ANALYZING THE FIRST DATA SET AND SECOND DATA SET WITH RESPECT TO EACH OTHER ⟶1520

DETERMINING A CURRENT STRESS FACTOR FOR THE THERAPY ON THE PERSON BASED ON THE ANALYSIS OF THE FIRST DATA SET AND SECOND DATA SET WITH RESPECT TO EACH OTHER ⟶1530

*FIG. 15*

TRIGGERING USER QUERIES BASED ON SENSOR INPUTS

TECHNICAL FIELD

This disclosure generally relates to sensors and sensor networks for monitoring and analyzing a person's health.

BACKGROUND

A sensor network may include distributed autonomous sensors. Uses of sensor networks include but are not limited to military applications, industrial process monitoring and control, machine health monitoring, environment and habitat monitoring, utility usage, healthcare and medical applications, home automation, and traffic control. A sensor in a sensor network is typically equipped with a communications interface, a controller, and an energy source (such as a battery).

A sensor typically measures a physical quantity and converts it into a signal that an observer or an instrument can read. For example, a mercury-in-glass thermometer converts a measured temperature into expansion and contraction of a liquid that can be read on a calibrated glass tube. A thermocouple converts temperature to an output voltage that a voltmeter can read. For accuracy, sensors are generally calibrated against known standards.

Detecting and managing stress is a significant problem in modern-day medicine. If fact, many doctors argue that stress and stress-related symptoms are a major cause of death. Consequently, methods and systems for modeling, measuring, and monitoring stress in a person provide significant health benefits.

BRIEF DESCRIPTION OF THE DRAWINGS

FIG. 7A illustrates an example of a data aggregation system.

FIG. 7B illustrates an example of a data aggregation system.

FIG. 8 illustrates an example method for aggregating data streams from sensors.

FIG. 9 illustrates an example method for creating a stress profile using renal Doppler sonography.

FIG. 10 illustrates an example method for monitoring stress using a stress profile created by renal Doppler sonography.

FIG. 11 illustrates an example method for monitoring stress using psychological or behavioral data.

FIG. 12 illustrates an example method for monitoring stress using accelerometer data.

FIG. 13 illustrates an example method for monitoring stress using environmental data.

FIG. 14 illustrates an example method for calculating a stress factor for a stressor.

FIG. 15 illustrates an example method for calculating a stress factor for a therapy.

DESCRIPTION OF EXAMPLE EMBODIMENTS

Sensor Networks

Figure 1:
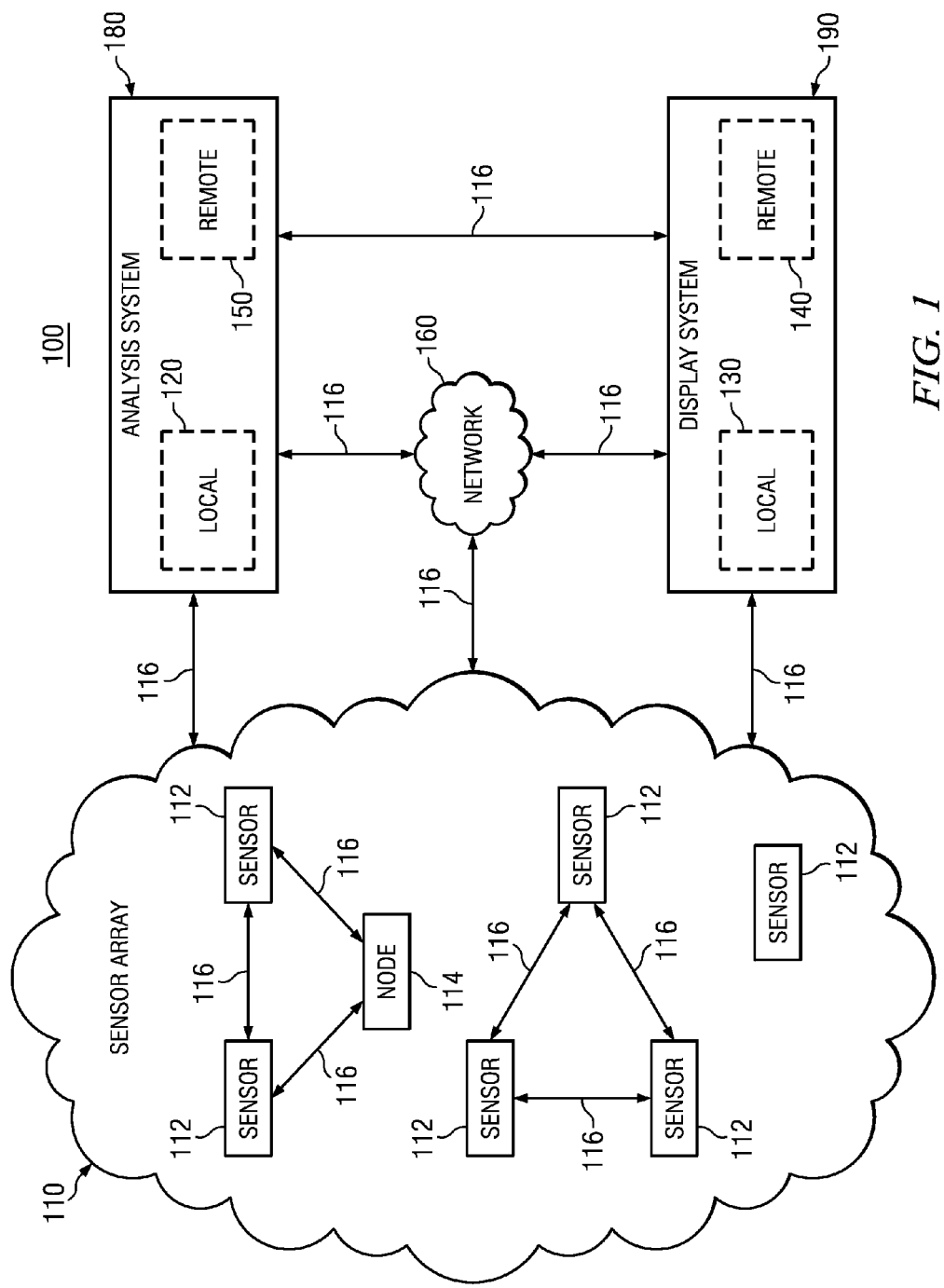
FIG. 1 illustrates an example sensor network.

FIG. 1 illustrates an example sensor network 100. Sensor network 100 comprises a sensor array 110, an analysis system 180, and display system 190. Sensor network 100 enables the collecting, processing, analyzing, sharing, visualizing, displaying, archiving, and searching of sensor data. The data collected by sensors 112 in sensor array 110 may be processed, analyzed, and stored using the computational and data storage resources of sensor network 100. This may be done with both centralized and distributed computational and storage resources. Sensor network 100 may integrate heterogeneous sensor, data, and computational resources deployed over a wide area. Sensor network 100 may be used to undertake a variety of tasks, such as physiological, psychological, behavioral, and environmental monitoring and analysis.

A sensor array 110 comprises one or more sensors 112. A sensor 112 receives a stimulus and converts it into a data stream. The sensors 112 in sensor array 110 may be of the same type (e.g., multiple thermometers) or various types (e.g., a thermometer, a barometer, and an altimeter). A sensor array 110 may transmit one or more data streams based on the one or more stimuli to one or more analysis systems 180 over any suitable network. In particular embodiments, a sensor 112's embedded processors may perform certain computational activities (e.g., image and signal processing) that could also be performed by other components of sensor network 100, such as, for example, analysis system 180 or display system 190.

As used herein, a sensor 112 in a sensor array 110 is described with respect to a subject. Therefore, a sensor 112 may be personal or remote with respect to the subject. Personal sensors receive stimuli that are from or related to the subject. Personal sensors may include, for example, sensors that are affixed to or carried by the subject (e.g., a heart-rate monitor, an input by the subject into a smart phone), sensors that are proximate to the subject (e.g., a thermometer in the room where the subject is located), or sensors that are otherwise related to the subject (e.g., GPS position of the subject, a medical report by the subject's doctor, a subject's email inbox). Remote sensors receive stimulus that is external to or not directly related to the subject. Remote sensors may include, for example, environmental sensors (e.g., weather balloons, stock market ticker), network data feeds (e.g., news feeds), or sensors that are otherwise related to external information. A sensor 112 may be both personal and remote depending on the circumstances. As an example and not by way of limitation, if the subject is a particular person, a thermometer in a subject's home may be considered personal while the subject is at home, but remote when the subject is away from home. As another example and not by way of limitation, if the subject is a particular home, a thermometer in the home may be considered personal to the home regardless of whether a person is in the home or away.

The sensor array 110 may further comprise one or more data aggregation nodes 114. A node 114 may access one or more data streams from one or more sensors 112 in the sensor array 110. The node 114 may then monitor, store, and analyze one or more data streams from the sensors 112. In particular embodiments, the node 114 may synchronize a plurality of data streams from a plurality of sensors 112. A node 114 may transmit one or more data streams based on the one or more data streams received from the sensors 112 to one or more analysis systems 180 over any suitable network. In particular embodiments, a node 114's embedded processors may perform certain computational activities (e.g., image and signal processing) that could also be performed by other components of sensor network 100, such as, for example, analysis system 180 or display system 190. In particular embodiments, a node 114 may analyze one or more data streams from one or more sensors 112 and generate one or more derivative data streams that may be synchronized, modified, stored, transmitted, and analyzed.

Analysis system 180 may monitor, store, and analyze one or more data streams from sensor array 110. Analysis system 180 may have subcomponents that are local 120, remote 150, or both. Display system 190 may render, visualize, display, message, and publish to one or more users based on the output of analysis system 180. Display system 190 may have subcomponents that are local 130, remote 140, or both.

As used herein, the analysis and display components of sensor network 100 are described with respect to a sensor 112. Therefore, a component may be local or remote with respect to the sensor 112. Local components (i.e., local analysis system 120, local display system 130) may include components that are built into or proximate to the sensor 112. As an example and not by way of limitation, a sensor 112 could include an integrated computing system and LCD monitor that function as local analysis system 120 and local display system 130. Remote components (i.e., remote analysis system 150, remote display system 190) may include components that are external to or independent of the sensor 112. As another example and not by way of limitation, a sensor 112 could transmit a data stream over a network to a remote server at a medical facility, wherein dedicated computing systems and monitors function as remote analysis system 150 and remote display system 190. In particular embodiments, each sensor 112 in sensor array 110 may utilize either local or remote display and analysis components, or both. In particular embodiments, a user may selectively access, analyze, and display the data streams from one or more sensors 112 in sensor array 110. This may be done, for example, as part of running a specific application or data analysis algorithm. The user could access data from specific types of sensors 112 (e.g., all thermocouple data), from sensors 112 that measure specific types of data (e.g., all environmental sensors), or based on other criteria.

Although FIG. 1 illustrates a particular arrangement of sensor array 110, sensors 112, node 114, analysis system 180, local analysis system 120, remote analysis system 150, display system 190, local display system 130, remote display system 140, and network 160, this disclosure contemplates any suitable arrangement of sensor array 110, sensors 112, node 114, analysis system 180, local analysis system 120, remote analysis system 150, display system 190, local display system 130, remote display system 140, and network 160. As an example and not by way of limitation, two or more of sensor array 110, sensors 112, nodes 114, analysis system 180, local analysis system 120, remote analysis system 150, display system 190, local display system 130, and remote display system 140 may be connected to each other directly, bypassing network 160. As another example, one or more sensors 112 may be connected directly to communication network 160, without being part of a sensor array 110. As another example, two or more of sensor array 110, sensors 112, node 114, analysis system 180, local analysis system 120, remote analysis system 150, display system 190, local display system 130, and remote display system 140 may be physically or logically co-located with each other in whole or in part. Moreover, although FIG. 1 illustrates a particular number of sensor arrays 110, sensors 112, nodes 114, analysis systems 180, local analysis systems 120, remote analysis systems 150, display systems 190, local display systems 130, remote display systems 140, and networks 160, this disclosure contemplates any suitable number of sensor arrays 110, sensors 112, nodes 114, analysis systems 180, local analysis systems 120, remote analysis systems 150, display systems 190, local display systems 130, remote display systems 140, and networks 160. As an example and not by way of limitation, sensor network 100 may include multiple sensor arrays 110, sensors 112, nodes 114, analysis systems 180, local analysis systems 120, remote analysis systems 150, display systems 190, local display systems 130, remote display systems 140, and networks 160.

This disclosure contemplates any suitable network 160. As an example and not by way of limitation, one or more portions of network 160 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 160 may include one or more networks 160. Similarly, this disclosure contemplates any suitable sensor array 110. As an example and not by way of limitation, one or more portions of sensor array 110 may include an ad hoc network, an intranet, an extranet, a VPN, a LAN, a WLAN, a WAN, a WWAN, a MAN, a portion of the Internet, a portion of the PSTN, a cellular telephone network, or a combination of two or more of these. Sensor array 110 may include one or more sensor arrays 110.

Connections 116 may connect sensor array 110, sensors 112, node 114, analysis system 180, local analysis system 120, remote analysis system 150, display system 190, local display system 130, and remote display system 140 to network 160 or to each other. Similarly, connections 116 may connect sensors 112 to each other or to node 114 in sensor array 110 (or to other equipment in sensor array 110) or to network 160. This disclosure contemplates any suitable connections 116. In particular embodiments, one or more connections 116 include one or more wireline (such as, for example, Digital Subscriber Line (DSL) or Data Over Cable Service Interface Specification (DOCSIS)), wireless (such as, for example, Wi-Fi or Worldwide Interoperability for Microwave Access (WiMAX)) or optical (such as, for example, Synchronous Optical Network (SONET) or Synchronous Digital Hierarchy (SDH)) connections. In particular embodiments, one or more connections 116 each include an ad hoc network, an intranet, an extranet, a VPN, a LAN, a WLAN, a WAN, a WWAN, a MAN, a portion of the Internet, a portion of the PSTN, a cellular telephone network, another connection 116, or a combination of two or more such connections 116. Connections 116 need not necessarily be the same throughout sensor network 100. One or more first connections 116 may differ in one or more respects from one or more second connections 116.

Figure 2A:
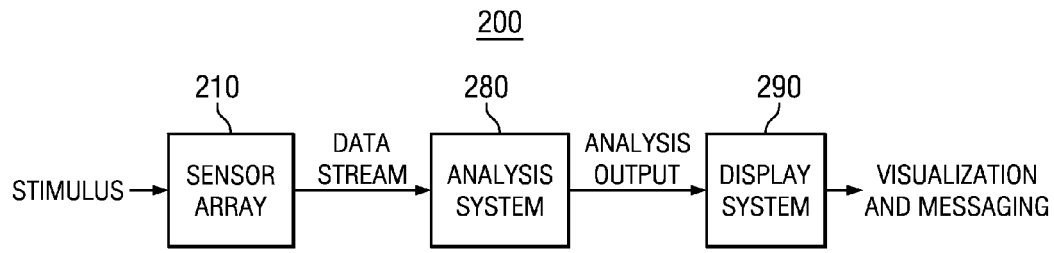
FIG. 2A illustrates an example data flow in a sensor network.

FIG. 2A illustrates an example data flow in a sensor network. In various embodiments, one or more sensors in a sensor array 210 may receive one or more stimuli. The sensor array 210 may transmit one or more data streams based on the one or more stimuli to one or more analysis systems 280 over any suitable network. As an example and not by way of limitation, one sensor could transmit multiple data streams to multiple analysis systems. As another example and not by way of limitation, multiple sensors could transmit multiple data streams to one analysis system.

In particular embodiments, the sensors in sensor array 210 each produce their own data stream, which is transmitted to analysis system 280. In other embodiments, one or more sensors in sensor array 210 each produce their own data stream, which is transmitted to a node. In yet other embodiments, one or more sensors in sensor array 210 have their output combined into a single data stream.

Analysis system 280 may monitor, store, and analyze one or more data streams. Analysis system 280 may be local, remote, or both. Analysis system 280 may transmit one or more analysis outputs based on the one or more data streams to one or more display systems 290. As an example and not by way of limitation, one analysis system could transmit multiple analysis outputs to multiple display systems. As another example and not by way of limitation, multiple analysis systems could transmit multiple analysis outputs to one display system. Analysis system 280 may also store one or more analysis outputs for later processing.

A display system 290 may render, visualize, display, message, and publish to one or more users based on the one or more analysis outputs. A display system 290 may be local, remote, or both. In various embodiments, a sensor array 210 may transmit one or more data streams directly to a display system 290. This may allow, for example, display of stimulus readings by the sensor.

Although FIG. 2A illustrates a particular arrangement of sensor array 210, analysis system 280, and display system 290, this disclosure contemplates any suitable arrangement of sensor array 210, analysis system 280, and display system 290. Moreover, although FIG. 2A illustrates a particular data flow between sensor array 210, analysis system 280, and display system 290, this disclosure contemplates any suitable data flow between sensor array 210, analysis system 280, and display system 290.

Sensors

Figure 2B:
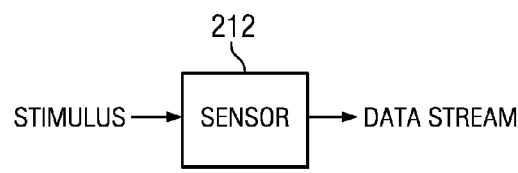
FIG. 2B illustrates an example sensor.

FIG. 2B illustrates an example sensor 212 and data flow to and from the sensor. A sensor 212 is a device which receives and responds to a stimulus. Here, the term "stimulus" means any signal, property, measurement, or quantity that may be detected and measured by a sensor 212.

In particular embodiments, a sensor 212 receives stimuli from a subject. As an example and not by way of limitation, a subject may be a person (or group of persons or entity), place (such as, for example, a geographical location), or thing (such as, for example, a building, road, or car). Although this disclosure describes particular types of subjects, this disclosure contemplates any suitable types of subjects. In particular embodiments, one or more subjects of one or more sensors 112 may be a user of other components of sensor network 100, such as other sensors 112, analysis system 180, or display system 190. As such, the terms "subject" and "user" may refer to the same person, unless context suggests otherwise.

A sensor 212 responds to a stimulus by generating a data stream corresponding to the stimulus. A data stream may be a digital or analog signal that can be transmitted over any suitable transmission medium and further used in electronic devices. As used herein, the term "sensor" is used broadly to describe any device that receives a stimulus and converts it into a data stream. The present disclosure assumes that the data stream output from a sensor 212 is transmitted to an analysis system, unless otherwise specified.

In particular embodiments, one or more sensors 212 each include a stimulus receiving element (i.e., sensing element), a communication element, and any associate circuitry. Sensors 212 generally are small, battery powered, portable, and equipped with a microprocessor, internal memory for data storage, and a transducer or other component for receiving stimulus. However, a sensor 212 may also be an assay, test, or measurement. A sensor 212 may interface with a personal computer and utilize software to activate the sensor 212 and to view and analyze the collected data. A sensor 212 may also have a local interface device (e.g., keypad, LCD) allowing it to be used as a stand-alone device. In particular embodiments, a sensor 212 may include one or more communication elements that may receive or transmit information (such as data streams) over a communication channel, for example to one or more other components in a sensor network.

In particular embodiments, one or more sensors 212 may measure a variety of things, including physiological, psychological, behavioral, and environmental stimulus. Physiological stimulus may include, for example, physical aspects of a person (e.g., stretch, motion of the person, and position of appendages); metabolic aspects of a person (e.g., glucose level, oxygen level, osmolality), biochemical aspects of a person (e.g., enzymes, hormones, neurotransmitters, cytokines), and other aspects of a person related to physical health, disease, and homeostasis. Psychological stimulus may include, for example, emotion, mood, feeling, anxiety, stress, depression, and other psychological or mental states of a person. Behavioral stimulus may include, for example, behavior related a person (e.g., working, socializing, arguing, drinking, resting, driving), behavior related to a group (e.g., marches, protests, mob behavior), and other aspects related to behavior. Environmental stimulus may include, for example, physical aspects of the environment (e.g., light, motion, temperature, magnetic fields, gravity, humidity, vibration, pressure, electrical fields, sound, GPS location), environmental molecules (e.g., toxins, nutrients, pheromones), environmental conditions (e.g., pollen count, weather), other external condition (e.g., traffic conditions, stock market information, news feeds), and other aspects of the environment.

As an example and not by way of limitation, particular embodiments may include one or more of the following types of sensors: Accelerometer; Affinity electrophoresis; Air flow meter; Air speed indicator; Alarm sensor; Altimeter; Ammeter; Anemometer; Arterial blood gas sensor; Attitude indicator; Barograph; Barometer; Biosensor; Bolometer; Boost gauge; Bourdon gauge; Breathalyzer; Calorie Intake Monitor; calorimeter; Capacitive displacement sensor; Capillary electrophoresis; Carbon dioxide sensor; Carbon monoxide detector; Catalytic bead sensor; Charge-coupled device; Chemical field-effect transistor; Chromatograph; Colorimeter; Compass; Contact image sensor; Current sensor; Depth gauge; DNA microarray; Electrocardiograph (ECG or EKG); Electrochemical gas sensor; Electrolyte-insulator-semiconductor sensor; Electromyograph (EMG); Electronic nose; Electro-optical sensor; Exhaust gas temperature gauge; Fiber optic sensors; Flame detector; Flow sensor; Fluxgate compass; Foot switches; Force sensor; Free fall sensor; Galvanic skin response sensor; Galvanometer; Gardon gauge; Gas detector; Gas meter; Geiger counter; Geophone; Goniometers; Gravimeter; Gyroscope; Hall effect sensor; Hall probe; Heart-rate sensor; Heat flux sensor; High-performance liquid chromatograph (HPLC); Hot filament ionization gauge; Hydrogen sensor; Hydrogen sulfide sensor; Hydrophone; Immunoassay, Inclinometer; Inertial reference unit; Infrared point sensor; Infra-red sensor; Infrared thermometer; Insulin monitors; Ionization gauge; Ion-selective electrode; Keyboard; Kinesthetic sensors; Laser rangefinder; Leaf electroscope; LED light sensor; Linear encoder; Linear variable differential transformer (LVDT); Liquid capacitive inclinometers; Magnetic anomaly detector; Magnetic compass; Magnetometer; Mass flow sensor; McLeod gauge; Metal detector; MHD sensor; Microbolometer; Microphone; Microwave chemistry sensor; Microwave radiometer; Mood sensor; Motion detector; Mouse; Multimeter; Net radiometer; Neutron detection; Nichols radiometer; Nitrogen oxide sensor; Nondispersive infrared sensor; Occupancy sensor; Odometer; Ohmmeter; Olfactometer; Optode; Oscillating U-tube; Oxygen sensor; Pain sensor; Particle detector; Passive infrared sensor; Pedometer; Pellistor; pH glass electrode; Photoplethysmograph; Photodetector; Photodiode; Photoelectric sensor; Photoionization detector; Photomultiplier; Photoresistor; Photoswitch; Phototransistor; Phototube; Piezoelectric accelerometer; Pirani gauge; Position sensor; Potentiometric sensor; Pressure gauge; Pressure sensor; Proximity sensor; Psychrometer; Pulse oximetry sensor; Pulse wave velocity monitor; Radio direction finder; Rain gauge; Rain sensor; Redox electrode; Reed switch; Resistance temperature detector; Resistance thermometer; Respiration sensor; Ring laser gyroscope; Rotary encoder; Rotary variable differential transformer; Scintillometer; Seismometer; Selsyn; Shack-Hartmann; Silicon bandgap temperature sensor; Smoke detector; Snow gauge; Soil moisture sensor; Speech monitor; Speed sensor; Stream gauge; Stud finder; Sudden Motion Sensor; Tachometer; Tactile sensor; Temperature gauge; Thermistor; Thermocouple; Thermometer; Tide gauge; Tilt sensor; Time pressure gauge; Touch switch; Triangulation sensor; Turn coordinator; Ultrasonic thickness gauge; Variometer; Vibrating structure gyroscope; Voltmeter; Water meter; Watt-hour meter; Wavefront sensor; Wired glove; Yaw rate sensor; and Zinc oxide nanorod sensor. Although this disclosure describes particular types of sensors, this disclosure contemplates any suitable types of sensors.

A biosensor is a type of sensor 112 that receives a biological stimulus and converts it into a data stream. As used herein, the term "biosensor" is used broadly.

In particular embodiments, a biosensor may be a device for the detection of an analyte. An analyte is a substance or chemical constituent that is determined in an analytical procedure. For instance, in an immunoassay, the analyte may be the ligand or the binder, while in blood glucose testing, the analyte is glucose. In medicine, analyte typically refers to the type of test being run on a patient, as the test is usually determining the existence and/or concentration of a chemical substance in the human body.

A common example of a commercial biosensor is a blood glucose monitor, which uses the enzyme glucose oxidase to break blood glucose down. In doing so, it first oxidizes glucose and uses two electrons to reduce the FAD (flavin adenine dinucleotide, a component of the enzyme) to $FADH_2$ (1,5-dihydro-FAD). This in turn is oxidized by the electrode (accepting two electrons from the electrode) in a number of steps. The resulting current is a measure of the concentration of glucose. In this case, the electrode is the transducer and the enzyme is the biologically active component.

In particular embodiments, a biosensor combines a biological component with a physicochemical detector component. A typical biosensor comprises: a sensitive biological element (e.g., biological material (tissue, microorganisms, organelles, cell receptors, enzymes, antibodies, nucleic acids, etc.), biologically derived material, biomimic); a physicochemical transducer/detector element (e.g. optical, piezoelectric, electrochemical) that transforms the signal (i.e. input stimulus) resulting from the interaction of the analyte with the biological element into another signal (i.e. transducers) that may be measured and quantified; and associated electronics or signal processors generating and transmitting a data stream corresponding to the input stimulus. The encapsulation of the biological component in a biosensor may be done by means of a semi-permeable barrier (e.g., a dialysis membrane or hydrogel), a 3D polymer matrix (e.g., by physically or chemically constraining the sensing macromolecule), or by other means.

Sensor Sampling Rates

In particular embodiments, a sensor 112 may sample input stimulus at discrete times. The sampling rate, sample rate, or sampling frequency defines the number of samples per second (or per other unit) taken from a continuous or semi-continuous stimulus to make a discrete data signal. For time-domain signals, the unit for sampling rate may be 1/s (Hertz). The inverse of the sampling frequency is the sampling period or sampling interval, which is the time between samples. The sampling rate of a sensor 112 may be controlled locally, remotely, or both.

In particular embodiments, one or more sensors 112 in the sensor array 110 may have a dynamic sampling rate. Dynamic sampling is performed when a decision to change the sampling rate is taken if the current outcome of a process is within or different from some specified value or range of values. As an example and not by way of limitation, if the stimulus is different from the outcome predicted by some model or falls outside some threshold range, the sensor 112 may increase or decrease its sampling rate in response. Dynamic sampling may be used to optimize the operation of the sensors 112 or influence the operation of actuators to change the environment.

In particular embodiments, the sampling rate of a sensor 112 may be based on receipt of a particular stimulus. As an example and not by way of limitation, an accelerometer may have a default sample rate of 1/s, but may increase its sampling rate to 60/s whenever it measures a non-zero value, and then may return to a 1/s sampling rate after getting 60 consecutive samples equal to zero. As another example and not by way of limitation, if the stimulus measured over a particular range of time does vary significantly, the sensor 112 may reduce its sampling rate.

In particular embodiments, the sampling rate of a sensor 112 may be based on input from one or more components of sensor network 100. As an example and not by way of limitation, a heart rate monitor may have a default sampling rate of 1/min, but may increase the its sampling rate in response to a signal or instruction from analysis system 180.

In particular embodiments, one or more sensors 112 in the sensor array 110 may increase or decrease the precision at which the sensors 112 sample input. As an example and not by way of limitation, a glucose monitor may use four bits to record a user's blood glucose level by default. However, if the user's blood glucose level begins varying quickly, the glucose monitor may increase its precision to eight-bit measurements.

User-Input Sensors

In particular embodiments, a user-input device may be a sensor 112 in sensor array 110. These "user-input sensors" are sensors 112 where the stimulus received by the sensor 112 may be input from a user. The user may input any suitable information into the sensor 112, including physiological, psychological, behavioral, or environmental information. The user may input information about the user (e.g., a user may record his psychological state) or about one or more 3rd parties (e.g., a doctor may record information about a patient). A user may provide input in a variety of ways. User-input may include, for example, inputting a quantity or value into the sensor 112, speaking or providing other audio input to the sensor 112, and touching or providing other stimulus to the sensor 112. Any client system with a suitable I/O device may serve as a user-input sensor. Suitable I/O devices include alphanumeric keyboards, numeric keypads, touch pads, touch screens, input keys, buttons, switches, microphones, pointing devices, navigation buttons, stylus, scroll dial, another suitable I/O device, or a combination of two or more of these.

In particular embodiments, an electronic calendar functions as a user-input sensor for gathering behavioral data. A user may input the time and day for various activities, including appointments, social interactions, phone calls, meetings, work, tasks, chores, etc. Each inputted activity may be further tagged with details, labels, and categories (e.g., "important," "personal," "birthday"). The electronic calendar may be any suitable personal information manager, such as Microsoft Outlook, Lotus Notes, Google Calendar, etc. The electronic calendar may then transmit the activity data as a data stream to analysis system 180, which could map the activity data over time and correlate it with data from other sensors in sensor array 110. For example, analysis system 180 may map a heart-rate data stream against the activity data stream from an electronic calendar, showing that the user's heart-rate peaked during a particularly stressful activity (e.g., dinner with the in-laws).

User Queries and Triggering User Queries Based on Sensor Inputs

In particular embodiments, a sensor 112 may query a user to input information (i.e., stimulus) into the sensor 112. The sensor 112 may query the user in any suitable manner, such as, for example, by prompting the user to input information into a suitable I/O device. The sensor 112 may query the user at any suitable rate or frequency. As an example and not by way of limitation, a sensor 112 may query a user at a static interval (e.g., every hour). As another example and not by way of limitation, a sensor 112 may query a user at a dynamic rate. The dynamic rate may be based on a variety of factors, including prior input into the sensor 112, data streams from other sensors 112 or nodes 114 in sensor array 110, output from analysis system 180, or other suitable factors. For example, if a heart-rate monitor in sensor array 110 indicates an increase in the user's heart-rate, a user-input sensor may immediately query the user to input his current activity. Although this disclosure describes particular components performing particular processes to query a user to input information into a sensor 112, this disclosure contemplates any suitable components performing any suitable processes to query a user to input information into a sensor 112.

In particular embodiments, analysis system 180 may access one or more data streams from one or more sensors 112. The sensors may be physiological, psychological, behavioral, or environmental sensors. Similarly, each data stream may comprise physiological, psychological, behavioral, or environmental data of a person. In particular embodiments, analysis system 180 may access one or more physiological sensors, the physiological sensors comprising one or more of a heart-rate monitor, a blood-pressure monitor, a pulse oximeter, an accelerometer, an electrocardiograph, a glucocorticoid meter, an electromyograph, another suitable physiological sensor, or two or more such sensors. As an example and not by way of limitation, analysis system 180 may access a data stream from a heart-rate monitor, wherein the data stream comprises heart-rate data of a person. In particular embodiments, analysis system 180 may access one or more environmental sensors that are data feeds, the data feeds comprising one or more of a stock-market ticker, a weather report, a news feed, a traffic-condition update, a public-health notice, an electronic calendar, a social network news feed, another suitable data feed, or two or more such data feeds. As an example and not by way of limitation, analysis system 180 may access a stock-market ticker from a data feed, wherein the stock-market ticker comprises stock information. Although this disclosure describes particular components accessing particular data streams from particular sensors 112, this disclosure contemplates any suitable components accessing any suitable data streams from any suitable sensors 112.

In particular embodiments, analysis system 180 may analyze a data stream in reference to its corresponding set of control parameters. Each sensor 112 or data stream may have a corresponding set of control parameters. The set of control parameters consists of data parameters that specify when a sensor 112 or data stream is at a normal or expected state. The set of control parameters may include one or more of a set point for the sensor 112, an operating range for the sensor 112, an operating threshold for the sensor 112, a sampling rate for the sensor 112, a sample size for the sensor 112, another suitable parameter, or two or more such parameters. As an example and not by way of limitation, a heart-rate monitor may have a corresponding set of control parameters that specify that a heart-rate of 60-100 beats/minute is a normal state. As another example and not by way of limitation, a mood sensor 400 may have a corresponding set of control parameters that specify that a self-reported psychological state of "stressed" with an intensity of 2 or less on a 0-to-4 Likert scale is a normal state. In particular embodiments, analysis system 180 may analyze a plurality of data streams in references to a plurality of corresponding sets of control parameters. The set of control parameters may specify when a first sensor 112 or first data stream is at a normal or expected state based on data from one or more second sensors 112 or second data streams. As an example and not by way of limitation, a heart-rate monitor and an accelerometer may have a corresponding set of control parameters that specify that once a period of extended activity has ended, a change in heart-rate of 12 beats/minute$^2$ or higher is a normal state (an continuously elevated heart rate after exercise may indicate an increased risk of heart attack). As another example and not by way of limitation, a mood sensor 400 and a weather report data feed may have a corresponding set of control parameters that specify that when the weather is overcast, a self-reported psychological state of "depressed" with an intensity of 3 or less on a 0-to-4 Likert scale is a normal state (a person is more likely to be depressed when the weather is poor). Although this disclosure describes particular components analyzing particular data streams in reference to particular sets of control parameters, this disclosure contemplates any suitable components analyzing any suitable data streams in reference to any suitable sets of control parameters.

In particular embodiments, analysis system 180 may analyze a data stream in reference to its corresponding set of control parameters to determine if the data stream deviates from its corresponding set of control parameters. Analysis system 180 may use any suitable process, calculation, or technique to determine if a data stream deviates from its corresponding set of control parameters. A sensor 112 or data stream deviates from its corresponding set of control parameters when one or more samples in the data stream indicate that the sensor or data stream is not at a normal or expected state. As an example and not by way of limitation, if a heart-rate monitor has a corresponding set of control parameters that specify that a heart-rate of 60-100 beats/minute is a normal state, analysis system 180 may compare one or more samples from the data stream from the heart-rate monitor with the set of control parameters corresponding to the heart-rate monitor to identify whether any of the samples indicate a heart-rate outside of the 60-100 beats/minute range. Although this disclosure describes particular components performing particular process to determine if a data stream deviates from its corresponding set of control parameters, this disclosure contemplates any suitable components performing any suitable processes to determine if a data stream deviates from its corresponding set of control parameters.

In particular embodiments, analysis system 180 may transmit a query to one or more sensors 112 for physiological, psychological, behavioral, or environmental information. The query may ask the user to input information about the user (e.g., asking the user to input his psychological state) or about one or more 3rd parties (e.g., asking a doctor to input physiological information about a patient). The query may ask an environment sensor for environment information (e.g., asking a weather sensor for the temperature at the user's location; asking a stock ticker for information on the user's stock portfolio). The sensor 112 may prompt the user to input data into the sensor 112 in any suitable manner, such as, for example, by inputting a quantity or value into the sensor 112, speaking or providing other audio input to the sensor 112, and touching or providing other stimulus to the sensor 112. The sensor 112 may also automatically sample data without any user input. In particular embodiments, analysis system 180 may transmit a query to one or more mood sensors 400 for psychological or behavioral data of the user. The mood sensor 400 may prompt the user to input psychological or behavioral data into mood collection interface 420. As an example and not by way of limitation, analysis system 180 may transmit a query to a mood sensor 400 for mood, mood intensity, and activity data of a user. The mood sensor 400 may display a message or other notification in mood collection interface 420 instructing the user to input mood and activity data into the mood collection interface 420. Although this disclosure describes particular components transmitting particular queries, this disclosure contemplates any suitable components transmitting any suitable queries. Moreover, although this disclosure describes transmitting queries to particular sensors 112 for particular information, this disclosure contemplates transmitting queries to any suitable sensors 112 for any suitable information.

In particular embodiments, analysis system 180 may receive one or more data streams from one or more sensors 112 in response to a query. The data streams may contain physiological, psychological, behavioral, or environmental data from a sensor 112 in response to the query. In particular embodiments, analysis system 180 may receive one or more data streams from one or more mood sensor 400 in response to a query. The data streams from mood sensor 400 may contain psychological or behavioral data in response to the query. As an example and not by way of limitation, analysis system 180 may transmit a query to mood sensor 400 for mood and mood intensity data of the user. The user may input that he is "stressed" with an intensity of 2 on a 0-to-4 Likert scale. The mood sensor 400 may then transmit a data stream comprising the user's mood and mood intensity data to analysis system 180 in response to the query, the data stream being received by analysis system 180. As another example and not by way of limitation, analysis system 180 may transmit a query to mood sensor 400 for activity data of the user. The user may input that he is "driving." The mood sensor 400 may then transmit a data stream comprising the user's activity data to analysis system 180 in response to the query, the data system being received by analysis system 180. Although this disclosure describes particular components receiving particular data streams, this disclosure contemplates any suitable components receiving any suitable data streams. Moreover, although this disclosure describes receiving particular data streams in response to particular queries, this disclosure contemplates receiving any suitable data streams in response to any suitable queries.

In particular embodiments, a sensor 112 may query a user to take a sample with the sensor 112. The sensor 112 may query the user in any suitable manner, such as, for example, by prompting the user to use or activate the sensor 112. As an example and not by way of limitation, analysis system 180 may transmit a query to a blood-glucose monitor for blood-glucose data of a user. The blood-glucose monitor may notify the user of the query with a suitable audio or visual prompt. The user may then take a blood sample with the blood-glucose monitor, and the blood-glucose monitor may transmit a data stream based on this sample to analysis system 180. Although this disclosure describes particular components performing particular processes to query a user to take a sample with a sensor 112, this disclosure contemplates any suitable components performing any suitable processes to take a sample with a sensor 112.

Figure 3:
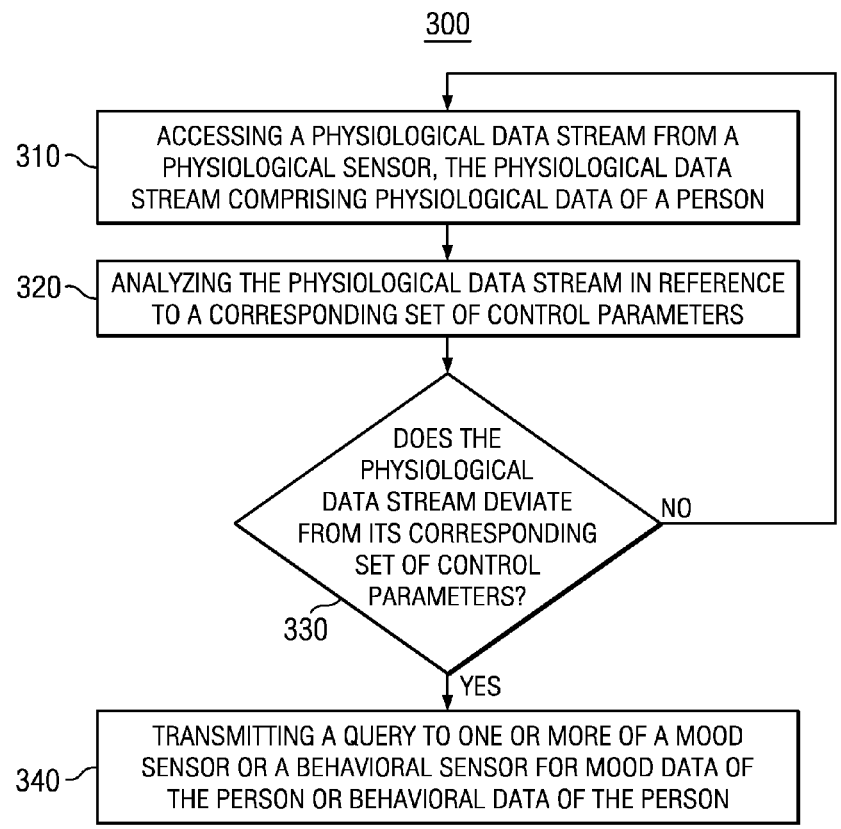
FIG. 3 illustrates an example method for triggering user queries based on sensor inputs.

FIG. 3 illustrates an example method 300 for triggering user queries based on sensor inputs. The method begins at step 310, where analysis system 180 accesses one or more physiological data streams from one or more physiological sensors, such as sensors 112. The physiological data streams comprise physiological data of a person. At step 320, analysis system 180 analyzes each physiological data stream in reference to a corresponding set of control parameters. At step 330, analysis system 180 determines if at least one of the physiological data streams deviates from its corresponding set of control parameters. If at least one of the physiological data streams deviates from its corresponding set of control parameters, then analysis system 180 transmits a query to one or more of a mood sensor or a behavioral sensor for mood data of the person or behavioral data of the person, respectively, at step 340. But if the physiological data stream do not deviate from their corresponding set of control parameters, then analysis system 180 may return to step 310. Although this disclosure describes and illustrates particular steps of the method of FIG. 3 as occurring in a particular order, this disclosure contemplates any suitable steps of the method of FIG. 3 occurring in any suitable order. Moreover, although this disclosure describes and illustrates particular components carrying out particular steps of the method of FIG. 3, this disclosure contemplates any suitable combination of any suitable components carrying out any suitable steps of the method of FIG. 3.

Mood/Behavioral Sensors

Figure 4:
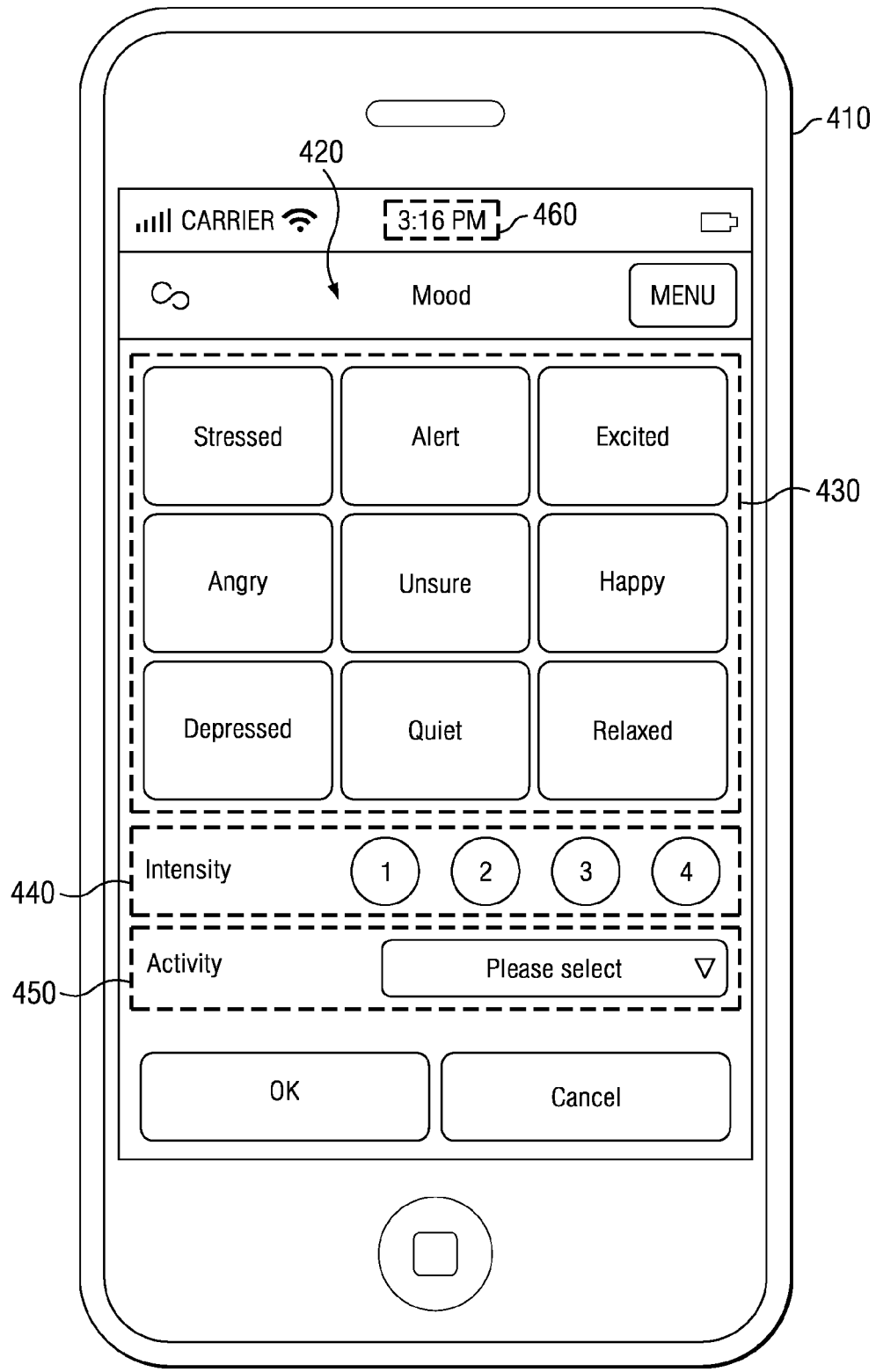
FIG. 4 illustrates an example sensor for collecting psychological and behavioral data from a person.

FIG. 4 illustrates an example sensor 400 for collecting psychological and behavioral information from a person. This "mood sensor" 400 is a type of user-input sensor that may receive psychological and behavioral input (i.e., stimulus) from a user. In some embodiments, a user may input psychological (i.e., mood) or behavioral (i.e., activity) information about the user. In other embodiments, the user may input psychological or behavioral information about one or more 3rd parties (e.g., a doctor may record information about a patient). This disclosure assumes that a user is recording information about the user, unless context suggests otherwise. Mood sensor 400 may server as a mood sensor for receiving psychological stimulus or as a behavioral sensor for receiving behavioral stimulus. Although this disclosure describes particular components performing particular processes to collect psychological and behavioral information from a person, this disclosure contemplates any suitable components performing any suitable processes to collect psychological and behavioral information from a person. Moreover, although this disclosure describes mood sensor 400 collecting particular types of psychological and behavior information about a person, this disclosure contemplates mood sensor 400 collecting any suitable types of psychological or behavioral information.

In particular embodiments, mood sensor 400 includes a software application that may be executed on client system 410. FIG. 4 illustrates a smart phone as an example client system 410, however any suitable user-input device may be used (e.g., cellular phone, personal digital assistant, personal computer, tablet computer, wearable computer, etc.). In some embodiments, a user may execute an application on client system 410 to access mood collection interface 420. In other embodiments, a user may use a browser client or other application on client system 410 to access mood collection interface 420 over a mobile network (or other suitable network). Mood collection interface 420 may be configured to receive signals from the user. As an example and not by way of limitation, the user may click, touch, speak, gesture, or otherwise interact with mood collection interface 420 to select and input psychological or behavioral information, or to perform other actions.

In particular embodiments, mood sensor 400 may include one or more of a mood input widget 430, a mood intensity input widget 440, an activity input widget 450, or a clock 460. Mood input widget 430 may be a three-by-three grid of mood icons, wherein each icon has a unique semantic label and color. The grid illustrated in FIG. 3 shows the following example moods and colors:

| Mood/Psychological State | Color |
|---|---|
| Stressed | Yellow |
| Alert | Orange |
| Excited | Pink |
| Angry | Red |
| Unsure | Grey |
| Happy | Green |
| Depressed | Maya blue |
| Quiet | Mauve |
| Relaxed | Light cornflower blue |

The user may touch one or more of the mood icons to input his current mood (i.e., psychological state). Mood intensity widget 440 is a row with numbered icons ranging from one to four that each correspond to a level of intensity of a psychological state. The numbers range from the lowest to highest intensity, with one being the lowest and four being the highest. The user may touch one of the numbers to input an intensity corresponding to a selected mood. In particular embodiments, the mood intensity corresponds to a standard psychometric scale (e.g., Likert scale). Activity input widget 450 is a drop-down menu containing a list of activities (i.e., behavioral states). The list is not illustrated, but could include a variety of behavioral states, such as sleeping, eating, working, driving, arguing, etc. The user may touch the drop-down menu to input one or more behavioral states. In particular embodiments, the selected behavioral state may correspond to a selected psychological state. Clock 460 provides the current time according to client system 410. This time may be automatically inputted as a timestamp to any other inputs on mood collection interface 420. In particular embodiments, a time or duration of the psychological or behavioral state may be inputted manually by the user. Although this disclosure describes and FIG. 4 illustrates mood sensor 400 having particular components, this disclosure contemplates mood sensor 400 having any suitable components. Moreover, although this disclosure describes and FIG. 4 illustrates mood sensor 400 collecting psychological and behavioral information using particular components, this disclosure contemplates mood sensor 400 collecting psychological or behavioral information using any suitable components. As an example and not by way of limitation, psychological or behavioral information about a user may be entered manually by the user without the use of widgets, icons, drop-down menus, or timestamps. This would allow the user to input a variety of psychological or behavioral information for any time or time period.

In particular embodiments, mood sensor 400 may be a sensor 112 in sensor array 110. After receiving the psychological or behavioral data, the mood sensor 400 may transmit the data as one or more data streams to node 114, analysis system 180, or another suitable system.

In particular embodiments, mood sensor 400 may query a user to input psychological or behavioral information. The user may input any suitable psychological or behavioral information into the mood sensor 400. The user may input information about the user (e.g., a user may record his psychological state) or about one or more 3rd parties (e.g., a psychiatrist may record psychological information about a patient). The mood sensor 400 may query the user at any suitable rate or frequency. As an example and not by way of limitation, mood sensor 400 may query a user at a static interval (e.g., every hour). As another example and not by way of limitation, mood sensor 400 may query a user at a dynamic rate. The dynamic rate may be based on a variety of factors, including prior input into mood sensor 400, data streams from other sensors 112 or nodes 114 in sensor array 110, output from analysis system 180, requests or queries from other systems, or other suitable factors. For example, if the user inputs that he is "angry" with an intensity of "4," mood sensor 400 may begin querying the user every 15 minutes until the user indicates the intensity of his mood has dropped to "2" or less. In another example, if a heart-rate monitor in sensor array 110 indicates an increase in the user's heart-rate, mood sensor 400 may query the user to input his current psychological and behavioral state. In yet another example, if the user's electronic calendar indicates that he has an appointment tagged as "important," mood sensor 400 may query the user to input his psychological state immediately before and after the appointment. Although this disclosure describes particular components performing particular processes to query a user to input psychological or behavioral information into mood sensor 400, this disclosure contemplates any suitable components performing any suitable processes to query a user to input psychological or behavioral information into mood sensor 400.

In particular embodiments, mood sensor 400 may administer one or more therapies or therapeutic feedbacks. A therapy may be provided based on a variety of factors. Mood sensor 400 may provide therapeutic feedback to the user either during or after the user inputs a negative psychological or behavioral state. As an example and not by way of limitation, if the user touches the "angry" button, the display may change to show a calming image of puppies playing in the grass. Mood sensor 400 may also provide therapeutic feedback to the user based on output from analysis system 180. As an example and not by way of limitation, if a heart-rate monitor in sensor array 110 indicates an increase in the user's heart-rate, and the user inputs "stressed" into mood sensor 400, the analysis system 180 may determine that a therapeutic feedback is needed. In response to this determination, mood sensor 400 may play relaxing music to calm the user. Mood sensor 400 may deliver a variety of therapies, such as interventions, biofeedback, breathing exercises, progressive muscle relaxation exercises, presentation of personal media (e.g., music, personal pictures, etc.), offering an exit strategy (e.g., calling the user so he has an excuse to leave a stressful situation), references to a range of psychotherapeutic techniques, and graphical representations of trends (e.g., illustrations of health metrics over time), cognitive reframing therapy, and other therapeutic feedbacks. Mood sensor 400 may also provide information on where the user can seek other therapies, such as specific recommendations for medical care providers, hospitals, etc. Although this disclosure describes administering particular therapeutic feedbacks, this disclosure contemplates administering any suitable therapeutic feedbacks. Moreover, although this disclosure describes administering therapeutic feedbacks in a particular manner, this disclosure contemplates administering therapeutic feedbacks in any suitable manner.

In particular embodiments, mood sensor 400 may be used to access and display psychological or behavioral data related to the user on display system 190. Display system 190 may display data on mood collection interface 420 (i.e., the smartphone's touch screen) or another suitable display. Mood sensor 400 may access a local data store (e.g., prior psychological and behavioral input stored on the user's smart phone) or a remote data store (e.g., medical records from the user's hospital) over any suitable network. Mood sensor 400 may access and display mood and activity information previously recorded by mood sensor 400. As an example and not by way of limitation, the user could click on the "happy" button to access data showing the intensity, behavior, and time associated with each input of "happy" by the user on mood sensor 400. Mood sensor 400 may also access and display data recorded by other sensors 112 or medical procedures. As an example and not by way of limitation, the user could click on the "depressed" button to access data from one or more other sensors 112 in sensor array 110 (e.g., heart-rate sensor data, pulse oximetry sensor data, etc.) that correspond to each input of "depressed" by the user on mood sensor 400. Although this disclosure describes accessing and displaying particular psychological and behavioral data, this disclosure contemplates accessing and displaying any suitable psychological or behavioral data.

Figure 5:
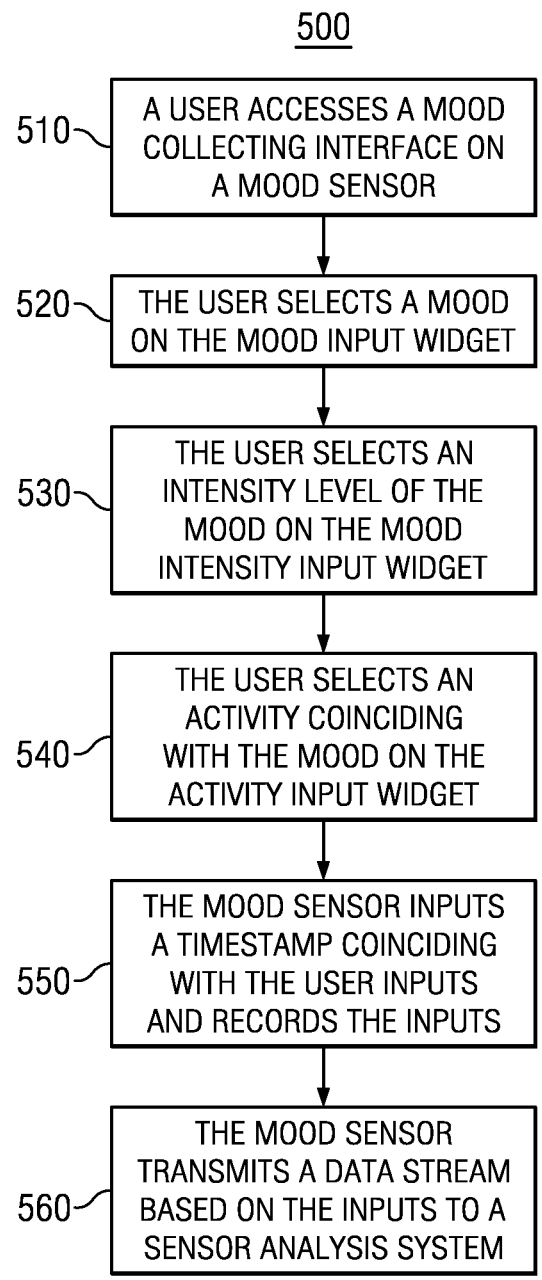
FIG. 5 illustrates an example method for collecting psychological and behavioral data from a person.

FIG. 5 illustrates an example method 500 for collecting psychological and behavioral information from a person. A user of mood sensor 400 may first access mood collection interface 420 on client system 410 at step 510. The user may select one or more moods (i.e., psychological states) on mood input widget 430 by touching one of the mood icons at step 520. The user may select an intensity level of the selected mood on mood intensity input widget 440 at step 530. The user may select an activity (i.e., behavioral state) coinciding with the selected mood on activity input widget 450 at step 540. After all three inputs are entered by the user, mood sensor 400 may automatically record the inputs or the user may indicate that he is done inputting moods and activities by clicking "ok" or providing some other input at step 550. At this step, the mood sensor may also record a time indication coinciding with the inputs. Finally, mood sensor 400 may transmit a data stream based on one or more of the mood, intensity, activity, or time inputs to analysis system 180 at step 560. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates particular components carrying out particular steps of the method of FIG. 5, this disclosure contemplates any suitable combination of any suitable components carrying out any suitable steps of the method of FIG. 5.

Data Feeds as Sensors

In particular embodiments, a sensor 112 may be a data feed. A data feed may be a computing system that receives and aggregates physiological, psychological, behavioral, or environmental data from one or more sources and transmits one or more data streams based on the aggregated data. Alternatively, a data feed may be the one or more data streams based on the aggregated data. As an example and not by way of limitation, data feeds may be stock-market tickers, weather reports, news feeds, traffic-condition updates, public-health notices, electronic calendars, data from one or more other users (such as, for example, physiological, psychological, or behavioral data from another user), or any other suitable data feeds. A data feed may contain both personal and remote data, as discussed previously. A data feed may be from any suitable computing device (such as, for example, computer system 1600).

The example data feeds illustrated and described herein are provided for illustration purposes only and are not meant to be limiting. This disclosure contemplates the use of any suitable data feed.

Data Streams

In particular embodiments, a data stream comprises one or more data transmitted from one or more sensors 112 or from one or more nodes 114 in sensor array 110. A data stream may be a digital or analog signal that may be transmitted over any suitable transmission medium and further used in electronic devices. Sensor array 110 may transmit one or more data streams based on one or more stimuli to one or more analysis systems 180 over any suitable network.

A data stream may include signals from a variety of types of sensors 112, including physiological, psychological, behavioral, and environmental sensors. A sensor 112 generates a data stream corresponding to the stimulus it receives. As an example and not by way of limitation, a physiological sensor (e.g., an accelerometer) generates a physiological data stream (e.g., an accelerometer data stream, which includes, for example, data on the acceleration of a subject over time).

Sensor data may include any suitable information. In particular embodiments, sensor data includes measurements taken by one or more sensors 112. Sensor data may include samples that may have any suitable format. In particular embodiments, the format of the samples may be a tuple (or ordered set) that has one or more data parameters, and a particular sample may be a tuple of one or more values for the one or more data parameters. As an example and not by way of limitation, a tuple format (t, p) may have data parameters time t and pressure p, and a particular sample (t0, p0) may have values pressure p0 measured at time t0. The tuple format may include any suitable data parameters, such as one or more sensor parameters and/or one or more test parameters. A sensor parameter may correspond to one or more sensors 112, and a sensor value may record one or more measurements taken by one or more sensors 112. As an example and not by way of limitation, a sensor value may record a measurement taken by a sensor 112. A test parameter may correspond to a factor that describes a temporal, spatial, and/or environmental feature of a measurement process, and a test value may record the value of the feature when the measurements are taken. As an example and not by way of limitation, the parameter may be time and the parameter value may record a particular time at which measurements are taken.

In particular embodiments, a sensor 112 may transmit one or more data at discrete times. The transmitting rate, transmission rate, or transmitting frequency defines the number of transmissions per second (or per other unit) sent by a sensor to make a discrete data signal. For time-domain signals, the unit for transmitting rate may be 1/s (Hertz). The inverse of the transmitting frequency is the transmitting period or transmitting interval, which is the time between transmissions. The datum may be transmitted continuously, periodically, randomly, or with any other suitable frequency or period. This may or may not correlate with the sampling rate of the sensor.

Reference to sensor data may encompass a sensor data stream, and vice versa, where appropriate. Sensor data may relate to a sensor subject, wherein the sensor 112 receives stimulus from or related to the subject. Sensor data or a data stream may relate to a sensor subject in any suitable way. As an example and not by way of limitation, sensor data may relate to a sensor subject because one or more sensors 112 generated the sensor data from one or more stimuli produced by the sensor subject. As another example and not by way of limitation, sensor data may relate to a sensor subject because the sensor data may provide insight or further understanding of the sensor subject. As yet another example and not by way of limitation, sensor data may relate to a sensor subject because it may help detect or predict the occurrence of one or more problems or events concerning the sensor subject. As yet another example and not by way of limitation, sensor data may relate to a sensor subject because it may facilitate monitoring of the sensor subject.

Data Acquisition

In particular embodiments, the components of sensor network 100 may utilize some type of data acquisition system to further process the data stream signal for use by analysis system 180. As an example and not by way of limitation, a data acquisition system may convert an analog waveforms signal into a digital value. As another example and not by way of limitation, the data acquisition system may convert decimal values into binary values. The data acquisition system may be local, for example, integrated into a sensor 112 in sensor array 110 or into local analysis system 120. The data acquisition system may also be remote, for example, integrated into remote analysis system 150 or an independent system.

In particular embodiments, the data acquisition system may perform one or more signal conditioning processes (for example, if a signal from a sensor 112 is not suitable for the type of analysis system 180 being used). As an example and not by way of limitation, the data acquisition system may amplify, filter, or demodulate the signal. Various other examples of signal conditioning might be bridge completion, providing current or voltage excitation to the sensor, isolation, time-base correction, and linearization. In particular embodiments, single-ended analog signals may be converted to differential signals. In particular embodiments, digital signals may be encoded to reduce and correct transmission errors or downsampled to reduce transmission power requirements.

Data Logging

In particular embodiments, the components of sensor network 100 may utilize some type of data logging system to record, categorize, store, and file data from one or more data streams over time. The data logging system may be local, for example, integrated into a sensor 112 in sensor array 110 or into local analysis system 120. The data logging system may also be remote, for example, integrated into remote analysis system 150 or an independent system. The data logging system may also use distributed resources to record data. The data logging system may store data on any suitable data store, such as, for example, data store 1740.

The data logging system may record data streams as one or more data sets. A data set comprises one or more data from a data stream. Data sets may be categorized and formed based on a variety of criteria. As an example and not by way of limitation, a data stream could be recorded as one or more data sets based on the specific subject, sensor, time period, event, or other criteria.

In particular embodiments, one or more data sets from a data stream may be used to construct a binary decision diagram (BDD) representing the data sets.

Data Aggregation

In particular embodiments, the components of sensor network 100 may utilize a data aggregation system to process one or more data streams for use by analysis system 180 or display system 190. In particular embodiments, one or more nodes 114 may be data aggregation systems. As an example and not by way of limitation, a data aggregation system may monitor, synchronize, store, or analyze one or more data streams from one or more sensors 112 in sensor array 110. As another example and not by way of limitation, the data aggregation system may analyze one or more data streams from one or more sensors and generate one or more derivative data streams that may be synchronized, stored, and transmitted.

In particular embodiments, the data aggregation system may access the data streams from one or more sensors 112. A data stream from a sensor 112 may be transmitted to a data aggregation system over any suitable medium. As an example and not by way of limitation, a data aggregation system may be connected to one or more sensors by one or more connections 116. The data aggregation system may include one or more connection interfaces, such as, for example, a USB interface, a Firewire interface, a 802.11 interface, a Bluetooth interface, another suitable connection interface, or two or more such interfaces. Although this disclosure describes particular connection interfaces, this disclosure contemplates any suitable connection interface.

In particular embodiments, a data aggregation system may access data streams from one or more sensors 112 and synchronize the data streams. The data aggregation system may include one or more system clocks that may run synchronously or asynchronously of one or more other components in sensor network 100. In some embodiments, the system clock may be integrated into the data aggregation system. In other embodiments, the system clock may reference one or more external time systems, such as a clock in sensor array 110, sensor 112, analysis system 180, display system 190, or another suitable system. One or more sensors 112 may have one or more sample frequencies or transmission frequencies. The sample frequencies and transmission frequencies of a sensor 112 in sensor array 110 may differ from the sample frequencies or transmission frequencies of one or more other sensors 112 in sensor array 110. As an example and not by way of limitation, a first data stream from a first sensor 112 may comprise a tuple (s1, t1) representing a sample s1 with a local timestamp t1 based on a local clock on the first sensor 112. A second data stream from a second sensor 112 may comprise a tuple (s2, t2) representing a sample s2 with a local timestamp t2 based on a local clock on the second sensor 112. If the first sensor 112 and the second sensor 112 are not synchronized with each other, then samples s1 and s2 may have been taken at the same absolute time even though timestamps t1 and t2 are not the same value. In particular embodiments, the data aggregation system may synchronize the first and second data streams by associating a system timestamp with each sample based on a system clock integrated into the data aggregation system. As an example and not by way of limitation, the data aggregation system may associate the system timestamp with each sample when the sample arrives at the data aggregation system. The data aggregation system may assign the samples a timestamp t' based on the system clock. The data aggregation system may overwrite the local timestamps, resulting in tuples (s1, t') and (s2, t'), or the data aggregation system may add the timestamp t' to the tuples, resulting in tuples (s1, t1, t') and (s2, t2, t'). As another example and not by way of limitation, the data aggregation system may synchronize the local clocks on one or more sensors 112. The data aggregation system may periodically broadcast the system clock time to connected sensors 112. The connected sensors 112 may then adjust their internal clocks to match the broadcasted system clock's time. The connected sensors 112 may still sample and transmit data at frequencies independent of each other and of the data aggregation system, however when a connected sensor 112 takes a sample, it may associate the sample with a system timestamp based on the connected sensor's 112 internal clock. In this manner, when the samples taken by the connected sensors 112 reach the data aggregation system, the tuples will be (s1, t') and (s2, t'). In particular embodiments, analysis of the data streams may be more accurate and precise when the data streams are synchronized. As an example and not by way of limitation, sensor array 110 may include an accelerometer and a pulse oximeter. If the data streams from the two sensors are not synchronized, an analysis system 180 may not be able to accurately determine correlations between blood-oxygen levels and activity. Synchronizing data streams may allow more accurate analysis of the data streams for, in the case of this example, the causes of sudden blood-oxygen level changes. Although this disclosure describes a data aggregation system synchronizing particular data streams in a particular manner, this disclosure contemplates the data aggregation system synchronizing any suitable data streams in any suitable manner.

In particular embodiments, the data aggregation system may store the data streams from one or more sensors 112. The data aggregation system may record the data streams and the system timestamps associated with each of the samples. In particular embodiments, the data aggregation system may compress the data streams before storing. As an example and not by way of limitation, the data aggregation system may store the data streams with the system timestamps as one or more binary decision diagrams (BDDs). The data aggregation system may store the data streams with the system timestamps in any suitable, tangible storage medium such as, for example, an SD card, solid state device, hard drive, random access memory, or memory integrated in a web server. Although this disclosure describes a data aggregation system storing data streams in a particular manner, this disclosure contemplates the data aggregation system storing data streams in any suitable manner.

In particular embodiments, the data aggregation system may analyze one or more data streams from one or more sensors 112 and generate one or more derivative data streams that may be synchronized, stored, and transmitted. The data aggregation system may perform an operation on one or more data streams to generate a derivative data stream. As an example and not by way of limitation, the data aggregation system may use a meta-sensor that performs an operation on one or more data streams to generate a derivative data stream. In particular embodiments, the derivative data stream may comprise samples that represent measurements of stimuli not directly measured by the sensors 112 in sensor array 110. As an example and not by way of limitation, sensor array 110 may include an electrocardiogram and a pulse oximeter. The data aggregation system may use a meta-sensor to measure the time difference between the registered heartbeat spikes on the data stream from the electrocardiogram and on the data stream from the pulse oximeter to generate a derivative data stream comprising blood pressure data. In particular embodiments, the blood pressure may be calculated with the formula:

$$B = k_1 \ln\left(\frac{1}{p}\right) + k_2$$

where:
B is blood pressure,
$k_1$ is 159.6,
p is the pulse wave transit time, and
$k_2$ is −51.2.

In other embodiments, the blood pressure may be calculated with the formula:

$$B = k_1 \exp(k_2 p)$$

where:
B is blood pressure,
$k_1$ is 354.4
p is the pulse wave transit time, and
$k_2$ is −3.74.

In these formulas, the pulse wave transit time may be calculated from the time difference between heartbeat spikes on the data stream from the electrocardiogram and on the data stream from the pulse oximeter. In particular embodiments, the data aggregation system may begin generating a derivative data stream in response to the failure of one or more sensors 112 in sensor array 110. As an example and not by way of limitation, sensor array 110 may include an electrocardiogram, a pulse oximeter, and a blood pressure monitor. If the blood pressure monitor fails or ceases to operate, the data aggregation system may use a meta-sensor to measure the time difference between the registered heartbeat spikes on the data stream from the electrocardiogram and on the data stream from the pulse oximeter to generate a derivative data stream comprising blood pressure data. The data aggregation system may further synchronize, store, and transmit the derivative data stream comprising blood pressure data. Although this disclosure describes particular components performing particular processes to generate a derivative data stream, this disclosure contemplates any suitable components performing any suitable processes to generate a derivative data stream. Moreover, although this disclosure describes accessing particular data streams to generate particular derivative data streams, this disclosure contemplates accessing any suitable data streams to generate any suitable derivative data streams.

In particular embodiments, the data aggregation system may use the system timestamps associated with the samples to correlate one or more data streams from sensors 112 with each other or with information outside the data streams. The data aggregation system may also transmit the system timestamps with the results of correlating the original data streams with each other or with information outside the data streams. As an example and not by way of limitation, the data aggregation system may indicate that a particular person's blood pressure increases during holidays. As another example and not by way of limitation, the data aggregation system may indicate that a particular person's heartbeats become more irregular when the person's blood pressure is higher. Although this disclosure describes using system timestamps to correlate data streams in a particular manner, this disclosure contemplates using system timestamps to correlate data streams in any suitable manner.

In particular embodiments, the data aggregation system may transmit the data streams or derivative data streams to one or more components of sensor network 100. As an example and not by way of limitation, the data aggregation system may transmit the data streams or derivative data streams to analysis system 180, display system 190, or network 160 via connection 116. The data aggregation system may further transmit the system timestamps associated with the samples in the data streams or derivative data streams. As another example and not by way of limitation, the data aggregation system may transmit the data streams and derivative data streams across one or more portions of the Internet. In particular embodiments, the data aggregation system may transmit the data streams or derivative data streams along with system timestamps associated with the samples in the data streams or derivative data streams.

In particular embodiments, the data aggregation system may transmit a start time and a sampling frequency with the results of correlating one or more data streams from sensors 112 with each other or with information outside the data streams. The start time may represent the initial time when sensors 112 began sampling. The start time may represent the start time for the accessed data set. The sampling frequency may represent the frequency at which sensors 112 sample or record data. In particular embodiments, a data aggregation system, analysis system 180, or display system 190 may analyze or display the results of correlating the data streams by associating each data point in the results with a timestamp. The timestamps may be based upon the start time and the sampling frequency. As an example and not by way of limitation, the second data point in the results may be assigned the timestamp equal to the initial time plus the inverse of the sampling frequency. As another example and not by way of limitation, the $n^{th}$ data point in the results may be assigned a timestamp according to the formula:

$$t_s = t_i + n\left(\frac{1}{v}\right)$$

where:
$t_s$ is the timestamp,
$t_i$ is the initial time,
n is the $n^{th}$ data point, and
v is the sampling frequency.

Figure 6A:
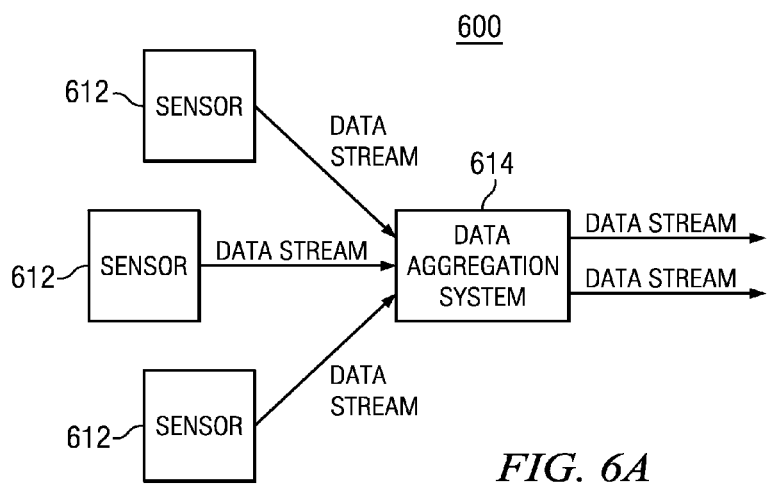
FIG. 6A illustrates an example data aggregation system and data flow to and from the data aggregation system.

FIG. 6A illustrates an example system 600 comprising data aggregation system 614 and data flow to and from the data aggregation system 614. Data aggregation system 614 may receive data streams from one or more sensors 612. Data aggregation system 614 may operate on the input data streams to generate and transmit one or more data streams. In particular embodiments, one or more sensors 612 may transmit data streams that are inputs into data aggregation system 614. As an example and not by way of limitation, the data streams may comprise data about a person (or group of persons or entities), place (such as, for example, a geographical location), or thing (such as, for example, a building, road, or car). Although this disclosure describes particular types of data streams, this disclosure contemplates any suitable types of data streams. Data aggregation system 614 may receive one or more data streams as input and may operate on them to generate one or more data streams. As an example and not by way of limitation, data aggregation system 614 may synchronize the input data streams to generate one or more data streams. As another example and not by way of limitation, data aggregation system 614 may perform a mathematical operation (such as, for example, addition or subtraction) on one or more data streams to generate a data stream. Although this disclosure describes particular types of operations performed on data streams, this disclosure contemplates any suitable types of operations. Data aggregation system 614 may transmit one or more data streams as output. As an example and not by way of limitation, data aggregation system 614 may transmit the data streams to an analysis system, display system, or network. Data aggregation system 614 may transmit the data streams over a wired interface (such as, for example, a USB interface or a Firewire interface) a wireless interface (such as, for example, an 802.11 interface or a Bluetooth interface) another suitable interface, or two or more such interfaces. Although this disclosure describes particular types of transmission interfaces, this disclosure contemplates any suitable types of interfaces. Although FIG. 6A illustrates a particular arrangement of sensors 612 and data aggregation system 614, this disclosure contemplates any suitable arrangement of sensors 612 and data aggregation system 614. Moreover, although FIG. 6A illustrates a particular data flow between sensors 612 and data aggregation system 614, this disclosure contemplates any suitable data flow between sensors 612 and data aggregation system 614.

Figure 6B:
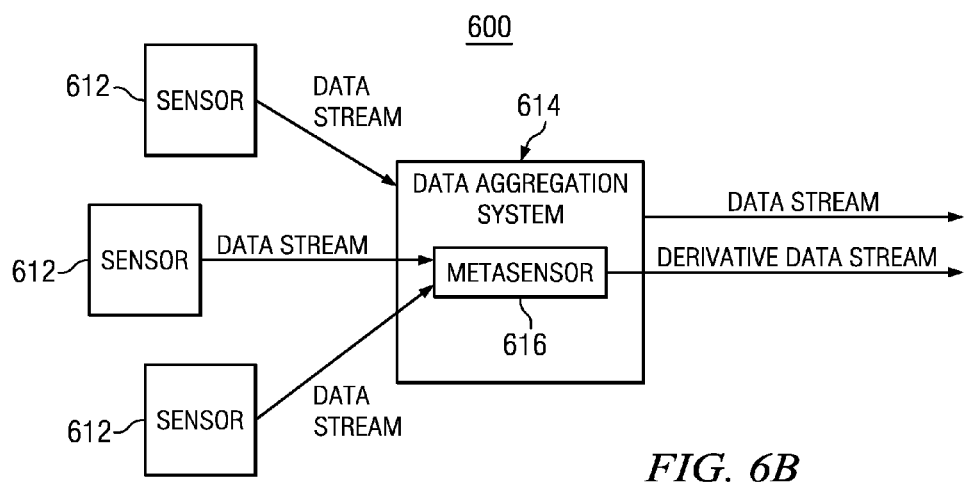
FIG. 6B illustrate an example data aggregation system and data flow to and from the data aggregation system.

FIG. 6B illustrates an example system 600 comprising data aggregation system 614 and data flow to and from the data aggregation system 614. Data aggregation system 614 may receive data streams from one or more sensors 612. Data aggregation system 614 may include a meta-sensor 616 that operates on one or more input data streams to generate a derivative data stream. Meta-sensor 616 may use any suitable process, calculation, or technique to generate a derivate data stream. In particular embodiments, a derivative data stream may include data not directly measured by one or more sensors 612. Although FIG. 6B illustrates a particular arrangement of sensors 612, data aggregation system 614, and meta-sensor 616, this disclosure contemplates any suitable arrangement of sensors 612, data aggregation system 614, and meta-sensor 616. Moreover, although FIG. 6B illustrates a particular data flow between sensors 612, data aggregation system 614, and meta-sensor 616, this disclosure contemplates any suitable data flow between sensors 612, data aggregation system 614, and meta-sensor 616.

FIG. 7A illustrates an example of a data aggregation system 714. In particular embodiments, data aggregation system 714 comprises one or more ports 730, a display 780, and a transmitter 760. One or more ports 730 may be configured to receive data streams from one or more sensors. As an example and not by way of limitation, ports 730 may be USB ports, Firewire ports, another suitable port, or two or more such ports. Although this disclosure describes particular types of ports, this disclosure contemplates any suitable types of ports. Display 780 may be configured to display a data stream. In particular embodiments, display 780 comprises a screen that displays a visual representation of a data stream. In other embodiments, display 780 comprises one or more light emitting diodes displaying light patterns that represent a data stream. Although this disclosure describes particular types of displays, this disclosure contemplates any suitable type of display. Transmitter 760 may be configured to transmit data streams to analysis systems, display systems, or networks. In particular embodiments, transmitter 760 may transmit data streams over a wired interface (such as, for example, a USB interface or a Firewire interface), a wireless interface (such as, for example, an 802.11 interface or a Bluetooth interface), another suitable interface, or two or more such interfaces.

Although this disclosure describes particular transmission interfaces, this disclosure contemplates any suitable transmission interface. In particular embodiments, data aggregation system 714 may further comprise a power cable 720 coupled to a power port 725, a data cable 740 coupled to a port 730, and a power button 750. Power cable 720 may supply electric power to data aggregation system 714 through power port 725. Data cable 740 may be the data transfer medium through which data streams travel to reach data aggregation system 714. In particular embodiments, data cable 740 may be a USB cable, a Firewire cable, or another suitable cable. Although this disclosure describes particular types of data cables, this disclosure contemplates any suitable types of data cables. Power button 750 may be configured to change the state of the data aggregation system 714. In particular embodiments, power button 750 may, when pressed, change data aggregation system 714 from an "ON" state to an "OFF" state. In other embodiments, power button may, when pressed, change data aggregation system 714 from an "ON" state to a "STANDBY" state. Although this disclosure describes the data aggregation system operating in particular states, this disclosure contemplates the data aggregation system operating in any suitable state. Although FIG. 7A describes a particular arrangement of ports 730, display 780, transmitter 760, power cable 720, power port 725, data cable 740, and power button 750, this disclosure contemplates any suitable arrangement of ports 730, display 780, transmitter 760, power cable 720, power port 725, data cable 740, and power button 750.

FIG. 7B illustrates an example of a data aggregation system 714. In particular embodiments, data aggregation system 714 comprises a receiver unit 735 comprising one or more ports 730, a processor unit 770 comprising a synchronizer 771 and an operator 772, a storage unit 775, and a transmitter 760. Receiver unit 735 receives one or more data streams at the one or more ports 730. As an example and not by way of limitation, receiver unit 735 may be configured so that each port 730 receives one data stream. In particular embodiments, each port 730 comprises a data transfer interface. As an example and not by way of limitation, port 730 may comprise a USB interface, Firewire interface, 802.11 interface, or Bluetooth interface. Although this disclosure describes particular data transfer interfaces, this disclosure contemplates any suitable data transfer interface. Processor unit 770 may receive data streams from receiver unit 735 and may receive input from storage unit 775. Processor unit 770 may output data streams to transmitter 760 and display 780. In particular embodiments, processor unit 770 may be a processor coupled to a memory. As an example and not by way of limitation, processor unit 770 may be a C64× processor or an ARM processor. Although this disclosure describes particular types of processors, this disclosure contemplates any suitable type of processor. In particular embodiments, processor unit 770 may comprise synchronizer 771. Synchronizer 771 may synchronize the timestamps associated with the samples in one or more data streams. Synchronizer 771 may use any suitable process or technique to synchronize the timestamps. In particular embodiments, processor unit 770 may comprise operator 772. Operator 772 may operate on one or more data streams to generate a derivative data stream. Operator 772 may use any suitable process, calculation, or technique to generate a derivative data stream. Storage unit 775 may store one or more data streams received from processor unit 770. Storage unit 775 may further store the timestamps associated with the samples in one or more data streams. As an example and not by way of limitation, storage unit 775 may comprise an SD card, solid state device, hard drive, random access memory, or memory integrated in a web server. Although this disclosure describes particular types of storage devices, this disclosure contemplates any suitable storage device. In particular embodiments, processor unit 770 may compress one or more data streams before sending them to storage unit 775. As an example and not by way of limitation, storage unit 775 may store one or more data streams and their associated timestamps as one or more binary decision diagrams (BDDs). Although this disclosure describes particular data compression algorithms, this disclosure contemplates any suitable data compression algorithm. In particular embodiments, storage unit 775 may send stored data streams to processor unit 770. Transmitter 760 may transmit data streams received from processor unit 770. Transmitter 760 may transmit data streams to display systems 190, analysis systems 180, or networks 160. Transmitter 760 may transmit the data streams over a wired interface (such as, for example, a USB interface or a Firewire interface), a wireless interface (such as, for example, an 802.11 interface or a Bluetooth interface), another suitable interface, or two or more such interfaces. Although this disclosure describes particular types of transmission interfaces, this disclosure contemplates any suitable types of interfaces. In particular embodiments, data aggregation system 714 further comprises a display 780. Display 780 may display data streams received from processor unit 770 in a visual format. As an example and not by way of limitation, display 780 may display a data stream as a graph, chart, or table. Although this disclosure describes particular visual formats, this disclosure contemplates any suitable visual format. In particular embodiments, data aggregation system 714 further comprises a battery 725. Battery 725 may supply electric power to the elements of data aggregation system 714. As an example and not by way of limitation, battery 725 may supply electric power to receiver unit 735, processor unit 770, storage unit 775, transmitter 760, and display 780. In particular embodiments, battery 725 may be rechargeable. Battery 725 may comprise a recharging interface that receives electric power from an external source. As an example and not by way of limitation, battery 725 may comprise an interface to receive a power cable 720. Although FIG. 7B describes a particular arrangement of ports 730, receiver unit 735, processor unit 770, synchronizer 771, operator 772, display 780, transmitter 760, storage unit 775, and battery 725, this disclosure contemplates any suitable arrangement of ports 730, receiver unit 735, processor unit 770, synchronizer 771, operator 772, display 780, transmitter 760, storage unit 775, and battery 725. Moreover, although FIG. 7B illustrates a particular data flow within data aggregation system 714, this disclosure contemplates any suitable data flow within data aggregation system 714.

FIG. 8 illustrates an example method 800 for synchronizing data streams. The method begins at step 810, where a mobile computing device accesses an original data stream from each of one or more sensors. The mobile computing device may be a data aggregation system 614 or 714, a node 114, or another suitable system. Each of the original data streams may comprise a series of samples that each represent a measurement of a stimulus sensed by the sensors that the original data stream is from. One or more of the sensors may be affixed to a person's body. At step 820, the mobile computing device associates a system timestamp with each of the samples based on a system clock. The system clock may operate independently of the sensors. At step 830, the mobile computing device records the original data streams with the system timestamps associated with their samples. This may be used for correlation of the original data streams with each other or with information outside the data streams. Although this disclosure describes particular compression algorithms, this disclosure contemplates any suitable compression algorithm. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates particular components carrying out particular steps of the method of FIG. 8, this disclosure contemplates any suitable combination of any suitable components carrying out any suitable steps of the method of FIG. 8.

Analysis

Analysis system 180 may monitor, store, and analyze one or more data streams from one or more sensors 112 or from one or more nodes 114 in sensor array 110. A data stream from a sensor 112 or a node 114 may be transmitted to analysis system 180 over any suitable medium. Analysis system 180 may transmit one or more analysis outputs based on the one or more data streams to one or more other components of sensor network 100, such as, for example, sensors 112, nodes 114, other analysis systems 180, or display systems 190. Analysis system 180 may be any suitable computing device, such as, for example, computer system 1600.

In particular embodiments, analysis system 180 may comprise one or more local analysis systems 120 or one or more remote analysis systems 150. Where analysis system 180 comprises multiple subsystems (e.g., local analysis system 120 and remote analysis system 150), processing and analysis of the data streams may occur in series or in parallel. As an example and not by way of limitation, analysis system 180 may receive identical data streams from a sensor 112 at both local analysis system 120 and remote analysis system 150. As another example and not by way of limitation, analysis system 180 may receive a data stream at local analysis system 120, which may process the data stream and then transmit a modified data stream/analysis output to remote analysis system 150.

In particular embodiments, analysis system 180 may access and analyze one or more data sets from a data stream. Analysis system 180 may analyze a data stream in real-time as it is received from sensor array 110, or it may store the data stream after it is received from sensor array 110 for subsequently process the data stream. Analysis system 180 may use any suitable process, calculation, or technique to analyze a data stream. As an example and not by way of limitation, analysis system 180 may perform a variety of processes and calculations, including ranging, inspecting, cleaning, filtering, transforming, modeling, normalizing, averaging, annotating, correlating, or contextualizing data. As another example and not by way of limitation, analysis system 180 may use a variety of data analysis techniques, including data mining, data fusion, distributed database processing, or artificial intelligence. These techniques may be applied to analyze various data streams and to generate correlations and conclusions based on the data. Analysis system 180 may analyze a plurality of data streams to determine if the data streams are related. A relationship between data streams may include, for example, correlations, causal relationships, dependent relationships, reciprocal relationships, data equivalence, another suitable relationship, or two or more such relationship. Although this disclosure describes analysis system 180 performing particular analytical processes using particular techniques, this disclosure contemplates analysis system 180 performing any suitable analytical processes using any suitable techniques.

Modeling Data Streams

In particular embodiments, analysis system 180 may generate models based on one or more data streams. A model is a means for describing a system or object. As an example and not by way of limitation, a model may be a data set, function, algorithm, differential equation, chart, table, decision tree, binary decision diagram, simulation, another suitable model, or two or more such models. A model may describe a variety of systems or objects, including one or more aspects of one or more persons' physiology, psychology, behavior, or environment. Although this disclosure describes particular components generating particular models, this disclosure contemplates any suitable components generating any suitable models. Moreover, although this disclosure describes generating particular models using particular techniques, this disclosure contemplates generating any suitable models using any suitable techniques.

Analysis system 180 may generate models that are empirical, theoretical, linear, nonlinear, deterministic, probabilistic, static, dynamic, heterogeneous, or homogenous. Analysis system 180 may generate models that fit one or more data points using a variety of techniques, including, for example, curve fitting, model training, interpolation, extrapolation, statistical modeling, nonparametric statistics, differential equations, etc.

Analysis system 180 may generate models of various types, including baseline models, statistical models, predictive models, etc. A baseline model is a model that serves as a basis for comparison, and is typically generated using controlled data (i.e., baseline data) over a specified period (i.e., a control period). The control period may be any suitable period. As an example and not by way of limitation, a baseline model of a subject's blood pressure may simply be the subject's average blood pressure calculated from a series of blood-pressure measurements taken over the course of a week by a blood-pressure monitor. A predictive model is a mathematical function (or set of functions) that describe the behavior of a system or object in terms of one or more independent variables. As an example and not by way of limitation, a predictive model that may be used to calculate a physiological state based on one or more actual sensor measurements. A type of predictive model is a statistical model, which is a mathematical function (or set of functions) that describe the behavior of an object of study in terms of random variables and their associated probability distributions. One of the most basic statistical models is the simple linear regression model, which assumes a linear relationship between two measured variables. As an example and not by way of limitation, analysis system 180 may compare data from a pulse oximeter and a barometer and identify a linear correlation between a subject's blood-oxygen level and the barometric pressure at the subject's location. In particular embodiments, a predictive model may be used as a baseline model, wherein the predictive model was generated using controlled data over a specified period.

In particular embodiments, analysis system 180 may generate a model by normalizing or averaging one or more data streams. As an example and not by way of limitation, a model of a data stream from a single sensor 112 could simply be the average sensor measurement made by the sensor 112 over some initialization period. As another example and not by way of limitation, a model could be a single sensor 112 measurement made during a control period.

In particular embodiments, analysis system 180 may generate a model by fitting one or more data sets to a mathematical function. As an example and not by way of limitation, a model could be an algorithm based on sensor measurements made by one or more sensors over some control period. The model may include a variety of variables, including data from one or more data streams and one or more fixed variables. The following is an example algorithm that analysis system 180 could generate to model a system or object:

$$f_m = f(D_{sensor}^1, \ldots, D_{sensor}^N, Y^1, \ldots, Y^M)$$

where:

$f_m$ is the model, $(D_{sensor}^1, \ldots, D_{sensor}^N)$ are data streams 1 through N, and $(Y^1, \ldots, Y^M)$ are fixed variables 1 through M.

In particular embodiments, the model may be used to predict hypothetical sensor measurements in theoretical or experimental systems. In particular embodiments, the model may be used to determine or categorize a subject's physiological or psychological state. As an example and not by way of limitation, the model may determine a subject's risk for a certain disease state with an abstract or statistical result. The model could simply identify the subject as being at "high risk" of developing a disease, or identify the subject as being 80% likely to develop the disease. As another example and not by way of limitation, the model may determine a subject's severity or grade of a disease state.

Contextualizing and Correlating Data Streams

In particular embodiments, analysis system 180 may map one or more data streams over time, allowing the data streams to be compared. Mapping and comparing the data streams allows analysis system 180 to contextualize and correlate a data set from one data stream with data sets from one or more other data streams.

In particular embodiments, analysis system 180 may analyze physiological, psychological, behavioral, or environmental data steams to contextualize one data set with another data set. Contextualizing is the process of interpreting a data set against the background of information provided by one or more data streams. As an example and not by way of limitation, a user may be wearing a heart-rate monitor and an accelerometer, which transmit a heart-rate data stream and an accelerometer data stream, respectively. A data set in the heart-rate data stream may show the user had an elevated heart-rate during a certain time period. Analysis system 180 may contextualize the heart-rate data by mapping the heart-rate data against data from an accelerometer data stream that shows that the user had an elevated activity during the same time period. A data set may be contextualized using data from a data stream from a sensor 112 or from fixed data accessed by analysis system 180. As another example and not by way of limitation, a data set of a user's heart rate from a heart-rate monitor may be contextualized against a data set of the user's genome.

In particular embodiments, analysis system 180 may analyze physiological, psychological, behavioral, or environmental data steams to identify correlations between certain data sets. Correlating is establishing or demonstrating a causal, complementary, parallel, or reciprocal relation between one data set and another data set. As an example and not by way of limitation, there is a positive correlation activity level in a person and the heart rate of the person. Analysis system 180 may analyze heart-rate data and accelerometer data and establish that when a user increases his activity beyond a certain level, it will cause an increase in his heart-rate and that activity level and heart-rate will increase proportionally until the user's heart-rate reaches a certain rate. The degree of correlation is the degree to which two or more measurements change simultaneously. These correlations may be of varying degrees of dependence (e.g., as determined by a Pearson's product-moment coefficient). In general, analysis system 180 may make more accurate correlations as more data becomes available from sensor array 110. Analysis system 180 may then use these correlations to generate causality hypotheses of varying degrees of confidence. In general, analysis system 180 may make more accurate correlations as more data becomes available from sensor array 110.

In particular embodiments, analysis system 180 may contextualize and correlate a data set from one or more data streams that exhibits some type of deviation, variability, or change. The deviation, variability, or change in a data stream may be with respect to other data sets in the data stream or with respect to other data streams. By mapping and comparing data streams that exhibits some type of deviation, variability, or change, analysis system 180 may contextualize and correlate the data streams. This may be useful, for example, to identify the cause of a deviation, variability, or change in a data stream. As an example and not by way of limitation, an elevated heart-rate that coincides with increased activity is typically a normal response. However, a spike in heart-rate that coincides with a marginal elevated physical activity may not be a normal response. Analysis system 180 could then determine, based on the comparison, whether certain levels of activity produce abnormal heart-rate spikes in the user.

As an example and not by way of limitation, sensor array 110 may include a heart-rate sensor, a mood sensor 400 (for collecting subjective stress and behavior information) that is a smart phone, and a GPS system that is built into the smart phone. This system may be used to contextualize and correlate physiological, psychological, behavioral and environmental data streams to diagnose and monitor stress in a user. For example, the heart-rate sensor's data stream may show a spike in the user's heart-rate at certain times of the day or at certain locations. Similarly, mood sensor 400's data stream, when mapped against the heart-rate data, may show these time periods of increased heart-rate correlate to periods when the user indicated that his mood was "stressed" and his activity was "driving." If the user has previously been diagnoses as hypertensive, it may be desirable to avoid these particularly stressful driving situations that cause a spike in the user's heart-rate. These stressful driving situations may be identified by contextualizing the prior data streams against the GPS system's data stream. When the location data from the GPS system is mapped against the prior data streams, it may show the heart-rate spikes, stressed mood, and driving, all occurred at a specific highway interchange. Therefore, by contextualizing the physiological, psychological, behavioral, and environmental data streams, analysis system 180 may identify driving on the specific highway interchange as the cause of the user's heart-rate spikes. This could be useful, for example, to allow the user to identify situations to avoid (e.g., the specific highway interchange) and possibly to identify better or healthier alternatives (e.g., taking surface streets).

Diagnosis and Monitoring of Health States

In particular embodiments, one or more sensors 112 or one or more nodes 114 in sensor array 110 may continuously transmit data regarding a subject's health to analysis system 180, which may monitor and automatically detect changes in the subject's health state. As used herein, "health state" refers to a person's physiological and psychological state, including the person's state with respect to pathologies and diseases. By using an integrated sensor array 110 to monitor physiological, psychological, behavioral, and environmental data, analysis system 180 may identify pathologies, disease states, sensitivities, and other health-related states with greater accuracy than is possible with any individual sensor 112.

In particular embodiments, one or more sensors 112 in sensor array 110 may measure one or more biomarkers. A biomarker is a characteristic that can be measured and evaluated as an indicator of biological processes, pathogenic processes, or pharmacologic responses. As an example and not by way of limitation, in a pharmacogenomic context, a biomarker would be a specific genetic variation that correlates with drug response. As another example and not by way of limitation, in a neurochemical context, a biomarker would be a person's subjective stress level that correlates with the person's plasma glucocorticoid level. As yet another example and not by way of limitation, in a neuropsychological context, a biomarker would be a person's serotonin uptake rate that correlates with the person's depression level. As yet another example and not by way of limitation, in a biochemical context, a biomarker would be a person's LDL cholesterol level that correlates with the person's risk of heart disease, such as heart attack. A biomarker is effectively a surrogate for measuring another physiological or psychological characteristic. A biomarker may include any type of stimulus, including physiological, psychological, behavioral, or environmental stimulus.

In particular embodiments, analysis system 180 may identify pathologies, disease states, and other health states of a subject. Certain physiological, psychological, behavioral, or environmental data may correlate with certain pathologies, disease states, and other health states. As an example and not by way of limitation, analysis system 180 could determine whether a subject has hypertension by monitoring a blood-pressure data stream for a three-week period and identifying substantial periods where the subject's blood pressure is at least 140/90 mmHg, wherein these substantial periods of elevated blood pressure constitute hypertension. The accuracy of identification may generally be increased as the number of data streams is increased. Analysis system 180 may contextualize and correlate data from multiple data streams to eliminate confounders from its data analysis and reduce the likelihood of generating false-positive and false-negative disease-state diagnoses. As an example and not by way of limitation, the hypertension diagnosis system described above may generate a false-positive diagnosis of hypertension if the subject engages in lengthy periods of physical activity, which naturally raise the subject's blood pressure. Therefore, if analysis system 180 also monitored a heart-rate data stream of the subject, it could eliminate blood pressure data sets that correlate with time periods of high heart-rate, thereby reducing the likelihood of generating an incorrect hypertension diagnosis.

In particular embodiments, analysis system 180 may analyze physiological, psychological, behavioral, or environmental data steams to identify correlations between certain data sets and a subject's health state. As an example and not by way of limitation, analysis system 180 may be able to correlate a behavioral data set indicating the subject had a fight with a physiological data set indicating the subject had an elevated heart-rate to identify the fight as the cause of the elevated heart-rate. As another example and not by way of limitation, analysis system 180 may be able to correlate a physiological data set indicating the subject had an elevated skin-temperature with a behavioral data set indicating the subject was engaged in physical activity to identify the physical activity as the cause of the elevated skin-temperature. As yet another example and not by way of limitation, analysis system 180 may be able to correlate a psychological data set indicating the subject is depressed with an environmental data set indicating that the subject's stock portfolio substantially declined just prior to the onset of the subject's depression to identify the stock decline as the cause of the subject's depression. Analysis system 180 may use a variety of methods to identify correlations and generate causality hypotheses.

In particular embodiments, analysis system 180 may generate a model of a subject's health state. As an example and not by way of limitation, analysis system 180 may generate a baseline model of the subject's physiological or psychological state by analyzing one or more data streams during a control period. Once the baseline model is established, analysis system 180 could then continuously monitor the subject and identify deviations, variability, or changes in the data streams as compared to the baseline model. As another example and not by way of limitation, analysis system 180 may generate a predictive model of the subject's physiological or psychological state by analyzing one or more data streams and generating one or more algorithms that fit the sensor measurements. Once the predictive model is established, analysis system 180 could then be used to predict future health states, anticipated or hypothetical sensor readings, and other aspects of a subject's physiology or psychology. Analysis system 180 may also update and refine the predictive model based on new data generated by sensor array 110.

In particular embodiments, analysis system 180 may monitor disease-state progression and other health state changes over time. As an example and not by way of limitation, analysis system 180 could continuously monitor a subject's blood pressure over time to determine whether the subject's hypertension is improving. Such monitoring may be used to identify trends and to generate alerts or predictions regarding possible health states. Similarly, analysis system 180 may also monitor data streams containing treatment or therapy information to determine whether the treatment or therapy is efficacious. As an example and not by way of limitation, analysis system 180 could monitor a subject's blood pressure over time to determine whether an ACE inhibitor treatment is affecting the subject's hypertension.

In particular embodiments, analysis system 180 may monitor and analyze various data streams from a group of people to identify novel pre-disease states or risk states. As an example and not by way of limitation, one or more sensor arrays 110 could monitor a plurality of subjects. As multiple subjects develop certain diseases, analysis system 180 could analyze data sets from these subjects prior their development of the disease. The analysis of these data sets could allow analysis system 180 to identify certain health states that correlate with some level of risk for developing the disease.

Stress Generally

Stress is a person's total response to environmental demands or pressures. Stress is a state which arises from an actual or perceived demand-capability imbalance in a person. It is a negative emotional experience accompanied by biochemical, physiological, and behavioral changes that are directed either toward altering the stressful event or accommodating it. Stress results from interactions between a person and the environment that are perceived as straining or exceeding the person's adaptive capacities and threatening their well-being. The causes of stress (i.e., stressors) may include any event or occurrence that a person considers a threat to his coping strategies or resources. Stress may cause a variety of physiological, psychological, or behavioral reactions in a person. As an example and not by way of limitation, stress may cause a person's body to release certain hormones and neurotransmitters, such as catecholamines and glucocorticoids.

Catecholamines are neurotransmitters in the sympathetic nervous system. Catecholamines are synthesized from tyrosine. They are also released into the blood during times of psychological or physiological stress. High catecholamine levels in blood are associated with stress. The major catecholamines are dopamine, norepinephrine (noradrenaline), and epinephrine (adrenaline). Catecholamines are synthesized in the brain and other neural tissue. Catecholamines are also produced by the adrenal glands and secreted into the blood. Norepinephrine and dopamine act as neuromodulators in the central nervous system and as hormones in the blood circulation. Norepinephrine is a neuromodulator of the peripheral sympathetic nervous system but is also present in the blood (mostly through "spillover" from the synapses of the sympathetic system). Catecholamines may cause general physiological changes that prepare the body for physical activity ("fight-or-flight" response). Some typical effects include increases in heart rate, blood pressure, blood glucose levels, and increased activity of the sympathetic nervous system. Some drugs, like tolcapone (a central COMT-inhibitor), raise the levels of all the catecholamines by blocking their degradation post-release.

Epinephrine is an important catecholamine that acts primarily on muscle, adipose tissue, and the liver. Epinephrine increases delivery of $O_2$ to muscle tissue by increasing heart rate and blood pressure, and dilating respiratory passages. Epinephrine increases production of glucose by activating glycogen phosphorylase and inactivating glycogen synthase, thus simulating gluconeogenesis in the liver. Epinephrine promotes the anaerobic breakdown of glycogen in skeletal muscle into lactate by fermentation, thus stimulating glycolytic ATP formation. The stimulation of glycolysis is accomplished by raising the concentration of fructose 2,6-bisphosphate, an allosteric activator of the glycolytic enzyme phosphofructokinase-1. Finally, epinephrine stimulates glucagon secretion and inhibits insulin secretion.

Glucocorticoids are a class of steroid hormones that bind to the glucocorticoid receptor. Glucocorticoids have many diverse (pleiotropic) effects, including potentially harmful effects. Glucocorticoids cause their effects by binding to the glucocorticoid receptor. The activated glucocorticoid receptor complex up-regulates the expression of anti-inflammatory proteins in the nucleus (a process known as transactivation) and represses the expression of pro-inflammatory proteins in the cytosol by preventing the translocation of other transcription factors from the cytosol into the nucleus (transrepression).

Cortisol (or hydrocortisone) is the most important human glucocorticoid. It is essential for life, and it regulates or supports a variety of important cardiovascular, metabolic, immunologic, and homeostatic functions. A variety of stressors (anxiety, fear, pain, hemorrhage, infections, low blood glucose, etc.) stimulate release of cortisol from the adrenal cortex. Cortisol acts on muscle, liver, and adipose tissue to supply the person with fuel for impending intense activity. Cortisol is a relatively slow-acting hormone that alters metabolism by changing the kinds and amounts of certain enzymes that are newly synthesized in its target cell, rather than by regulating existing enzyme molecules. In adipose tissue, cortisol stimulates the release of fatty acids from stored triacylglycerols. The fatty acids are exported to the blood to serve as fuel for various tissues, and the glycerol resulting from triacylglycerol breakdown is used for gluconeogenesis in the liver. Cortisol stimulates the breakdown of nonessential muscle proteins and the export of amino acids to the liver where they serve as precursors for gluconeogenesis. In the liver, cortisol promotes gluconeogenesis by stimulating synthesis of the key enzyme PEP carboxykinase; glucagon also has this effect, whereas insulin has the opposite effect. Glucose produced in this way is stored in the liver as glycogen, or exported immediately by tissues that need glucose for fuel. The net effect of these metabolic changes is to elevate blood glucose levels and to store glycogen to support the fight-or-flight response commonly associated with stress. Consequently, the effects of stress hormones, such as cortisol, may counterbalance those of insulin.

Symptoms of stress may be psychological, physiological, or behavioral. Symptoms include poor judgment, depression, anxiety, moodiness, irritability, agitation, loneliness, various muscle complaints, headaches, diarrhea or constipation, nausea, dizziness, chest pain, elevated heart-rate, irregular eating, irregular sleeping, social withdrawal, procrastination or neglect of responsibilities, drug and alcohol abuse, and other abnormal or irregular behaviors.

Measuring Stress

In particular embodiments, sensor network 100 may analyze physiological, psychological, behavioral, or environmental data streams to diagnose and monitor stress in a user. Sensor array 110 may intermittently or continuously transmit physiological, psychological, behavioral, or environmental data streams to analysis system 180. Analysis system 180 may analyze one or more of these data streams to determine the stress index of the user. Any combination of two or more sensors may be used to generate a stress index value. These stress index values may be improved and calibrated by monitoring a person over time to determine when a change in physiological state is due to stress or due to a non-stress related event (such as, for example, exercise, dehydration). The stress-induced physiological changes may be used to establish a baseline physiological state for a person and a range of physiological variation associated with stress. A person may also engage in a training or control period during which the person's input or feedback may be used to engage machine-learning algorithms to develop a stress model that allows the person's stress index to be calculated. Similarly, machine learning may be used to correlate physiological stress responses with changes in psychological, behavioral, or environmental state.

In particular embodiments, analysis system 180 may access physiological, psychological, behavioral, or environmental data previously generated to compare it to current physiological, psychological, behavioral, or environmental data. Analysis system 180 may also access a stress index previously determined to compare it to a current stress index. Based on the comparison, analysis system 180 may then determine whether the user's stress level has changed over time. Analysis system 180 may also model the stress level with respect to time and identify any trends in the stress level of the user. Based on these changes and trends in stress level, various alerts or warnings may be provided to the user or to a third-party (e.g., the user's physician).

Analysis system 180 may use a variety of scales, both qualitative and quantitative, for assessing the stress level in a person. The stress level of a person may be quantified using a stress index, which may be any suitable scale for measuring or valuing stress. Analysis system 180 may quantify stress by combining data from multiple sensors 112. The simplest approach would be to assign a single numerical value, i.e., a stress index. Further refinements could be developed, such as, for example, a transient stress index, a stress load, a stress-resilience coefficient, or other suitable stress measurements. As an example and not by way of limitation, analysis system 180 could grade the stress level of a person on a 0-to-4 Liker scale, where the five-level Likert item may be:
  0. Very unstressed
  1. Moderately unstressed
  2. Neither stressed nor unstressed 3. Moderately stressed
4. Very stressed Other suitable Likert items may be used. The Likert items may be analyzed as interval-level data or as ordered-categorical data. As another example and not by way of limitation, analysis system 180 could grade the stress level of a person on a scale of 0 to 100, where 0 is the user's baseline stress when relaxed and resting and 100 is the user's maximum stress. A stress index may be scaled on an absolute scale or scaled on an individual scale. As an example and not by way of limitation, two users experiencing the same stress experience would report identical stress levels on an absolute stress index. However, two users experiencing the same stress experience may report different stress levels on individual stress indexes. A first user's baseline stress when relaxed may report a stress index of 0, which is different from a second user's baseline stress when relaxed and may also report a stress index of 0. Similarly, a first user may only have a minor stress response to a particular stress while a second user may have a major stress response to the same stressor. In particular embodiments, a stress index may be a multidimensional index. As an example and not by way of limitation, the stress index may quantify a person's transient stress (i.e., the change in stress caused by a stressor), baseline stress (i.e., the person's stress when in a normal state), and stress resilience (i.e., the rate at which a patient recovers from a stressor). In particular embodiments, a stress factor may be assigned to particular stressor or therapy. A stress factor is the change in a person's stress index associated with a particular stressor or therapy. As an example and not by way of limitation, driving in traffic may increase a person's stress index by 10 points on a 0-to-100 stress scale, while doing deep breathing exercises may decrease the person's stress index by 8 points. Although this disclosure describes particular stress indexes using particular scales for assessing the stress level in a person, this disclosure contemplates any suitable stress indexes using any suitable scales for assessing the stress level in a person.

Stress may be measured using a variety of methods. As an example and not by way of limitation, stress may be measured by analyzing heart-rate variability, stress-related analytes, and self-reported subjective stress.

Stress may be measured by accessing data from a heat-rate monitor and analyzing heart-rate variability. Heart-rate variability is typically measured using a pulse oximeter, which may measure the heart rate and blood oxygenation levels of a person. The basic technique of quantifying stress by using heart-rate variability and associating different frequency bands with activation of the sympathetic and parasympathetic systems comes from work in the 1980's (e.g., Pagani et al., 1986). By creating a ratio of the two frequency bands, a quantitative measure ("sympathovagal balance" (Pagani et al., 1986; Bigger et al., 1992)) comparing the relative activations is created, which the literature represents as the stress level of the person. This idea is refined to be more robust to signal noise and is described more fully in later literature (Albrecht & Cohen, 1988; Rottman et al., 1990; Bigger et al., 1992). Parati et al. (1995) provides a survey of spectral analysis applied to HRV and blood pressure variability. They include some reasoning for the choice of HF (parasympathetic control) being defined as frequencies above 0.15 Hz. and LF (sympathetic control) being defined as frequencies below 0.15 Hz (but likely above 0.07 Hz). They also note that these measures incompletely account for the actions of the sympathetic and parasympathetic systems, so that the ratio measure give a value that we associate with high stress but is actually due to some other phenomenon. A detailed discussion of the difficulty in measuring heart-rate variability can be found in Clifford (2002).

Stress may also be measured by accessing data from a biosensor and analyzing stress-related analyte levels, such as glucocorticoid and catecholamine levels. Various means may be used to measure glucocorticoid and catecholamine levels, including immunoassays and various chromatography techniques. The biosensors may measure and transmit information regarding the user's analyte levels. Analysis system 180 may then analyze this analyte data by inputting it into a stress model that correlates stress-related analyte levels with stress to calculate the user's stress index.

Stress may also be measured by accessing self-reported stress information, such as, for example, from one or more user-input sensors that may receive information on a user's subjective experience of stress. A user's psychological stress may be a biomarker for the user's physiological stress response. The user's subjective experience of stress may be used to indirectly measure the user's physiological stress, for example, by correlating the user's subjective experience of stress with the user's glucocorticoid level. The user-input sensor may measure and transmit information regarding the user's psychological stress levels. Analysis system 180 may then analyze this psychological data by inputting it into a stress model that correlates psychological stress levels with stress to calculate the user's stress index.

Although this disclosure describes particular methods for measuring stress, this disclosure contemplates any suitable methods for measuring stress. As an example and not by way of limitation, stress may be measured using any suitable data streams from physiological, psychological, behavioral, or environmental sensors.

Creating a Personalized Stress Profile Using Renal Doppler Sonography

Measuring and monitoring stress is a major challenge for present devices. The physiological response to stress may vary from person to person in type as well as extent. This causes a problem in creating a generalized method for measuring and monitoring stress in humans. The major changes during stress are observed in the sympathetic nervous system. The sympathetic nervous system is responsible for up- and down-regulating many homeostatic mechanisms in living organisms. Fibers from the sympathetic nervous system innervate tissues in almost every organ system, providing at least some regulatory function to things as diverse as pupil diameter, gut motility, and urinary output. It is perhaps best known for mediating the neuronal and hormonal stress response. Therefore, one method of measuring stress may involve measuring and monitoring the response of sympathetic nerves, such as in the kidney, where such nerves are rich.

The kidneys serve essential regulatory roles in most animals, including vertebrates and some invertebrates. They are essential in the urinary system and also serve homeostatic functions (such as, for example, the regulation of electrolytes, maintenance of acid-base balance, and regulation of blood pressure). The kidneys serve the body as a natural filter of the blood, and remove wastes which are diverted to the urinary bladder. In producing urine, the kidneys excrete wastes such as urea and ammonium; the kidneys also are responsible for the reabsorption of water, glucose, and amino acids. The kidneys also produce hormones including calcitriol, renin, and erythropoietin. Located at the rear of the abdominal cavity in the retroperitoneum, the kidneys receive blood from the paired renal arteries, and drain into the paired renal veins.

Each kidney excretes urine into a ureter, itself a paired structure that empties into the urinary bladder.

The kidney participates in whole-body homeostasis by regulating acid-base balance, electrolyte concentrations, extracellular fluid volume, and blood pressure. The kidney accomplishes these homeostatic functions both independently and in concert with other organs (i.e., both extra-renal and intra-renal mechanisms), particularly those of the endocrine system. Various endocrine hormones coordinate these endocrine functions, such as, for example, renin, angiotensin II, aldosterone, antidiuretic hormone, and atrial natriuretic peptide.

Many of the kidney's functions are accomplished by relatively simple mechanisms of filtration, reabsorption, and secretion, which take place in the nephron. Filtration, which takes place at the renal corpuscle, is the process by which cells and large proteins are filtered from the blood to make an ultrafiltrate that eventually becomes urine. The typical human kidney generates 180 liters of filtrate a day, while reabsorbing a large percentage, allowing for only the generation of approximately 2 liters of urine. Reabsorption is the transport of molecules from this ultrafiltrate and into the blood. Secretion is the reverse process, in which molecules are transported in the opposite direction, from the blood into the urine.

The sympathetic nervous system is an integral part of the homeostatic control system that maintains normal kidney function, with an extensive network of nerves identified in most renal tissues. The sympathetic nervous system modulates short-term regulation of renal function, and under normal conditions renal sympathetic nerve activity is low. During acute stress, however, elevated renal sympathetic activity depresses renal function. Chronic stress studies have been less conclusive and are difficult to design due to additional pathologies induced by stress, such as hypertension and cardiovascular complications. Major renal effects of mental stress include increased renal vasoconstriction, causing greater renal vascular resistance (RVR), and increased $Na^+$ transport, causing greater $Na^+$ retention. Both of these effects may contribute to the development of hypertension, and some investigators propose that this may be the primary mechanism of hypertension. Therefore, most studies on the renal effects of stress have focused on its relationship to hypertension. Though the effects of stress are more pronounced in hypertensive subjects, stress increases renal vasoconstriction and $Na^+$ retention in normal subjects as well.

The systemic blood pressure determines the renal perfusion pressure (RPP) and is a major determinant of renal vascular resistance. The kidney has a unique ability to efficiently auto-regulate its own blood flow over a wide range of renal perfusion pressures. Renal blood flow (RBF) changes very little over a large range of renal perfusion pressures, thus helping to maintain a stable renal vascular resistance. This is due to the fine control of vascular tone in the primary renal resistance vessels, the pre-glomerular afferent arterioles, and the post-glomerular efferent arterioles. However, many hormonal and neural disturbances can alter auto-regulation, often targeting these arterioles, leading to inappropriate increases in renal vascular resistance. Increased sympathetic activity increases arteriolar resistance and renal vascular resistance. Increased renal vascular resistance exacerbates hypertension via its contribution to overall increased total peripheral resistance (since renal blood flow is 20-25% of cardiac output) and its ability to promote $Na^+$ reabsorption. Stress can induce both neural and hormonal changes that affect renal vascular resistance.

Renal blood flow correlates with stress and therefore changes in renal blood flow may be significant indicators of stress. A user's stress level may be determined from renal blood flow information. Changes in a person's renal resistive index or renal vascular resistance may be used to detect the person's physiological or psychological responses to stress. As an example and not by way of limitation, a higher renal resistive index (renal RI) corresponds to a higher stress level. Similarly, a lower renal RI corresponds to a lower stress level (i.e., a relaxed state). Renal blood flow information may then be used to generate or validate stress models. Doppler sonography (pulse or continuous) may be used to measure the renal arterial blood flow. A renal Doppler sonograph may also include information about the peak blood pulse. The pulse peak can be used along with electrocardiograph information to measure pulse wave transit time, which can be used to measure renal blood pressure. Analysis system 180 may then use the renal blood flow information to measure and monitor stress in the person.

In particular embodiments, analysis system 180 may access one or more data streams from a renal Doppler sonograph and one or more physiological, psychological, behavioral, or environmental sensors to measure and model stress in a person. The data streams may comprise renal-Doppler data of the person, physiological data of the person, psychological data of the person, behavioral of the person, or environmental data, respectively. The renal-Doppler data may be renal-blood-velocity data, renal-blood-flow data, renal-resistive-index, renal-vascular-resistance, or other data generated or calculated by the renal Doppler sonograph. In particular embodiments, analysis system 180 may access data streams from a renal Doppler sonograph and one or more of a heart-rate monitor, a blood-pressure monitor, a pulse oximeter, or mood sensor. Although this disclosure describes accessing particular sensors 112 and particular data streams to measure and model stress in a person, this disclosure contemplates accessing any suitable sensors 112 and any suitable data streams to measure and model stress in a person.

In particular embodiments, analysis system 180 may generate a stress model of a person based on data streams from a renal Doppler sonograph and one or more physiological, psychological, behavioral, or environmental sensors. As an example and not by way of limitation, a stress model may be an algorithm based on renal-Doppler data of the person, heart-rate data of the person, blood-pressure data of the person, pulse-oximetry data of the person, or mood data of the person. The data the stress model is based on may be baseline data collected from the person during a control period. During the control period, the following variables may be controlled: the user's environment; the stressors and therapies the person is exposed to; and the sampling rate of the renal Doppler sonograph and other sensors 112, and other suitable variables. Stress may be induced by exposing a person to particular stressors, such as, for example, questionnaires, self-induced methodologies, media, personal interactions, or other suitable stressors. This baseline data may then be correlated with the stress index of the person. The stress model may include a variety of variables, such as, for example, renal blood-velocity, renal blood-flow, heart rate, blood pressure, blood-oxygen level, stress level, or one or more fixed variables. In particular embodiments, analysis system 180 may generate a model by fitting one or more data sets to a mathematical function. As an example and not by way of limitation, a stress model could be an algorithm based on sensor measurements made by one or more sensors 112 over some control period. The stress model may include a variety of variables, including data from one or more data streams and one or more fixed variables. The following is an example algorithm that analysis system 180 could generate to model the stress of a person:

$$f_{sm} = f(D_{RBV}^1, D_{HR}^2, D_{BP}^3, D_{SpO2}^4, D_{mood}^5, X^1, \ldots, X^M)$$

where:
$f_{sm}$ is the stress model of the person,
$(D_{RBV}^1)$ is the renal blood-velocity of the person,
$(D_{HR}^2)$ is the heart rate of the person,
$(D_{BP}^3)$ is the blood pressure of the person,
$(D_{SpO2}^4)$ is the blood-oxygen level of the person,
$(D_{mood}^5)$ is the self-reported stress level of the person, and
$(X^1, \ldots, X^M)$ are fixed variables 1 through M.

In particular embodiments, the stress model may be used to calculate a stress index of the person. As an example and not by way of limitation, the stress model of the person may directly calculate the stress index of the person, such that $f_{sm}$=SI, where SI is the stress index of the person. As another example and not by way of limitation, the stress index of the person may be based on the stress model of the person, such that $f(f_{sm})$=SI. In particular embodiments, the stress index of a person may equal the self-reported stress level of the person, such that $D_{mood}^5$=SI. Given renal blood-velocity data, a correlation between self-reported stress of a person and the renal blood-velocity of the person can be determined. Correlations between self-reported stress and other physiological parameters may also be determined, allowing the stress model to be reformulated such that $D_{mood}^5 = f(D_{RBV}^1, D_{HR}^2, D_{BP}^3, D_{SpO2}^4, X^1, \ldots, X^M)$. Analysis system 180 may also update and refine the stress model based on new physiological, psychological, behavioral, or environmental generated by sensor array 110. In particular embodiment, the stress model may be used to determine the user's physiological and psychological state. As an example and not by way of limitation, the stress model of the person may be used to calculate the heart rate and blood pressure of a person given the renal blood-velocity of the person. Although this disclosure describes particular components performing particular processes to generate a stress model of a person, this disclosure contemplates any suitable components performing any suitable processes to generate a stress model of a person. Moreover, although this disclosure describes particular stress models based on particular data or variables, this disclosure contemplates any suitable stress models based on any suitable data or variables. Furthermore, although this disclosure describes particular relationships between the stress model of a person and the stress index of the person, this disclosure contemplates any suitable relationship between the stress model of a person and the stress index of the person.

In particular embodiments, analysis system 180 may access a plurality of data sets from the data streams to measure and model stress. A typical diagnostic test involves generating at least two data sets, wherein the data sets are collect from the person when he is at different stress states. The data sets may include the person's renal-Doppler data and one or more data sets from one or more other sensors 112 in sensor array 110. As an example and not by way of limitation, a first data set of renal-Doppler data may be collected from the person when the person is exposed to a particular stressor, and a second data set of renal-Doppler data may be collected from the person when the person is not exposed to the particular stressor. As another example and not by way of limitation, a first data set of renal-Doppler data may be collected from the person when he is substantially unstressed, i.e., relaxed (such as, for example, when the person reports on mood sensor 400 that he is "stressed" with an intensity of 1 or less on a 0-to-4 Likert scale), establishing the person's baseline stress level, and a second data set of renal-Doppler data may be collected from the person when he is substantially stressed (such as, for example, when the person reports on mood sensor 400 that he is "stressed" with an intensity of 3 or more on a 0-to-4 Likert scale). Analysis system 180 may then determine how the person's renal-Doppler changes with stress. Analysis system 180 may also determine the stress factor associated with the particular stressor. The accuracy of the stress model may generally be increased as the number of data sets is increased. Therefore, multiple data sets may be generated and analyzed to model stress in a person. Typically, the data sets will be collected from the person when he is engaged in varying behaviors or subjected to varying stressors.

In particular embodiments, analysis system 180 may access a data stream from a behavioral sensor to measure and model stress in a person, wherein the data stream comprises behavioral data of the person. The behavioral sensor may be any suitable user-input sensor, such as, for example, mood sensor 400. The behavioral sensor may also be any suitable data feed, such as, for example, an electronic calendar. Analysis system 180 may then analyze the data stream containing the behavioral data of the person, allowing it to more accurately measure and model the stress of a person. Particular behaviors are associated with increases in stress. As an example and not by way of limitation, analysis system 180 could map behavioral data against stress data to determine whether particular activities correlate with changes in a person's stress index.

In particular embodiments, analysis system 180 may access a data stream from an electrocardiograph to measure and model stress in a person, wherein the data stream comprises electrocardiograph data of the person. Analysis system 180 may then analyze the data stream containing the electrocardiograph data of the person, allowing it to more accurately measure and model the stress of the person. Increases in heart rate are associated with increases in stress. As an example and not by way of limitation, analysis system 180 could map electrocardiograph data against stress data to determine whether particular changes in the ECG waveform correlated with changes in a person's stress index.

In particular embodiments, analysis system 180 may access a data stream from a glucocorticoid meter to measure and model stress in a person, wherein the data stream comprises glucocorticoid data of the person. The glucocorticoid meter may be a biosensor for measuring glucocorticoid levels, such as, for example, an immunoassay or chromatograph. The glucocorticoid meter may also be any suitable user-input sensor, such as, for example, mood sensor 400. The user-input sensor may receive subjective stress information from the person, which may serve as a biomarker for the user's glucocorticoid level. Analysis system 180 may then analyze the data stream containing the glucocorticoid data of the person, allowing it to more accurately measure and model the stress of the person. Increases in glucocorticoid levels are associated with increases in stress. As an example and not by way of limitation, analysis system 180 could map glucocorticoid data against stress data to determine whether particular changes in the glucocorticoid levels correlate with changes in a person's stress index.

In particular embodiments, analysis system 180 may access a data stream from a respiration sensor to measure and model stress in a person, wherein the data stream comprises respiration data of the person. Analysis system 180 may then analyze the data stream containing the respiration data of the person, allowing it to more accurately measure and model the stress of the person. Increases in respiration rate are associated with increases in stress. As an example and not by way of limitation, analysis system 180 could map respiration data against stress data to determine whether particular changes in the person's respiration rate correlated with changes in the person's stress index.

In particular embodiments, analysis system 180 may access a data stream from a galvanic-skin-response sensor to measure and model stress in a person, wherein the data stream comprises galvanic-skin-response data of the person. Galvanic skin response is also known as electrodermal response, psychogalvanic reflex, or skin conductance response. A galvanic-skin-response sensor can measure the autonomic nerve response as a parameter of the sweat gland function by measuring the electrical resistance of the skin. As stress levels increase, changes in the electrical resistance of the skin are detected by GSR sensors, with increase in resistance being associated with increases in stress. As an example and not by way of limitation, analysis system 180 could map galvanic-skin-response data against stress data to determine whether particular changes in the person's galvanic skin-response correlated with changes in the person's stress index.

FIG. 9 illustrates an example method 900 for creating a stress profile using renal Doppler sonography. The method begins at step 910, where analysis system 180 may access one or more data streams from a plurality of sensors 112. The sensors 112 may comprise a renal Doppler sonograph and one or more of a heart-rate monitor, a pulse oximeter, or a mood sensor. The data streams may comprise renal-Doppler data of a person from the renal Doppler sonograph and one or more heart-rate data of the person from the heart-rate monitor, blood-pressure data of the person from the blood-pressure monitor, pulse-oximetry data of the person from the pulse oximeter, or mood data of the person from the mood sensor. At step 920, analysis system 180 may generate a stress model of the person based on the data streams. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates particular components carrying out particular steps of the method of FIG. 9, this disclosure contemplates any suitable combination of any suitable components carrying out any suitable steps of the method of FIG. 9.

Continuous Monitoring of Stress Using a Stress Profile Created by Renal Doppler Sonography As discussed previously, stress may be measured using a variety of methods. However measuring and monitoring stress using these methods may be difficult because different persons may respond to stress differently. Furthermore, a person may undergo a variety of physiological and psychological changes due to a variety of disparate reasons, including stress. Consequently, it may be difficult to make a precise determination of stress based on a sensor reading alone. A stress profile of a person that accounts for a variety of physiological, psychological, behavioral, and environmental factors may be needed to accurately measure stress levels in a person.

In particular embodiments, analysis system 180 may access one or more data streams from one or more physiological, psychological, behavioral, or environmental sensors to measure and monitor stress in a person. The data streams may comprise physiological data of the person, psychological data of the person, behavioral of the person, or environmental data, respectively. In particular embodiments, analysis system 180 may access data streams from one or more of a heart-rate monitor, a blood-pressure monitor, a pulse oximeter, a mood sensor, or an accelerometer. Although this disclosure describes accessing particular sensors 112 and particular data streams to measure and monitor stress in a person, this disclosure contemplates accessing any suitable sensors 112 and any suitable data streams to measure and monitor stress in a person.

In particular embodiments, analysis system 180 may access a stress model. As an example and not by way of limitation, a stress model may be an algorithm based on renal-Doppler data, heart-rate data, blood-pressure data, pulse-oximetry data, or mood data. As an example and not by way of limitation, a stress model could be an algorithm based on sensor measurements made by one or more sensors 112 over some control period. The stress model may include a variety of variables, including data from one or more data streams and one or more fixed variables. The following is an example algorithm that analysis system 180 could access that models the stress of a person:

$$f_{sm} = f(D_{HR}^1, D_{BP}^2, D_{SpO2}^3, D_{mood}^4, D_{acc}^5, X^1, \ldots, X^M)$$

where:
$f_{sm}$ is the stress model,
$(D_{HR}^1)$ is the heart rate of the person,
$(DB_{BP}^2)$ is the blood pressure of the person,
$(D_{SpO2}^3)$ is the blood-oxygen level of the person,
$(D_{mood}^4)$ is the self-reported stress level of the person,
$(D_{acc}^5)$ is the activity (acceleration) of the person, and
$(X^1, \ldots, X^M)$ are fixed variables 1 through M.

Although this disclosure describes accessing particular stress models based on particular data or variables, this disclosure contemplates accessing any suitable stress models based on any suitable data or variables.

The stress model may be a stress model based on baseline data from one or more persons. In particular embodiments, the stress model may be a stress model of a person who is the subject of sensor array 110. That is to say that analysis system 180 may currently be measuring and monitoring stress in a first person and the stress model may be based on baseline data of the first person. This stress model of the person may be based on baseline data collected from the person during a control period. In particular embodiments, the stress model may be a stress model of one or more persons who are not currently the subject of sensor array 110. That is to say that analysis system 180 may currently be measuring and monitoring stress in a first person and the stress model may be based on baseline data of one or more second persons. This stress model of the one or more second persons may be based on baseline data collected from the second persons during a control period. Generating and using a stress model of one or more second persons may allow stress to be accurately measured in the first person without having to generate a personalized stress profile for the first person, which may be expensive and time-consuming. The first person and the one or more second persons may be in the same subset of patients, patient group, or patient cohort. As an example and not by way of limitation, the first person and the second persons may be in the same age group, ethnic group, racial group, patient population, or another suitable category of persons. As another example and not by way of limitation, the patients may be part of the same medically plausible subset of the patient population for a common disease or condition. Medically plausible subsets generally include groups of patients with special requirements or characteristics that distinguish them from the larger disease grouping. A medically plausible subset may be a patient subpopulation that demonstrates unique pharmacological or pharmacodynamic characteristics. The term patient, as used herein, may refer to any person and is not limited to a person who is receiving medical attention, care, or treatment. Although this disclosure describes stress models based on particular persons or groups of persons, this disclosure contemplates stress models based on any suitable persons or groups of persons.

In particular embodiments, analysis system 180 may analyze the data streams with respect to the stress model. Analysis system 180 may use any suitable process, calculation, or technique to analyze the data streams with respect to the stress model. As an example and not by way of limitation, analysis system 180 may analyze the stress model to identify independent variables that correspond to particular data streams. Analysis system 180 may then analyze the data streams and identify data points or data ranges from the data streams that may be used as inputs into the stress model. Although this disclosure describes particular components performing particular processes to analyze the data streams with respect to the stress model, this disclosure contemplates any suitable components performing any suitable processes to analyze the data streams with respect to the stress model.

In particular embodiments, analysis system 180 may determine the current stress index of a person. The stress model may be used to calculate a stress index of the person. As an example and not by way of limitation, the stress model may directly calculate the stress index of the person, such that $f_{sm}$=SI, where SI is the stress index of the person. As another example and not by way of limitation, the stress index of the person may be based on the stress model, such that $f(f_{sm})$=SI. Analysis system 180 may calculate the stress index of the person based on the data from one or more of the data streams. As an example and not by way of limitation, analysis system 180 may input data points or data ranges from the data streams into the stress model as independent variables. Analysis system 180 may then calculate the stress index of the person by solving the stress model. Although this disclosure describes particular components performing particular processes to determine the current stress index of a person, this disclosure contemplates any suitable components performing any suitable processes to determine the current stress index of a person. Moreover, although this disclosure describes particular relationships between the stress model of a person and the stress index of the person, this disclosure contemplates any suitable relationship between the stress model of a person and the stress index of the person.

In particular embodiments, analysis system 180 may access a plurality of data sets from the data streams to measure and monitor stress. A typical diagnostic test involves generating at least two data sets, wherein the data sets are collect from the person when he is at different stress states. The data sets may include one or more data sets from one or more sensors 112 in sensor array 110. As an example and not by way of limitation, a first data set may be collected from the person when the person is exposed to a particular stressor, and a second data set may be collected from the person when the person is not exposed to the particular stressor. As another example and not by way of limitation, a first data set may be collected from the person when he is substantially unstressed, i.e., relaxed (such as, for example, when the person reports on mood sensor 400 that he is "stressed" with an intensity of 1 or less on a 0-to-4 Likert scale), establishing the person's baseline stress level, and a second data set may be collected from the person when he is substantially stressed (such as, for example, when the person reports on mood sensor 400 that he is "stressed" with an intensity of 3 or more on a 0-to-4 Likert scale). Analysis system 180 may then determine how the person's physiological or psychological states change with stress. Analysis system 180 may also determine the stress factor associated with the particular stressor. The accuracy of determining stress in a person may generally be increased as the number of data sets is increased. Therefore, multiple data sets may be generated and analyzed to determine stress in a person. Typically, the data sets will be collected from the person when he is engaged in varying behaviors or subjected to varying stressors.

In particular embodiments, analysis system 180 may access the stress index history of a person to determine if the stress index of the person has changed over time. As an example and not by way of limitation, analysis system 180 may access a stress index of the person that was previously determined. Analysis system 180 may then analyze the prior stress index and compare it to one or more subsequently determined stress indexes to determine whether the stress index has changed with respect to the previously determined stress index. Analysis system 180 may determine whether there are any trends in the person's stress index over time or with respect to one or more physiological, psychological, behavioral, or environmental data streams. For example, analysis system 180 could map the person's blood pressure over time against the person's stress index over time to determine whether there are any correlating trends between the two data sets (e.g., the user's blood pressure and stress are both trending up with time). Although this disclosure describes particular components performing particular processes to determine if the stress index of a person has changed over time, this disclosure contemplates any suitable components performing any suitable processes to determine if the stress index of a person has changed over time.

In particular embodiments, analysis system 180 may access a data stream from a behavioral sensor to measure and monitor stress in a person, wherein the data stream comprises behavioral data of the person. The behavioral sensor may be any suitable user-input sensor, such as, for example, mood sensor 400. The behavioral sensor may also be any suitable data feed, such as, for example, an electronic calendar. Analysis system 180 may then analyze the data stream containing the behavioral data of the person, allowing it to more accurately measure and monitor the stress of a person. Particular behaviors are associated with increases in stress. As an example and not by way of limitation, analysis system 180 could map behavioral data against physiological data to determine whether particular physiological changes are caused by particular activities or by stress.

In particular embodiments, analysis system 180 may access a data stream from an electrocardiograph to measure and monitor stress in a person, wherein the data stream comprises electrocardiograph data of the person. Analysis system 180 may then analyze the data stream containing the electrocardiograph data of the person, allowing it to more accurately measure and monitor the stress of the person. Increases in heart rate are associated with increases in stress. As an example and not by way of limitation, analysis system 180 could map electrocardiograph data against other physiological data to determine whether particular physiological changes are caused by changes in the ECG waveform or by stress.

In particular embodiments, analysis system 180 may access a data stream from a glucocorticoid meter to measure and monitor stress in a person, wherein the data stream comprises glucocorticoid data of the person. The glucocorticoid meter may be a biosensor for measuring glucocorticoid levels, such as, for example, an immunoassay or chromatograph. The glucocorticoid meter may also be any suitable user-input sensor, such as, for example, mood sensor 400. The user-input sensor may receive subjective stress information from the person, which may serve as a biomarker for the user's glucocorticoid level. Analysis system 180 may then analyze the data stream containing the glucocorticoid data of the person, allowing it to more accurately measure and monitor the stress of the person. Increases in glucocorticoid levels are associated with increases in stress. As an example and not by way of limitation, analysis system 180 could map glucocorticoid data against other physiological data to determine whether particular physiological changes are caused by changes in glucocorticoid levels or by stress.

In particular embodiments, analysis system 180 may access a data stream from an electromyograph to measure and monitor stress in a person, wherein the data stream comprises electromyograph data of the person. Analysis system 180 may then analyze the data stream containing the electromyograph data of the person, allowing it to more accurately measure and monitor the stress of the person. As an example and not by way of limitation, analysis system 180 could map electromyograph data against other physiological data to determine whether particular physiological changes are caused by particular muscle activity or by stress.

In particular embodiments, analysis system 180 may access a data stream from a respiration sensor to measure and model stress in a person, wherein the data stream comprises respiration data of the person. Analysis system 180 may then analyze the data stream containing the respiration data of the person, allowing it to more accurately measure and model the stress of the person. Increases in respiration rate are associated with increases in stress. As an example and not by way of limitation, analysis system 180 could map respiration data against other physiological data to determine whether particular physiological changes are caused by changes in the person's respiration rate.

In particular embodiments, analysis system 180 may access a data stream from a galvanic-skin-response sensor to measure and model stress in a person, wherein the data stream comprises galvanic-skin-response data of the person. Galvanic skin response is also known as electrodermal response, psychogalvanic reflex, or skin conductance response. A galvanic-skin-response sensor can measure the autonomic nerve response as a parameter of the sweat gland function by measuring the electrical resistance of the skin. As stress levels increase, changes in the electrical resistance of the skin are detected by GSR sensors, with increase in resistance being associated with increases in stress. As an example and not by way of limitation, analysis system 180 could map galvanic-skin-response data against other physiological data to determine whether particular physiological changes are caused by changes in the person's galvanic skin-response.

FIG. 10 illustrates an example method 1000 for monitoring stress using a stress profile created by renal Doppler sonography. The method begins at step 1010, where analysis system 180 may access one or more data streams from a plurality of sensors 112. The sensors 112 may comprise one or more of a heart-rate monitor, a blood-pressure monitor, a pulse oximeter, a mood sensor, or an accelerometer. The data streams may comprise one or more of heart-rate data of a person from the heart-rate monitor, blood-pressure data of the person from the blood-pressure monitor, pulse oximetry data of the person from the pulse oximeter, mood data of the person from the mood sensor, or accelerometer data of the person from the accelerometer. At step 1020, analysis system 180 may access a stress model. The stress model may comprise baseline renal-Doppler data and two or more of baseline heart-rate data, baseline blood-pressure data, baseline pulse oximetry data, or baseline mood data. At step 1030, analysis system 180 may analyze the data streams with respect to the stress model. At step 1040, analysis system 180 may determine based on the analysis a current stress index of the person. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates particular components carrying out particular steps of the method of FIG. 10, this disclosure contemplates any suitable combination of any suitable components carrying out any suitable steps of the method of FIG. 10.

Continuous Monitoring of Stress Using Self-Reported Psychological or Behavioral Data One problem in measuring and monitoring stress accurately is determining whether any changes in measured parameters are taking place due to non-stress related activity from the user that confound the analysis (i.e., confounding factors). Various physiological sensors may be used in an attempt to measure stress, such as, for example, heart-rate monitors, blood-pressure monitors, pulse oximeters, or respiration sensors. However, physiological changes that correlate with stress may actually be caused by non-stress events. For example, an increase in heart rate is associated with an increase in stress, but it is also associated with exercise, which may in fact cause a decrease in stress. Similarly, physiological or psychological data indicating stress may be due to confounding factors and may in fact be contradicted by a patient's self-reported non-stressed state. By using a mood sensor or behavioral sensor, such as mood sensor 400, a patient may input psychological data (e.g., happy, anxious, sad, stressed) or behavioral data (e.g., running, driving, fighting, working) By contextualizing physiological sensor data with this psychological or behavioral data, analysis system 180 may be able to eliminate changes in physiological data caused by non-stress related events and thereby more accurately measure and monitor stress in a person.

In particular embodiments, analysis system 180 may measure and monitor stress by analyzing one or more data streams from one or more mood sensors, such as, for example, mood sensor 400. A user may input psychological (i.e., mood) information into mood sensor 400. A mood sensor may receive information regarding a user's subjective experience of stress. A user's subjective experience of stress may act as a biomarker for various physiological states, including, for example, the user's glucocorticoid and catecholamine levels. The user may input stress, for example, on mood input widget 430. The user could then input an intensity of the stress, for example, on mood intensity widget 440. After receiving the user's mood information, the mood sensor may then transmit one or more data streams comprising the user's mood data to analysis system 180. As an example and not by way of limitation, a user may report mood information by inputting that he is "stressed" with an intensity of 2 on a 0-to-4 Likert scale using mood input widget 430 and mood intensity widget 440. A mood sensor may also receive information regarding a user's general psychological state, which may correlate with stress. As an example and not by way of limitation, a user may report mood information by inputting that he is "angry" with an intensity of 3 on a 0-to-4 Likert scale. Analysis system 180 may then analyze this mood and mood intensity data by inputting it into a stress model that correlates psychological states with stress to calculate the user's stress index. Analysis system 180 may continuously monitor a data stream containing psychological data, thereby allowing it to accurately measure and monitor a user's stress and stress-related health states. Although this disclosure describes measuring and monitoring stress using particular types of mood sensors, this disclosure contemplates measuring and monitoring stress using any suitable mood sensors.

In particular embodiments, analysis system 180 may measure and monitor stress by analyzing one or more data streams from one or more behavioral sensors, such as, for example, mood sensor 400. A user's behavior information may be correlated with other stress-related data. A user may input behavioral (i.e., activity) information into mood sensor 400. The user may input a behavior, for example, on activity input widget 450. After receiving the user's behavioral information, the behavioral sensor may then transmit one or more data streams comprising the user's behavioral data to analysis system 180. As an example and not by way of limitation, a user may report behavioral data by inputting that he is "driving" using activity input widget 450. Analysis system 180 may then analyze this behavioral data by inputting it into a stress model that correlates behavioral states with stress to calculate the user's stress index. Alternatively, analysis system 180 may calculate the user's stress index using other factors and then correlate a user's stress with specific behaviors by the user. Similarly, analysis system 180 may correlate a user's lack of stress (i.e., relaxation) with specific behavior or activities by the user. Analysis system 180 may continuously monitor a data stream containing behavioral data, thereby allowing it to accurately measure and monitor a user's stress and stress-related health states. Although this disclosure describes diagnosing and monitoring stress using particular types of behavioral sensors, this disclosure contemplates diagnosing and monitoring stress using any suitable types of behavioral sensors. As an example and not by way of limitation, an electronic calendar may be a behavioral sensor, wherein calendar entries may describe a person's behavior at particular times. Analysis system 180 may then access a data stream from the electronic calendar with this behavioral data.

In particular embodiments, analysis system 180 may access a psychological or behavioral data stream and one or more physiological data streams to measure and monitor stress in a person. The data streams may comprise psychological data of the person, behavioral of the person, or physiological data of the person, respectively. In particular embodiments, analysis system 180 may access data streams from a mood sensor or behavioral sensors and one or more of a heart-rate monitor, a blood-pressure monitor, a pulse oximeter, or an accelerometer. Although this disclosure describes accessing particular sensors 112 and particular data streams to measure and monitor stress in a person, this disclosure contemplates accessing any suitable sensors 112 and any suitable data streams to measure and monitor stress in a person.

In particular embodiments, analysis system 180 may access a plurality of data sets from the data streams to measure and monitor stress in a person. A typical diagnostic test involves generating at least two data sets, wherein the data sets are collect from the person when he is at different psychological or behavioral states. The data sets may include one or more data sets from one or more sensors 112 in sensor array 110. As an example and not by way of limitation, a first data set may be collected from the person when the person is in a first mood (e.g., stressed), and a second data set may be collect from the person when the person is in a second mood (e.g., unstressed). As another example and not by way of limitation, a first data set may be collected from the person when the person is engaged in a first activity (e.g., sleeping), and a second data set may be collected from the person when the person is engaged in a second activity (e.g., exercising). As yet another example and not by way of limitation, a first data set may be collected from the person when the person is exposed to a particular stressor (e.g., being asked to solve a difficult analytical problem), and a second data set may be collected from the person when the person is not exposed to the particular stressor. Analysis system 180 may then use the psychological or behavioral data to deconfound the physiological data to determine whether changes in the physiological state of a person are caused by stress or by a particular psychological or behavioral state. The accuracy of determining stress in a person may generally be increased as the number of data sets is increased. Therefore, multiple data sets may be generated and analyzed to determine stress in a person. Although this disclosure describes accessing particular data sets to measure and monitor stress in a person, this disclosure contemplates accessing any suitable data sets to measure and monitor stress in a person.

In particular embodiments, analysis system 180 may access a stress model of a person. As an example and not by way of limitation, a stress model may be an algorithm based on renal-blood-velocity data and mood or behavioral data and heart-rate data, blood-pressure data, pulse-oximetry data, or accelerometer data. As an example and not by way of limitation, a stress model could be an algorithm based on sensor measurements made by one or more sensors 112 over some control period. The stress model may include a variety of variables, including data from one or more data streams and one or more fixed variables. The following is an example algorithm that analysis system 180 could access that models the stress of a person:

$$f_{sm} = f(D_{mood}^1, D_{beh}^2, D_{HR}^3, D_{BP}^4, D_{SpO2}^5, D_{acc}^6, X^1, \ldots, X^M)$$

where:
$f_{sm}$ is the stress model,
$(D_{mood}^1)$ is the psychological state (mood) of the person,
$(D_{beh}^2)$ is the behavioral state (activity) of the person,
$(D_{HR}^3)$ is the heart rate of the person,
$(D_{BP}^4)$ is the blood pressure of the person,
$(D_{SpO2}^5)$ is the blood-oxygen level of the person,
$(D_{acc}^6)$ is the physical activity (acceleration) of the person, and
$(X^1, \ldots, X^M)$ are fixed variables 1 through M.

Although this disclosure describes accessing particular stress models based on particular data or variables, this disclosure contemplates accessing any suitable stress models based on any suitable data or variables.

In particular embodiments, analysis system 180 may analyze data sets from the psychological or behavioral data streams and the physiological data streams with respect to each other. Analysis system 180 may use any suitable process, calculation, or technique to analyze the data streams with respect to each other. As an example and not by way of limitation, analysis system 180 may compare the first data set and a second data to identify any changes in the physiological state of the person and to identify any corresponding changes in psychological or behavioral state. As another example and not by way of limitation, analysis system 180 may analyze the data streams and identify data points or data ranges from the data streams that may be used as inputs into a stress model. In particular embodiments, analysis system 180 may contextualize the physiological data with the psychological or behavioral data, such as, for example, by mapping the data with respect to each other. As an example and not by way of limitation, analysis system 180 may contextualize heart-rate data, blood-pressure data, pulse-oximetry data, and accelerometer data of the person with the mood data of the person, allowing analysis system 180 to identify correlations between changes in the physiological data and the mood data. Although this disclosure describes particular components performing particular processes to analyze the data streams with respect to each other, this disclosure contemplates any suitable components performing any suitable processes to analyze the data streams with respect to each other.

In particular embodiments, analysis system 180 may determine the current stress index of a person based on the analysis of a plurality of data sets from the psychological or behavioral data streams and the physiological data streams with respect to each other. The stress index may be determined both from the psychological or behavior state of the person and the physiological state of the person. Various psychological states may correlate with stress, such as, for example, stress, anger, anxiety, or depression. Other psychological states may correlate with a lack of stress, such as, for example, happiness or relaxation. Various behavioral states may correlate with stress, such as, for example, working, arguing, or driving. Other behavioral states may correlate with a lack of stress, such as, for example, socializing, relaxing, or exercising. Various physiological states may correlate with stress, such as, for example, increased heart rate, increased blood pressure, or decreased blood oxygen. As an example and not by way of limitation, analysis system 180 may examine the data streams and identify psychological, behavioral, or physiological states that correlate with stress or a lack of stress. Analysis system 180 may analyze one data set to determine the baseline stress of the person and then analyze another data set to determine the change in the person's psychological, behavioral, or physiological states to determine a current stress index of the person. Analysis system 180 may determine the current stress index of the person by determining the magnitude that each of the psychological, behavioral, or physiological states correlates with stress or lack of stress. As an example and not by way of limitation, a low blood pressure may correlate with a low stress index while a high blood pressure may correlate with a high stress index. As another example and not by way of limitation, a self-reported psychological state of "happy" with an intensity of 3 on a 0-to-4 Likert scale may correlate with a low stress index while a self-reported psychological state of "happy" with an intensity of 0 on a 0-to-4 Likert scale may correlate with a high stress index. As yet another example, a behavioral state of "relaxing" may correlate with a low stress index while a behavioral state of "arguing" may correlate with a high stress index. Although this disclosure describes particular components performing particular processes to determine the current stress index of a person, this disclosure contemplates any suitable components performing any suitable processes to determine the current stress index of a person. Moreover, although this disclosure describes analyzing particular data streams for particular correlations to determine the current stress index of a person, this disclosure contemplates analyzing any suitable data streams for any suitable correlations to determine the current stress index of a person.

In particular embodiments, analysis system 180 may use a stress model of a person to determine the current stress index of the person based on the analysis of data sets from the psychological or behavioral data streams and the physiological data streams with respect to each other. As an example and not by way of limitation, the stress model may directly calculate the stress index of the person, such that $f_{sm}$=SI, where SI is the stress index of the person. As another example and not by way of limitation, the stress index of the person may be based on the stress model, such that $f(f_{sm})$=SI. Analysis system 180 may calculate the stress index of the person based on the data from one or more of the psychological or behavioral data streams and the physiological data streams. As an example and not by way of limitation, analysis system 180 may input data points or data ranges from the psychological or behavioral data streams and the physiological data streams into the stress model as independent variables. Analysis system 180 may then calculate the stress index of the person by solving the stress model. Although this disclosure describes particular components performing particular processes to determine the current stress index of a person, this disclosure contemplates any suitable components performing any suitable processes to determine the current stress index of a person. Moreover, although this disclosure describes particular relationships between the stress model of a person and the stress index of the person, this disclosure contemplates any suitable relationship between the stress model of a person and the stress index of the person.

In particular embodiments, analysis system 180 may access one or more data streams from one or more additional sensors 112 to measure and monitor stress in a person. As described previously, analysis system 180 may access, for example, an electrocardiograph, a glucocorticoid meter, an electromyograph, a respiration sensor, a galvanic-skin-response sensor, or another suitable sensor 112. Analysis system 180 may then analyze these additional data streams, allowing it to more accurately measure and monitor the stress of the person, such as, for example, by deconfounding physiological data caused by non-stress related events.

FIG. 11 illustrates an example method 1100 for monitoring stress using psychological or behavioral data. The method begins at step 1110, where analysis system 180 accesses one or more data streams from a plurality of sensors 112. The sensors 112 may comprise a mood (psychological) sensor and one or more of a heart-rate monitor, a blood-pressure monitor, a pulse oximeter, or an accelerometer. The data streams may comprise mood (psychological) data of a person from the mood sensor and one or more of heart-rate data of the person from the heart-rate monitor, blood-pressure data of the person from the blood-pressure monitor, pulse oximetry data of the person from the pulse oximeter, or accelerometer data of the person from the accelerometer. A first data set from the data streams may be collected from the person at a first time and the person may be substantially stressed at the first time. A second data set from the data streams may be collected from the person at a second time and the person may be substantially unstressed at the second time. At step 1120, analysis system 180 may analyze the first data set and the second data set with respect to each other. At step 1130, analysis system 180 may determine a current stress index of the person based on the analysis of the first data set and the second data set with respect to each other. Although this disclosure describes and illustrates particular steps of the method of FIG. 11 as occurring in a particular order, this disclosure contemplates any suitable steps of the method of FIG. 11 occurring in any suitable order. Moreover, although this disclosure describes and illustrates particular components carrying out particular steps of the method of FIG. 11, this disclosure contemplates any suitable combination of any suitable components carrying out any suitable steps of the method of FIG. 11.

Continuous Monitoring of Stress Using Accelerometer Data

As discussed previously, one problem in measuring and monitoring stress accurately is determining whether any changes in measured parameters are taking place due to non-stress related activity (such as, for example, by the user) that confound the analysis. Various physiological sensors may be used in an attempt to measure stress, such as, for example, heart-rate monitors, blood-pressure monitors, pulse oximeters, or respiration sensors. However, physiological changes that correlate with stress may actually be caused by non-stress events. For example, increases in heart rate, blood pressure, and respiration are associated with increases in stress, but they are also associated with physical movement, which may be caused by a non-stress event (such as, for example, exercise). Physical exertion changes heart rate, blood pressure, heart rate variability, respiratory rate, oxygen saturation, sweat and galvanic skin response, as well as blood glucose level. All of these can be used as crucial markers for accurately estimating stress. For example, when using heart-rate variability to measure stress, the results may be confounded if physical movement and exertion is not taken into account during the stress measurement. Furthermore, many sensors provide erroneous data when accelerated, for example, because the physical connection between the sensor and the subject moves, causing the sensor to generate an inaccurate or false reading. By using an accelerometer (or another suitable movement sensor, such as, for example, a kinesthetic sensor), analysis system 180 may monitor the physical movement and exertion of a person. By contextualizing physiological sensor data with accelerometer data, analysis system 180 may be able to eliminate changes in physiological data or erroneous sensor measurements caused by physical movement and thereby more accurately measure and monitor stress in a person.

In particular embodiments, analysis system 180 may measure and monitor stress by analyzing one or more data streams from one or more physical motion sensors, such as, for example, an accelerometer, a kinesthetic sensor, an actigraph, a motion sensor, or another suitable physical motion sensor. A physical motion sensor may measure a person's speed, acceleration, exertion, movement, or exertion. After measuring the person's physical motion, the physical motion sensor may then transmit one or more data streams comprising the user's physical motion data to analysis system 180. Analysis system 180 may then analyze this physical motion by inputting it into a stress model that correlates physical motion with stress to calculate the person's stress index. Analysis system 180 may continuously monitor a data stream containing physical motion data of a person, thereby allowing it to accurately measure and monitor the person's stress and stress-related health states. Although this disclosure describes measuring and monitoring stress using particular types of physical motion sensors, this disclosure contemplates measuring and monitoring stress using any suitable physical motion sensors.

In particular embodiments, analysis system 180 may access one or more data streams from an accelerometer and one or more of other sensors 112 to measure and monitor stress in a person. The data streams may comprise psychological data of the person, behavioral data of the person, or physiological data of the person. In particular embodiments, analysis system 180 may access data streams from an accelerometer and one or more of a heart-rate monitor, a blood-pressure monitor, a pulse oximeter, or a mood sensor. Although this disclosure describes accessing particular sensors 112 and particular data streams to measure and monitor stress in a person, this disclosure contemplates accessing any suitable sensors 112 and any suitable data streams to measure and monitor stress in a person.

In particular embodiments, analysis system 180 may access a plurality of data sets from the data streams to measure and monitor stress in a person. A typical diagnostic test involves generating at least two data sets, wherein the data sets are collect from the person when he is engaged in different levels of physical activity. The data sets may include one or more data sets from one or more sensors 112 in sensor array 110. As an example and not by way of limitation, a first data set may be collected from the person when the person is engaged in a first activity (e.g., walking), and a second data set may be collected from the person when the person is engaged in a second activity (e.g., running) As another example and not by way of limitation, a first data set may be collected from the person when the person is substantially resting, and a second data set may be collected from the person when the person is engage in more than minimal activity. Analysis system 180 may then use the accelerometer data to deconfound the data from other sensors 112 to determine whether measured changes in the physiological state of a person are caused by stress or by the physical motion of the person. The accuracy of determining stress in a person may generally be increased as the number of data sets is increased. Therefore, multiple data sets may be generated and analyzed to determine stress in a person. Although this disclosure describes accessing particular data sets to measure and monitor stress in a person, this disclosure contemplates accessing any suitable data sets to measure and monitor stress in a person.

In particular embodiments, analysis system 180 may access a stress model of a person. As an example and not by way of limitation, a stress model may be an algorithm based on renal-Doppler data and accelerometer data and one or more of heart-rate data, blood-pressure data, pulse-oximetry data, or mood data. As an example and not by way of limitation, a stress model could be an algorithm based on sensor measurements made by one or more sensors 112 over some control period. The stress model may include a variety of variables, including data from one or more data streams and one or more fixed variables. The following is an example algorithm that analysis system 180 could access that models the stress of a person:

$$f_{sm} = f(D_{acc}^1, D_{HR}^2, D_{BP}^3, D_{SpO2}^4, D_{mood}^5, X^1, \ldots, X^M)$$

where:

$f_{sm}$ is the stress model, $(D_{acc}^1)$ is the physical activity (acceleration) of the person, $(D_{HR}^2)$ is the heart rate of the person, $(D_{BP}^3)$ is the blood pressure of the person, $(D_{SpO2}^4)$ is the blood-oxygen level of the person, $(D_{mood}^5)$ is the psychological state (mood) of the person, and $(X^1, \ldots, X^M)$ are fixed variables 1 through M.

Although this disclosure describes accessing particular stress models based on particular data or variables, this disclosure contemplates accessing any suitable stress models based on any suitable data or variables.

In particular embodiments, analysis system 180 may analyze data sets from the accelerometer data stream and one or more other data streams with respect to each other. Analysis system 180 may use any suitable process, calculation, or technique to analyze the data streams with respect to each other. As an example and not by way of limitation, analysis system 180 may compare the first data set and a second data to identify any changes in the acceleration of the person and to identify any corresponding changes in physiological state. As another example and not by way of limitation, analysis system 180 may analyze the data streams and identify data points or data ranges from the data streams that may be used as inputs into a stress model. In particular embodiments, analysis system 180 may contextualize the acceleration data with other data, such as, for example, by mapping the data with respect to each other. As an example and not by way of limitation, analysis system 180 may contextualize accelerometer data of the person with heart-rate data, blood-pressure data, pulse-oximetry data, and mood data of the person, allowing analysis system 180 to identify correlations between changes in the acceleration data and the other data. Although this disclosure describes particular components performing particular processes to analyze the data streams with respect to the each other, this disclosure contemplates any suitable components performing any suitable processes to analyze the data streams with respect to the each other.

In particular embodiments, analysis system 180 may determine the current stress index of a person based on the analysis of a plurality of data sets from the accelerometer data stream and one or more other data streams with respect to each other. The stress index may be determined both from the acceleration of the person and the physiological state of the person. As discussed previously, various physiological states may correlate with stress, such as, for example, increased heart rate, increased blood pressure, or decreased blood oxygen. However, these same physiological states may also correlate with increased physical motion (e.g., acceleration). As an example and not by way of limitation, analysis system 180 may examine the data streams and identify physiological states that correlate with stress or a lack of stress and identify whether the measured physiological states correlate with acceleration of the person. Analysis system 180 may analyze one data set to determine the baseline stress of the person and then analyze another data set to determine the change in the person's physiological states to determine a current stress index of the person. Analysis system 180 may determine the current stress index of the person by determining the magnitude that each of the physiological states correlates with stress or lack of stress. As an example and not by way of limitation, a low heart rate and low acceleration may correlate with a low stress index while a high heart rate and low acceleration may correlate with a high stress index. Although this disclosure describes particular components performing particular processes to determine the current stress index of a person, this disclosure contemplates any suitable components performing any suitable processes to determine the current stress index of a person. Moreover, although this disclosure describes analyzing particular data streams for particular correlations to determine the current stress index of a person, this disclosure contemplates analyzing any suitable data streams for any suitable correlations to determine the current stress index of a person.

In particular embodiments, analysis system 180 may use a stress model of a person to determine the current stress index of the person based on the analysis of data sets from the accelerometer data stream and one or more other data streams with respect to each other. As an example and not by way of limitation, the stress model may directly calculate the stress index of the person, such that $f_{sm}$=SI, where SI is the stress index of the person. As another example and not by way of limitation, the stress index of the person may be based on the stress model, such that $f(f_{sm})$=SI. Analysis system 180 may calculate the stress index of the person based on the data from the accelerometer data stream and the other data streams. As an example and not by way of limitation, analysis system 180 may input data points or data ranges from the accelerometer data stream and the other data streams into the stress model as independent variables. Analysis system 180 may then calculate the stress index of the person by solving the stress model. Although this disclosure describes particular components performing particular processes to determine the current stress index of a person, this disclosure contemplates any suitable components performing any suitable processes to determine the current stress index of a person. Moreover, although this disclosure describes particular relationships between the stress model of a person and the stress index of the person, this disclosure contemplates any suitable relationship between the stress model of a person and the stress index of the person.

In particular embodiments, analysis system 180 may access one or more data streams from one or more additional sensors 112 to measure and monitor stress in a person. As described previously, analysis system 180 may access, for example, a behavioral sensor, an electrocardiograph, a glucocorticoid meter, an electromyograph, a respiration sensor, a galvanic-skin-response sensor, or another suitable sensor 112. Analysis system 180 may then analyze these additional data streams, allowing it to more accurately measure and monitor the stress of the person, such as, for example, by deconfounding physiological data caused by non-stress related events.

FIG. 12 illustrates an example method 1200 for monitoring stress using accelerometer data. The method begins at step 1210, where analysis system 180 accesses one or more data streams from a plurality of sensors 112. The sensors 112 may comprise an accelerometer and one or more of a heart-rate monitor, a blood-pressure monitor, a pulse oximeter, or a mood sensor. The data streams may comprise accelerometer data of a person from the accelerometer and one or more of heart-rate data of the person from the heart rate monitor, blood-pressure data of the person from the blood-pressure monitor, pulse-oximetry data of the person from the pulse oximeter, and mood data of the person from the mood sensor. A first data set from the data streams may be collected from the person at a first time and the person may be engaged in a first activity at the first time. A second data set from the data streams may be collected from the person at a second time and the person may be engaged in a second activity at the second time. At step 1220, analysis system 180 may analyze the first data set and the second data set with respect to each other. At step 1230, analysis system 180 may determine a current stress index of the person based on the analysis of the first data set and the second data set with respect to each other. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates particular components carrying out particular steps of the method of FIG. 12, this disclosure contemplates any suitable combination of any suitable components carrying out any suitable steps of the method of FIG. 12.

Continuous Monitoring of Stress Using Environmental Data

Another problem in measuring and monitoring stress accurately is determining whether any changes in measured parameters are caused by environmental (i.e., exogenous) factors. Various physiological sensors may be used in an attempt to measure stress, such as, for example, heart-rate monitors, blood-pressure monitors, pulse oximeters, or respiration sensors. However, because stress is often caused by environmental factors, determining the causes of stress may be impossible by monitoring physiological sensors alone. Various environmental sensors may be used in an attempt to monitor stress, such as, for example, barometers, location sensors, traffic sensors, or data feeds. For example, increases in heart rate, blood pressure, and respiration in a person are associated with increases in stress in the person. But measuring merely these physiological may tell nothing about the cause of stress in the person. These physiological responses may be caused by environmental stressors, such as, for example, changing weather, changing the person's location, encountering traffic, or receiving news from a data feed. Most current methods for measuring stress only consider physiological data associated with the subject, thus removing the analysis from its context. Consequently, it may be difficult to establish the causes of stress without an understanding of environmental factors that may act as stressors. By contextualizing physiological sensor data with this environmental data, analysis system 180 may be able to identify changes in physiological data caused by exogenous events and thereby more accurately measure and monitor stress in a person, and more accurately identify the environmental causes of stress (i.e., stressors) for the person.

In particular embodiments, analysis system 180 may measure and monitor stress by analyzing one or more data streams from one or more environmental sensors. The environmental sensors may include, for example, a barometer, a weather sensor, a pollen counter, a location sensor, a seismometer, an altimeter, a hydrometer, a decibel meter, a light meter, a thermometer, a wind sensor, a traffic sensor, another suitable environmental sensor, or two or more such sensors. As used herein, the term "environmental sensor" is used broadly. For example, a canary in a cage, as used by miners to warn of gas, could be considered an environmental sensor. One or more of the environmental sensors may be a data feed. The data feeds may include, for example, a stock-market ticker, a weather report, a news feed, a traffic-condition update, a public-health notice, an electronic calendar, a social network news feed, another suitable data feed, or two or more such data feeds. The environmental sensors may then transmit one or more data streams comprising the environmental data to analysis system 180. Analysis system 180 may then analyze this environmental data by inputting it into a stress model that correlates environmental states with stress to calculate the person's stress index. Analysis system 180 may also analyze this environmental data to identify events that may act as stressors on a person. Analysis system 180 may continuously monitor a data stream containing environmental data, thereby allowing it to accurately measure and monitor exogenous events that may cause stress in a person. Although this disclosure describes measuring and monitoring stress using particular types of environmental sensors, this disclosure contemplates measuring and monitoring stress using any suitable environmental sensors.

In particular embodiments, analysis system 180 may access one or more data streams from an environmental sensor and one or more of other sensors 112 to measure and monitor stress in a person. The data streams may comprise environmental data and one or more of psychological data of the person, behavioral data of the person, or physiological data of the person. In particular embodiments, analysis system 180 may access data streams from an environmental sensor and one or more of a mood sensor, a heart-rate monitor, a blood-pressure monitor, a pulse oximeter, or an accelerometer. Although this disclosure describes accessing particular sensors 112 and particular data streams to measure and monitor stress in a person, this disclosure contemplates accessing any suitable sensors 112 and any suitable data streams to measure and monitor stress in a person.

In particular embodiments, analysis system 180 may access a plurality of data sets from the data streams to measure and monitor stress in a person. A typical diagnostic test involves generating at least two data sets, wherein the data sets are collected when the environmental states are different between at least two of the data sets. The data sets may include one or more data sets from one or more sensors 112 in sensor array 110. As an example and not by way of limitation, a first data set may be collected when the environmental data indicates a first state, and a second data set may be collected when the environmental data indicates a second state. As another example and not by way of limitation, a first data set may be collected when the person is exposed to a particular stressor, and a second data set may be collected when the person is not exposed to the particular stressor. As yet another example and not by way of limitation, a first data set may be collected when the person is substantially stressed, and a second data set may be collected when the person is substantially unstressed. As yet another example and not by way of limitation, a first data set may be collected when the person is engaged in a first activity, and a second data set may be collected when the person is engaged in a second activity. Analysis system 180 may then use the environmental data to deconfound the data from other sensors 112 to determine whether measured changes in the physiological state of a person are caused by stress or non-stress related events. The accuracy of determining stress in a person may generally be increased as the number of data sets is increased. Therefore, multiple data sets may be generated and analyzed to determine stress in a person. Although this disclosure describes accessing particular data sets to measure and monitor stress in a person, this disclosure contemplates accessing any suitable data sets to measure and monitor stress in a person.

In particular embodiments, analysis system 180 may access a stress model of a person. As an example and not by way of limitation, a stress model may be an algorithm based on renal-Doppler data and environmental data and one or more of mood data, heart-rate data, blood-pressure data, pulse-oximetry data, or accelerometer data. As an example and not by way of limitation, a stress model could be an algorithm based on sensor measurements made by one or more sensors 112 over some control period. The stress model may include a variety of variables, including data from one or more data streams and one or more fixed variables. The following is an example algorithm that analysis system 180 could access that models the stress of a person:

$$f_{sm} = f(D_{env}^1, D_{mood}^2, D_{HR}^3, D_{BP}^4, D_{SpO2}^5, D_{acc}^6, X^1, \ldots, X^M)$$

where:
$f_{sm}$ is the stress model,
$(D_{env}^1)$ is the environmental state,
$(D_{mood}^2)$ is the psychological state (mood) of the person,
$(D_{HR}^3)$ is the heart rate of the person,
$(D_{BP}^4)$ is the blood pressure of the person,
$(D_{SpO2}^5)$ is the blood-oxygen level of the person,
$(D_{acc}^6)$ is the physical activity (acceleration) of the person, and
$(X^1, \ldots, X^M)$ are fixed variables 1 through M.

Although this disclosure describes accessing particular stress models based on particular data or variables, this disclosure contemplates accessing any suitable stress models based on any suitable data or variables.

In particular embodiments, analysis system 180 may analyze data sets from the environmental data stream and one or more other data streams with respect to each other. Analysis system 180 may use any suitable process, calculation, or technique to analyze the data streams with respect to each other. As an example and not by way of limitation, analysis system 180 may compare the first data set and a second data to identify any changes in the environmental state and to identify any corresponding changes in physiological state of the person. As another example and not by way of limitation, analysis system 180 may analyze the data streams and identify data points or data ranges from the data streams that may be used as inputs into a stress model. In particular embodiments, analysis system 180 may contextualize the environmental data with other data, such as, for example, by mapping the data with respect to each other. As an example and not by way of limitation, analysis system 180 may contextualize environmental data with mood data, heart-rate data, blood-pressure data, pulse-oximetry data, and acceleration data of the person, allowing analysis system 180 to identify correlations between changes in the environmental data and the other data. Although this disclosure describes particular components performing particular processes to analyze the data streams with respect to the each other, this disclosure contemplates any suitable components performing any suitable processes to analyze the data streams with respect to the each other.

In particular embodiments, analysis system 180 may determine the current stress index of a person based on the analysis of a plurality of data sets from the environmental data stream and one or more other data streams with respect to each other. The stress index may be determined both from the environmental state and the physiological or psychological state of the person. As discussed previously, various physiological states may correlate with stress, such as, for example, increased heart rate, increased blood pressure, or decreased blood oxygen. Similarly, various environmental states may correlate with stress, such as, for example, changes in weather, increased pollen counts, changes in location, earthquakes and other natural disasters, changes in elevation, increased noise levels, changes in lighting, increased traffic, declines in the stock-market, disease outbreaks, or changes in social network status (e.g., de-friending, changing relationship status). Physiological responses that correlate with stress may be caused by particular environmental stressors, which may be identified in the environmental data. As an example and not by way of limitation, analysis system 180 may examine the data streams and identify physiological states that correlate with stress or a lack of stress and identify whether the measured physiological states correlate with an environmental state. Analysis system 180 may analyze one data set to determine the baseline stress of the person and then analyze another data set to determine the change in the person's physiological states to determine a current stress index of the person. Analysis system 180 may determine the current stress index of the person by determining the magnitude that each of the physiological states correlates with stress or lack of stress. As an example and not by way of limitation, a low respiration rate may correlate with a low stress index while a high respiration rate may correlate with a high stress index. As another example and not by way of limitation, a small drop in the stock market may correlate with a low stress index while a large drop in the stock market may correlate with a high stress index. Although this disclosure describes particular components performing particular processes to determine the current stress index of a person, this disclosure contemplates any suitable components performing any suitable processes to determine the current stress index of a person. Moreover, although this disclosure describes analyzing particular data streams for particular correlations to determine the current stress index of a person, this disclosure contemplates analyzing any suitable data streams for any suitable correlations to determine the current stress index of a person.

In particular embodiments, analysis system 180 may use a stress model of a person to determine the current stress index of the person based on the analysis of data sets from the environmental data stream and one or more other data streams with respect to each other. As an example and not by way of limitation, the stress model may directly calculate the stress index of the person, such that $f_{sm}=SI$, where SI is the stress index of the person. As another example and not by way of limitation, the stress index of the person may be based on the stress model, such that $f(f_{sm})=SI$. Analysis system 180 may calculate the stress index of the person based on the data from the environmental data stream and the other data streams. As an example and not by way of limitation, analysis system 180 may input data points or data ranges from the environmental data stream and the other data streams into the stress model as independent variables. Analysis system 180 may then calculate the stress index of the person by solving the stress model. Although this disclosure describes particular components performing particular processes to determine the current stress index of a person, this disclosure contemplates any suitable components performing any suitable processes to determine the current stress index of a person. Moreover, although this disclosure describes particular relationships between the stress model of a person and the stress index of the person, this disclosure contemplates any suitable relationship between the stress model of a person and the stress index of the person.

In particular embodiments, analysis system 180 may access one or more data streams from one or more additional sensors 112 to measure and monitor stress in a person. As described previously, analysis system 180 may access, for example, a behavioral sensor, an electrocardiograph, a glucocorticoid meter, an electromyograph, a respiration sensor, a galvanic-skin-response sensor, or another suitable sensor 112. Analysis system 180 may then analyze these additional data streams, allowing it to more accurately measure and monitor the stress of the person, such as, for example, by deconfounding physiological data caused by non-stress related events.

FIG. 13 illustrates an example method 1300 for monitoring stress using environmental data. The method begins at step 1310, where analysis system 180 accesses one or more data streams from a plurality of sensors 112. The sensors 112 may comprise an environmental sensor and one or more of a mood sensor, a heart-rate monitor, a blood-pressure monitor, a pulse oximeter, or an accelerometer. The data streams may comprise environmental data from the environmental sensor and one or more of mood data of a person from the mood sensor, heart-rate data of the person from the heart-rate monitor, blood-pressure data of the person from the blood-pressure monitor, pulse oximetry data of the person from the pulse oximeter, and accelerometer data of the person from the accelerometer. A first data set from the data streams may be collected at a first time and the environmental data in the first data set may indicate a first state at the first time. A second data set from the data streams may be collected at a second time and the environmental data in the second data set may indicate a second state at the second time. At step 1320, analysis system 180 may analyze the first data set and the second data set with respect to each other. At step 1330, analysis system 180 may determine a current stress index of the person based on the analysis of the first data set and the second data set with respect to each other. Although this disclosure describes and illustrates particular steps of the method of FIG. 13 as occurring in a particular order, this disclosure contemplates any suitable steps of the method of FIG. 13 occurring in any suitable order. Moreover, although this disclosure describes and illustrates particular components carrying out particular steps of the method of FIG. 13, this disclosure contemplates any suitable combination of any suitable components carrying out any suitable steps of the method of FIG. 13.

Calculating and Monitoring a Composite Stress Index

Measuring and quantifying stress levels is difficult because there are a variety of physiological, psychological, behavioral, and environmental factors that may contribute to a person's stress response. For example, physiological stress represents a wide range of physical responses that occur as a direct result of a stressor causing an upset in the homeostasis of the body. Upon immediate disruption of either psychological or physiological equilibrium, the body responds by stimulating the nervous, endocrine, and immune systems. The reaction of these systems causes a number of physiological changes that have both short-term and long-term effects on the body. However, physiological stress may be caused internally or by psychological, behavioral, or environmental factors. Therefore, a composite stress index capable of quantifying stress caused by a variety of sources is needed.

Particular stressors may be associated with particular changes in the stress index of a person (i.e., stress factors). For example, one could have a "meeting stress factor," a "traffic stress factor," a "social-engagement stress factor," an "economic-change stress factor," and so on. Therefore, the stress index may be calibrated with respect to specific stressors. Each person may have personalized responses and recovery patterns for each type of stressor, indicating a variety of stress factors and stress resilience coefficients. Analysis system 180 may be used to measure and monitor stress factors and stress resilience. This may allow a user to determine the types of stressors that lead to different resilience patterns in a given individual or population, which may be useful for helping with stress management.

In particular embodiments, a stress factor may be assigned to a particular stressor. A stress factor is the change in a person's stress index associated with a particular stressor or therapy. Thus, a person's stress after being exposed to a particular stressor is based on the person's stress before being exposed to the particular stressor and the stress factor associated with the stressor. As an example and not by way of limitation, a person's current stress index may be $SI=f(SI_0, SF_i)$, where SI is the current stress index of the person, $SI_0$ is the stress index of the person before being exposed to stressor i, and $SF_i$ is the stress factor associated with stressor i. In particular embodiments, the stress factor may be added to the prior stress index of a person to calculate a current stress index. As an example and not by way of limitation, a minor stressor, such a attempting to solve relatively simple mathematical questions, may increase a person's stress index by 5 points on a 0-to-100 stress scale, while a major stressor, such as have an argument with one's spouse, may increase a person's stress index by 20 points on the same stress scale. Thus, the minor stress would be assigned a stress factor of (+5)/100 and the major stressor would be assigned a stress factor of (+20)/100. In particular embodiments, the stress factor may be used to perform a mathematical operation other than simple linear addition (such as, for example, multiplication, division, exponentiation, negation, trigonometric function, or other suitable mathematical operations) or be used as part of a mathematical function to calculate the current stress index of a person. Although this disclosure describes assigning particular stress factors with particular stressors, this disclosure contemplates assigning any suitable stress factors with any suitable stressors.

In particular embodiments, analysis system 180 may measure and monitor stressors by analyzing data streams from the following three groups of sensors 112: (1) one or more physiological sensors; (2) one or more deconfounding sensors; and (3) one or more stressor sensors. Analysis system 180 may measure one or more physiological parameters from the sensors 112 in the first group. Then data from the sensors 112 in the second group may be used to deconfound the physiological data from the first group to determine whether physiological changes are actually caused by stress and not a non-stress related event. Finally, the data from the sensors 112 in the third group may measure changes in psychological, behavioral, or environmental states that may act as stressors. After the sensors 112 in the three groups take appropriate measurements, the sensors 112 may then transmit one or more data streams comprising the user's physiological data and other data to analysis system 180. Analysis system 180 may then analyze the data from the first and second groups of sensors 112 by inputting it into a stress model that correlates physiological data and other data with stress to calculate the person's stress index and the change in stress index caused by a stressor. By isolating the stress index measurement to the first and second groups of sensors 112, the change in stress index caused by a particular stressor (as measured by the sensors 112 from the third group) can be accurately determined. Analysis system 180 may continuously monitor data streams from the three groups of sensors 112, thereby allowing it to accurately measure and monitor the person's stress and stress-related health states. Although this disclosure describes measuring and monitoring stressors using particular types and groups of sensors 112, this disclosure contemplates measuring and monitoring stressors using any suitable types or groups of sensors 112.

In particular embodiments, analysis system 180 may access one or more data streams from a first, second, and third group of sensors 112 to measure and monitor stressors. The data streams may comprise physiological data of the person, psychological data of the person, behavioral data of the person, or environmental data. In particular embodiments, analysis system 180 may access data streams from one or more first sensors selected from a first group of sensor types consisting of a heart-rate monitor, a blood-pressure monitor, a pulse oximeter, and an accelerometer. These first sensors may transmit data streams comprising heart-rate data of the person, blood-pressure data of the person, pulse-oximeter data of the person, and accelerometer data of the person, respectively. In particular embodiments, analysis system 180 may access data streams from one or two second sensors selected from a second group of sensor types consisting of a mood sensor, a behavioral sensor, and an environmental sensor. These second sensors may transmit mood data of the person, behavioral data of the person, and environmental data, respectively. In particular embodiments, analysis system 180 may access data streams from one third sensor selected from the second group of sensor types, where the third sensor is of a different sensor type than any of the second sensors. As an example and not by way of limitation, if the second sensors are a mood sensor and a behavioral sensor, then the third sensor may only be an environmental sensor. As another example and not by way of limitation, if the second sensor is a mood sensor, then the third sensor may be either a behavioral sensor or an environmental sensor. Although this disclosure describes accessing particular sensors 112 and particular data streams to measure and monitor stressors, this disclosure contemplates accessing any suitable sensors 112 and any suitable data streams to measure and monitor stressors.

In particular embodiments, analysis system 180 may access a plurality of data sets from the data streams to measure and monitor stressors. A typical diagnostic test involves generating at least two data sets, wherein the data sets are collect from the person when he is exposed to a particular stressor and then not exposed to a particular stressor. The data sets may include one or more data sets from one or more sensors 112 in sensor array 110. As an example and not by way of limitation, a first data set may be collected from the person when the person is exposed to a particular stressor (e.g., arguing), and a second data set may be collected from the person when the person is not exposed to the particular stressor. As another example and not by way of limitation, a first data set may be collected from the person when the person is substantially stressed, and a second data set may be collected from the person when the person substantially unstressed. As yet another example and not by way of limitation, a first data set my be collected from the person when the person is engaged in a first activity that may be stressful, and a second data set may be collected from the person when the person is engaged in a second activity that may not be stressful. Analysis system 180 may then use the data from the second group of sensors 112 to deconfound the data from the first group of sensors 112 to determine whether measured changes in the physiological state of a person are caused by a stressor (as measured by data from the third group of sensors 112) or a non-stress related event (e.g., physical motion of the person). The accuracy of determining a stress factor for a particular stressor may generally be increased as the number of data sets is increased. Therefore, multiple data sets may be generated and analyzed to determine a stress factor for a stressor. Although this disclosure describes accessing particular data sets to measure and monitor stressors, this disclosure contemplates accessing any suitable data sets to measure and monitor stressors.

In particular embodiments, analysis system 180 may access a stress model of a person. As an example and not by way of limitation, a stress model may be an algorithm based on renal-Doppler data and two or more of heart-rate data, blood-pressure data, pulse-oximetry data, or mood data. As an example and not by way of limitation, a stress model could be an algorithm based on sensor measurements made by one or more sensors 112 over some control period. The stress model may include a variety of variables, including data from one or more data streams and one or more fixed variables. The following is an example algorithm that analysis system 180 could access that models the stress of a person:

$$f_{sm} = f(D_{HR}^1, D_{BP}^2, D_{SpO2}^3, D_{acc}^4, D_{mood}^5, D_{beh}^6, D_{env}^7, X^1, \ldots, X^M)$$

where:
$f_{sm}$ is the stress model,
$(D_{HR}^1)$ is the heart rate of the person,
$(D_{BP}^2)$ is the blood pressure of the person,
$(D_{SpO2}^3)$ is the blood-oxygen level of the person,
$(D_{acc}^4)$ is the physical activity (acceleration) of the person,
$(D_{mood}^5)$ is the psychological state (mood) of the person,
$(D_{beh}^6)$ is the behavioral state (activity) of the person,
$(D_{env}^7)$ is the environmental state and
$(X^1, \ldots, X^M)$ are fixed variables 1 through M.

Although this disclosure describes accessing particular stress models based on particular data or variables, this disclosure contemplates accessing any suitable stress models based on any suitable data or variables.

In particular embodiments, analysis system 180 may analyze data sets from the data streams from the first, second, and third groups of sensors 112 with respect to each other. Analysis system 180 may use any suitable process, calculation, or technique to analyze the data streams with respect to each other. As an example and not by way of limitation, analysis system 180 may compare the first data set and a second data to identify any changes in the physiological state the person and to identify any corresponding changes in psychological, behavioral, or environmental state. As another example and not by way of limitation, analysis system 180 may analyze the data streams and identify data points or data ranges from the data streams that may be used as inputs into a stress model. In particular embodiments, analysis system 180 may contextualize the physiological data with other data, such as, for example, by mapping the data with respect to each other. As an example and not by way of limitation, analysis system 180 may contextualize physiological data of the person with psychological, behavioral, or environmental data, allowing analysis system 180 to identify correlations between changes in the physiological data and the other data. Although this disclosure describes particular components performing particular processes to analyze the data streams with respect to the each other, this disclosure contemplates any suitable components performing any suitable processes to analyze the data streams with respect to the each other.

In particular embodiments, analysis system 180 may determine the current stress factor for a stressor based on the analysis of a plurality of data sets from the data streams from the first, second, and third groups of sensors 112 with respect to each other. The stress factor may be determined both from the physiological data of the person and the psychological, behavioral, and environmental data. As discussed previously, various physiological states may correlate with stress, such as, for example, increased heart rate, increased blood pressure, or decreased blood oxygen. However, these same physiological states may also be caused by non-stress related events. As an example and not by way of limitation, analysis system 180 may examine the data streams from the first group of sensors 112 and identify physiological states that correlate with stress or a lack of stress, identify whether the measured physiological states were caused by a non-stress related event as measured by the second group of sensors 112, and identify whether the measured physiological states correlate with a stress event as measure by the third group of sensors 112. Analysis system 180 may analyze one data set to determine the baseline stress of the person and then analyze another data set to determine the change in the person's physiological states to determine the change in the stress index of the person and thereby the stress factor for the stressor measured by the third group of sensors 112. Although this disclosure describes particular components performing particular processes to determine the current stress factor for a stressor, this disclosure contemplates any suitable components performing any suitable processes to determine the current stress factor for a stressor. Moreover, although this disclosure describes analyzing particular data streams for particular correlations to determine the current stress factor for a stressor, this disclosure contemplates analyzing any suitable data streams for any suitable correlations to determine the current stress factor for a stressor.

In particular embodiments, analysis system 180 may use a stress model of a person to determine the current stress factor for a stressor based on the analysis of data sets from the data streams from the first, second, and third groups of sensors 112 with respect to each other. As an example and not by way of limitation, the stress model may directly calculate the stress index of the person, such that $f_{sm}=SI$, where SI is the stress index of the person. As another example and not by way of limitation, the stress index of the person may be based on the stress model, such that $f(f_{sm})=SI$. Analysis system 180 may calculate the stress index of the person based on the data from the physiological data streams and the other data streams. As an example and not by way of limitation, analysis system 180 may input data points or data ranges from the data streams from the first and second group of sensors 112 into the stress model as independent variables. Analysis system 180 may calculate the stress index of the person at the first time and the second time by solving the stress model. Analysis system 180 may then calculate the stress factor of the stressor measured by the third sensor by calculating the change in the stress index of the person from the first time to the second time.

Although this disclosure describes particular components performing particular processes to determine the current stress factor for a stressor, this disclosure contemplates any suitable components performing any suitable processes to determine the current stress factor for a stressor.

In particular embodiments, analysis system 180 may access one or more data streams from one or more additional sensors 112 to measure and monitor stressors. As described previously, analysis system 180 may access, for example, an electrocardiograph, a glucocorticoid meter, an electromyograph, a respiration sensor, a galvanic-skin-response sensor, or another suitable sensor 112. Analysis system 180 may then analyze these additional data streams, allowing it to more accurately measure and monitor the stressors, such as, for example, by deconfounding physiological data caused by non-stress related events.

FIG. 14 illustrates an example method 1400 for calculating a stress factor for a stressor. The method begins at step 1410, where analysis system 180 accesses one or more data streams from a plurality of sensors 112. The sensors 112 may comprise one or more first sensors selected from a first group of sensor types consisting of a heart-rate monitor, a blood-pressure monitor, a pulse oximeter, and an accelerometer. The sensors 112 may further comprise one or two second sensors selected from a second group of sensor types consisting of a mood sensor, a behavioral sensor and an environmental sensor. The sensors 112 may further comprise a third sensor also selected from the second group of sensor types. The third sensor is different in sensor type from each of the two second sensors. The data streams comprise one or more of heart-rate data of a person from the heart-rate monitor, blood-pressure data of the person from the blood-pressure monitor, pulse-oximetry data of the person from the pulse oximeter, accelerometer data of the person from the accelerometer, mood data of the person from the mood sensor, behavioral data of the person from the behavioral sensor, or environmental data from the environmental sensor. A first data set from the data streams may be collected from the person at a first time and the person may be exposed to a stressor at the first time, as indicated by data in the first data set from the third sensor. A second data set from the data streams may be collected from the person at a second time and the person may not have been exposed to the stressor at the second time, as indicated by data in the second data set from the third sensor. At step 1420, analysis system 180 may analyze the first data set and the second data set with respect to each other. At step 1430, analysis system 180 may determine a current stress factor for the stressor with respect to the person based on the analysis of the first data set and the second data set with respect to each other. Although this disclosure describes and illustrates particular steps of the method of FIG. 14 as occurring in a particular order, this disclosure contemplates any suitable steps of the method of FIG. 14 occurring in any suitable order. Moreover, although this disclosure describes and illustrates particular components carrying out particular steps of the method of FIG. 14, this disclosure contemplates any suitable combination of any suitable components carrying out any suitable steps of the method of FIG. 14.

Calculating and Monitoring the Efficacy of Stress-Related Therapies

Another problem with measuring and monitoring stress accurately is determining whether particular stress-reduction therapies are effective. Many different techniques for stress reduction exist. Quantifying the effectiveness of stress reduction may be done by contextualizing the therapy with a variety of data, such as, for example, physiological, psychological, behavioral, or environmental data. An appropriate stress management approach may differ based upon the nature of the stressor or the person. For example, for a particular person, breathing exercises may be more effective than cognitive reframing when the stress is caused by a domestic argument, while the reverse may be true when the stress is cause by work-related stress. Consequently, a system capable of quantifying the effectiveness of stress reduction techniques for a particular person is needed.

Particular therapies may be associated with particular changes in the stress index of a person (i.e., stress factors). For example, one could have a "meditation stress factor," a "biofeedback stress factor," a "cognitive reframing stress factor," an "intervention stress factor," and so on. Therefore, the stress index may be calibrated with respect to specific therapies. Each person may have personalized responses and recovery patterns for each type of therapy, indicating a variety of stress factors and stress resilience coefficients. Analysis system 180 may be used to measure and monitor stress factors and stress resilience. This may allow a user to determine the types of therapies that are most effective in a given individual or population, which may be useful for helping with stress management.

In particular embodiments, a stress factor may be assigned to particular therapy. A stress factor is the change in a person's stress index associated with a particular stressor or therapy. As an example and not by way of limitation, a minor therapy, such a short breathing exercise, may decrease a person's stress index by 8 points on a 0-to-100 stress scale, while a therapy stressor, such as an hour of meditation, may decrease a person's stress index by 30 points on the same stress scale. Thus, the minor therapy would be assigned a stress factor of $(-8)/100$ and the major stressor would be assigned a stress factor of $(-30)/100$. Although this disclosure describes assigning particular stress factors with particular stressors, this disclosure contemplates assigning any suitable stress factors with any suitable stressors.

In particular embodiments, a person may engage in a variety of stress-related therapies. Stress-related therapies may include, for example, interventions, biofeedback, breathing exercises, progressive muscle relaxation exercises, presentation of personal media (e.g., music, personal pictures, etc.), offering an exit strategy (e.g., calling the user so he has an excuse to leave a stressful situation), references to a range of psychotherapeutic techniques, and graphical representations of trends (e.g., illustrations of health metrics over time), cognitive reframing therapy, other suitable stress-related therapies, or two or more such therapies. A person may receive a stress-related therapy in a variety of ways, such as, for example, from a third-person (e.g., a physician or therapist), from himself (e.g., self-relaxation techniques), from display system 190 (e.g., displaying a stress-related therapy), or from another suitable source. Analysis system 180 may receive input describing the therapies, such as the type, duration, and source of the therapy. Analysis system 180 may then contextualize stress index data with the therapy data to calculate the stress factor for the therapy. Although this disclosure describes particular therapies, this disclosure contemplates any suitable therapies.

In particular embodiments, analysis system 180 may measure and monitor stress-related therapies by analyzing one or more data streams from one or more sensors 112, such as, for example, an accelerometer, a heart-rate monitor, a blood-pressure monitor, a pulse oximeter, a mood sensor, a behavioral sensors, an environmental sensor, or another suitable sensor 112. These sensors 112 may be used to measure the stress index of a person, as described previously. After the sensors 112 take appropriate measurements, the sensors 112 may then transmit one or more data streams comprising the user's physiological, psychological, behavioral, or environmental data to analysis system 180. Analysis system 180 may then analyze this data by inputting it into a stress model that correlates physiological, psychological, behavioral, or environmental data with stress to calculate the person's stress index. Analysis system 180 may continuously monitor data streams from the sensors 112, thereby allowing it to accurately measure and monitor the person's stress, stress-related health states, and stress index. Although this disclosure describes measuring and monitoring stress-related therapies using particular types of sensors 112, this disclosure contemplates measuring and monitoring stress-related therapies using any suitable types of sensors 112.

In particular embodiments, analysis system 180 may access two or more data streams two or more sensors 112 to measure and monitor stress-related therapies. The data streams may comprise physiological data of the person, psychological data of the person, behavioral data of the person, or environmental data. In particular embodiments, analysis system 180 may access data streams from two or more of an accelerometer, a heart-rate monitor, a blood-pressure monitor, a pulse oximeter, or a mood sensor. Although this disclosure describes accessing particular sensors 112 and particular data streams to measure and monitor stress-related therapies, this disclosure contemplates accessing any suitable sensors 112 and any suitable data streams to measure and monitor stress-related therapies.

In particular embodiments, analysis system 180 may access a plurality of data sets from the data streams to measure and monitor stress-related therapies. A typical diagnostic test involves generating at least two data sets, wherein the data sets are collect from the person when he is engaged in a particular therapy and then not engaged in a particular therapy. The data sets may include one or more data sets from one or more sensors 112 in sensor array 110. As an example and not by way of limitation, a first data set may be collected from the person when the person is engaged in a particular therapy (e.g., meditation), and a second data set may be collected from the person when the person is not engaged in the particular therapy. As another example and not by way of limitation, a first data set may be collected from the person when the person is substantially stressed, and a second data set may be collected from the person when the person substantially unstressed. As yet another example and not by way of limitation, a first data set my be collected from the person when the person is engaged in a first activity that may be relaxing (i.e., a stress-related therapy), and a second data set may be collected from the person when the person is engaged in a second activity that may not be relaxing. Analysis system 180 may then determine whether measured changes in the physiological state of a person are caused by a stress-related therapy or a non-stress related event (e.g., ceasing physical activity). The accuracy of determining a stress factor for a particular stress-related therapy may generally be increased as the number of data sets is increased. Therefore, multiple data sets may be generated and analyzed to determine a stress factor for a stress-related therapy. Although this disclosure describes accessing particular data sets to measure and monitor stress-related therapies, this disclosure contemplates accessing any suitable data sets to measure and monitor stress-related therapies.

In particular embodiments, analysis system 180 may access a stress model of a person. As an example and not by way of limitation, a stress model may be an algorithm based on renal-Doppler data and two or more of accelerometer data, heart-rate data, blood-pressure data, pulse-oximetry data, or mood data. As an example and not by way of limitation, a stress model could be an algorithm based on sensor measurements made by one or more sensors 112 over some control period. The stress model may include a variety of variables, including data from one or more data streams and one or more fixed variables. The following is an example algorithm that analysis system 180 could access that models the stress of a person:

$$f_{sm} = f(D_{HR}^1, D_{HR}^2, D_{BP}^3, D_{SpO2}^4, D_{mood}^5, X^1, \ldots, X^M)$$

where:
$f_{sm}$ is the stress model,
$(D_{acc}^1)$ is the physical activity (acceleration) of the person,
$(D_{HR}^2)$ is the heart rate of the person,
$(DB_{BP}^3)$ is the blood pressure of the person,
$(D_{SpO2}^4)$ is the blood-oxygen level of the person,
$(D_{mood}^5)$ is the psychological state (mood) of the person, and
$(X^1, \ldots, X^M)$ are fixed variables 1 through M.

Although this disclosure describes accessing particular stress models based on particular data or variables, this disclosure contemplates accessing any suitable stress models based on any suitable data or variables.

In particular embodiments, analysis system 180 may analyze data sets from the data with respect to each other. Analysis system 180 may use any suitable process, calculation, or technique to analyze the data streams with respect to each other. As an example and not by way of limitation, analysis system 180 may compare the first data set and a second data to identify any changes in the physiological state the person and to identify any corresponding changes in psychological, behavioral, or environmental state. As another example and not by way of limitation, analysis system 180 may analyze the data streams and identify data points or data ranges from the data streams that may be used as inputs into a stress model. In particular embodiments, analysis system 180 may contextualize the physiological data with other data, such as, for example, by mapping the data with respect to each other. As an example and not by way of limitation, analysis system 180 may contextualize physiological data of the person with psychological, behavioral, or environmental data, allowing analysis system 180 to identify correlations between changes in the physiological data and the other data. Although this disclosure describes particular components performing particular processes to analyze the data streams with respect to the each other, this disclosure contemplates any suitable components performing any suitable processes to analyze the data streams with respect to the each other.

In particular embodiments, analysis system 180 may determine the current stress factor for a stress-related therapy based on the analysis of a plurality of data sets from the data streams with respect to each other. The stress factor may be determined both from the physiological, psychological, behavioral, and environmental data from the sensors 112 in sensor array 110. As discussed previously, various physiological states may correlate with stress, such as, for example, increased heart rate, increased blood pressure, or decreased blood oxygen. However, these same physiological states may also be caused by non-stress related events. As an example and not by way of limitation, analysis system 180 may examine the data streams and identify physiological states that correlate with stress or a lack of stress, identify whether the measured physiological states were caused by a non-stress related event as measured by the second group of sensors 112, and identify whether the measured physiological states correlate with a stress-related therapy. Analysis system 180 may analyze one data set to determine the baseline stress of the person and then analyze another data set to determine the change in the person's physiological states to determine the change in the stress index of the person and thereby the stress factor for the stress-related therapy. Although this disclosure describes particular components performing particular processes to determine the current stress factor for a stress-related therapy, this disclosure contemplates any suitable components performing any suitable processes to determine the current stress factor for a stress-related therapy. Moreover, although this disclosure describes analyzing particular data streams for particular correlations to determine the current stress factor for a stress-related therapy, this disclosure contemplates analyzing any suitable data streams for any suitable correlations to determine the current stress factor for a stress-related therapy.

In particular embodiments, analysis system 180 may use a stress model of a person to determine the current stress factor for a therapy based on the analysis of data sets from the data streams with respect to each other. As an example and not by way of limitation, the stress model may directly calculate the stress index of the person, such that $f_{sm}$=SI, where SI is the stress index of the person. As another example and not by way of limitation, the stress index of the person may be based on the stress model, such that $f(f_{sm})$=SI. Analysis system 180 may calculate the stress index of the person based on the data from the data streams. As an example and not by way of limitation, analysis system 180 may input data points or data ranges from the data streams into the stress model as independent variables. Analysis system 180 may calculate the stress index of the person at the first time and second time by solving the stress model. Analysis system 180 may then calculate the stress factor of the therapy by calculating the change in the stress index of the person from the first time to the second time. Although this disclosure describes particular components performing particular processes to determine the current stress index of a person, this disclosure contemplates any suitable components performing any suitable processes to determine the current stress index of a person.

In particular embodiments, analysis system 180 may access one or more data streams from one or more additional sensors 112 to measure and monitor stress-related therapies. As described previously, analysis system 180 may access, for example, a kinesthetic sensor, a behavioral sensor, an electrocardiograph, a glucocorticoid meter, an electromyograph, a respiration sensor, a galvanic-skin-response sensor, or another suitable sensor 112. Analysis system 180 may then analyze these additional data streams, allowing it to more accurately measure and monitor the stress-related therapies, such as, for example, by deconfounding physiological data caused by non-stress related events.

FIG. 15 illustrates an example method 1500 for calculating a stress factor for a therapy. The method begins at step 1510, where analysis system 180 accesses one or more data streams from a plurality of sensors 112. The sensors 112 may comprise two or more of an accelerometer, a heart-rate monitor, a blood-pressure monitor, a pulse oximeter, or a mood sensor. The data streams may comprise two or more of accelerometer data of a person from the accelerometer, heart-rate data of the person from the heart-rate monitor, blood-pressure data of the person from the blood-pressure monitor, pulse-oximetry data of the person from the pulse oximeter, or mood data of the person from the mood sensor. A first data set from the data streams may be collected from the person at a first time and the person may be engaged in a therapy at the first time. A second data set from the data streams may be collected from the person at a second time and the person may not have engaged in the therapy at the second time. At step 1520, analysis system 180 may analyze the first data set and the second data set with respect to each other. At step 1530, analysis system 180 may determine a current stress factor for the therapy on the person based on the analysis of the first data set and the second data set with respect to each other. Although this disclosure describes and illustrates particular steps of the method of FIG. 15 as occurring in a particular order, this disclosure contemplates any suitable steps of the method of FIG. 15 occurring in any suitable order. Moreover, although this disclosure describes and illustrates particular components carrying out particular steps of the method of FIG. 15, this disclosure contemplates any suitable combination of any suitable components carrying out any suitable steps of the method of FIG. 15.

Example 1

In this experiment, changes in either the renal blood flow in the main renal artery or in the intra-renal artery were measured in a patient in relaxed and stressed states. Renal blood flow was measured using a renal-pulse Doppler. Most readings were taken on the renal artery, as it is assumed that the best and most stable change in renal blood flow is reflected in the main artery near the kidney. The hypothesis for these experiments was that renal resistive index (renal RI) will increase with stress and decrease with relaxation.

Measurement Strategy: The first measurement is taken as soon as the experiment starts. This reading acts as a baseline renal blood flow. In this reading, the stress state is not known, and the patient may be in a stressed or relaxed state. After taking the initial reading, the patient is asked to relax (i.e., self-relaxation). In this method, the patient attempts to relax by himself with no external disturbance provided. The person is then asked to signal when he feels relaxed. After the person signals, another measurement is taken. After taking the measurements, the person is subjected to forced relaxation, which can include talking, telling jokes, etc. After the forced relaxation, another measurement is taken. Next, the person is then subjected to forced stress. The stress may be induced by asking the patient mathematical problems and asking him to orally solve the problems. After the forced stress, another measurement is taken. Next, the patient is again subjected to forced relaxation, and then a measurement is again taken. Finally, the patient is again subjected to forced stress by asking the patient personal questions that are intended to induce stress. After the personal question, a measurement is taken. The measurement strategy ensures that the stress in the person is recorded, and the change from one state to another is also recorded. This should also the impact of various stressors to be discretely analyzed.

Measurement Process: In order to take renal-pulse Doppler measurement in the intra-renal artery, the patient is asked to hold his breath. During this time, the technician focuses on the major artery and takes the measurement. After taking the measurement, the patient can breathe normally. As soon as the question is asked, the patient is again asked to hold his breath and another measurement is taken. This measurement process may be repeated up to five times and the average of the measurement is taken as the reading. The renal-pulse Doppler measurement is used to analyze renal vascular resistance. In the present equipment, a technician manually selects the peak and the trough from the pulse waveform. The machine then uses the peak and trough to calculate the resistive index (RI), which gives an indication of the renal vascular resistance (RVR). The resistive index is calculated from the peak systolic velocity and the lowest diastolic velocity. The peaks and troughs can be identified from the Doppler waveform. RI is equal to the peak systolic velocity (S) minus the lowest diastolic velocity (D), divided by the peak systolic velocity (S). Thus, $$RI = \frac{S-D}{S}.$$

The systolic-to-diastolic flow velocities ratio (S/D ratio) is the ratio of the systolic velocity peak and the diastolic velocity trough. Thus, $$S/D = \frac{1}{1-RI}.$$

The renal vascular resistance (RVR) is equal to the pressure difference of renal arterial blood pressure ($P_a$) minus renal venous blood pressure ($P_v$), divided by the renal blood flow (F). Thus, $$RVR = \frac{P_a - P_v}{F}.$$

The pulse Doppler can be taken over an area, which is properly focused. In order to focus the pulse Doppler, external movement should be eliminated. In particular, breathing can cause the kidneys to move up to a half-inch. Due to this movement, a pulse Doppler measurement cannot be taken accurately when the patient is breathing normally. Thus, the patient must hold his breath during the measurement. It is also important to focus the pulse Doppler on the major artery in the kidney for each measurement. The same artery must be used for each measurement because the RI can be different in different arteries. Also, the angle between the beam and the direction of blood flow should be minimized in order to increase the accuracy of the measurement. Furthermore, the measurement angle should be kept constant between measurements. Consequently, the location and angle of all measurements should be the same.

Patient History: The patient is 23-years old, with no smoking or drinking habits. There is no personal or family history of hypertension, heart disease, or kidney diseases. The patient has good analytical skills and relatively poor oral arithmetic skills.

Results:

State 1: The patient's RI was measured in a normal (baseline) state without any forced stress or relaxation. The patient's systolic-to-diastolic flow velocities ratio (S/D) was also measured. During this initial measurement, the patient reported that he was feeling stressed caused by anxiety over the trial as well as the feeling that time is being wasted by lying idle. The measurements in state 1 were:

| | So. No. | | | |
|---|---|---|---|---|
| | 1 | 2 | 3 | Average |
| RI | 0.61 | 0.64 | 0.61 | 0.62 |
| S/D Ratio | 2.56 | 2.79 | 2.57 | 2.64 |

State 2: The patient was subjected to forced relaxation by talking and telling jokes. The readings were then taken after every short event of forced relaxation. The patient reported that he was not relaxed by the forced relaxation and that he still felt the same as in state 1. The measurements in state 2 were:

| | So. No. | | | | |
|---|---|---|---|---|---|
| | 1 | 2 | 3 | 4 | Average |
| RI | 0.62 | 0.63 | 0.62 | 0.62 | 0.62 |
| S/D Ratio | 2.63 | 2.70 | 2.66 | 2.61 | 2.65 |

State 3: The patient was asked some simple arithmetic questions and measurements after asking the questions. Then the patient was asked to relax. The patient reported that he was feeling relaxed and that he was feeling less anxiety about the trial. Because the questions were relatively simple, the person was relaxed while answering. Then the patient was asked difficult arithmetic questions. The patient took more time to answer the difficult questions. The patient reported that the difficult question increased his stress because he was attempting to answer the difficult questions as quickly as he answered the simple questions. The patient was then asked to relax, however, this did not make the patient any more relaxed as he was already feeling relaxed. The measurements in state 3 were:

| | So. No. | | | | | | | | | | | | |
|---|---|---|---|---|---|---|---|---|---|---|---|---|---|
| | 1.1 | 1.2 | 1.3 | 2 | 3 | 4.1 | 4.2 | 4.3 | 4.4 | 5.1 | 5.2 | 5.3 | Average |
| RI | 0.57 | 0.51 | 0.48 | 0.62 | 0.67 | 0.59 | 0.55 | 0.50 | 0.54 | 0.53 | 0.51 | 0.50 | 0.55 |
| S/D Ratio | 2.33 | 2.06 | 1.94 | 2.61 | 2.80 | 2.46 | 2.25 | 2.00 | 2.18 | 2.11 | 2.02 | 2.00 | 2.22 |

State 4: The patient was asked some personal questions that were intended to cause stress. The patient reported feeling slightly stressed when answering the personal questions. However, the stressed varied question to question. For example, one question increased the patient's stress, while the last question actually relaxed the patient as he discussed a particular issue.

| | So. No. | | | | | |
|---|---|---|---|---|---|---|
| | 1 | 2 | 3 | 4 | 5 | Average |
| RI | 0.59 | 0.57 | 0.63 | 0.60 | 0.57 | 0.59 |
| S/D Ratio | 2.47 | 2.33 | 2.73 | 2.5 | 2.33 | 2.47 |

Summary of the Trial: The patient's pulse Doppler was measured in either the renal artery or intra-renal artery. Intra-renal artery is likely more responsive to stress, however is it also more sensitive to motion, making it more difficult to take an accurate measurement. The patient had to hold his breath for measurements to be taken, which was detrimental to the experiment. Thus for the further experiments, the main renal Doppler at the start of the renal artery was used. In main renal artery Doppler the measurement is taken from the renal artery at a location beneath stomach instead of at the kidney. Respiration causes less movement at this location, thus making it substantially easier to take measurements without making the patient hold his breath. Furthermore, relatively continuous measurements can be taken at this location, such that changes in RI and S/D ration can be measured effectively as soon as they occur.

Summary: Renal Doppler measurements were taken on the renal artery or intra-renal artery. For the intra-renal artery, the person needed to hold his breath for measurement. Peaks and troughs in the waveform were selected manually. Stress was induced by asking the patient mathematical and personal questions. Changes in RI correlated with the patient's self-reported stress level, such that RI increased with stress.

| State | Average RI | Inference |
|---|---|---|
| Normal | 0.62 | Initial anxious state. |
| Forced relaxation | 0.62 | No effect on stress level. |
| Mathematical Questions | 0.53 | RI decreased due to focus in mind. |
| Personal Questions | 0.59 | RI lower than normal state. |

Example 2

In this experiment, the measurement strategy remained the same as used in example 1. The only difference was that patient did not need to hold his breath during measurements. This second experiment aims to confirm the results of RI dependence on stress and observe if some other correlation is seen between the stress and renal blood flow. New Doppler equipment was used in this experiment which was able to automatically identify peaks and troughs in waveforms, allowing for more accurate measurements. The patient in this experiment was the same as from experiment 1. In this experiment, the person was asked questions continuously and only a brief time period was given to relax between each question. This allowed for measurement of the time needed for a person to recover from stress and particular stressors. This stress-recovery time is inversely proportional to the extent of compensatory mechanism of that person.

Results:

1. Baseline measurement (normal state): RI=0.65, 0.64.
2. After asking tough algebraic questions: RI=0.72, 0.70, 0.71.
3. After giving a brief time for relaxation: RI=0.61.
4. During and after asking the mathematical question: RI=0.70, 0.70, 0.71, 0.70, 0.72.
5. After giving a brief time for relaxation along with deep breathing exercise: RI=0.62, 0.62, 0.61.
6. Before asking analytical questions: RI=0.66.
7. Asking the analytical questions: RI=0.72, 0.69, 0.64, 0.66, 0.69, 0.74.
8. Asking the arithmetic questions: RI=0.74, 0.72, 0.73.
9. The person is asked to undergo self induced stress. RI=0.77, 0.81, 0.84.
10. Return to baseline measurement (normal state): RI=0.66, 0.69, and 0.72.

During the continuous measurements, it was observed that it took only 10-12 pulses for the patient to return to a normal (i.e. relaxed) state. This demonstrated the extent of the patient's compensatory mechanisms for dealing with stress. This also indicates that delays in making measurements may cause erroneous RI measurement. Consequently, measurements should be taken immediately after stress is induced.

The Doppler waveform varied with the patient's stress level. It was observed that the peaks in the waveform became sharper and the area under the peak decreased as the patient's stress increased.

When the patient was asked analytical questions (state 7), a good correlation was observed between the question asked and the RI increase. RI increased more with more difficult questions. It was also observed that RI increased just prior to or during question dictation. However, if the question was simple, the patient's RI would decrease immediately after the question was completed. This demonstrates that merely asking a question, regardless of the content of a question, may cause stress.

When the patient was asked to self-induce stress (state 9), the patient was instructing to think of a stressful past-experience or any probable stressful future-event. The patient then signaled once he felt stressed.

When the patient returned to a normal state (state 10), it was expected that the patient's RI would return to the level observed during the baseline measurement (state 1). This was not observed, however, likely because the person was asked to hold his breath during this final measurement, which may have cause the patient's stress and RI to increase.

The patient's average RI when relaxed was 0.62 and his average RI when stressed was 0.75. There is a significant difference of 21% in the average readings. There is also a difference of 38% in min value of relaxed and max value in stressed.

Summary: Renal Doppler measurements were taken on the main renal artery. The patient did not need to hold his breath. Peaks and troughs were selected automatically, and RI was also calculated automatically. This allowed for more accurate RI measurements than in experiment 1. Changes in RI correlated with the patient's self-reported stress level, such that RI increased with stress.

| State | Average RI | Inference |
|---|---|---|
| Normal | 0.64 | Initial state |
| Relaxed | 0.61 | RI decreased |
| Forced Relaxation | 0.62 | Deep breathing decreased RI and stress |
| Mathematical Questions | 0.71 | Increased RI confirms stress |
| Self-induced Stress | 0.81 | Large RI indicating high stress |

Example 3

The trial of example 2 was repeated on a new patient.

Measurement Strategy: The patient is asked to relax for some time. The patient is not told about the procedure or the type of questions that will be asked. The person is then asked some simple mathematical questions (e.g., addition and subtraction). The patient is then asked more complicated mathematical questions (e.g., multiplication and division). The patient is also asked some personal and job-related questions that are intended to induce stress. Renal Doppler measurements are taken continuously as the questions are asked.

Patient History: The patient is 35-years old, with no history of heart disease or kidney disease. The patient has poor mathematical skills. The patient did not complete the high school and is not fond of mathematics. The examining physician knew certain personal details about the patient.

Results:

1. Baseline measurement (normal state): RI=0.60, 0.62.
2. After asking tough mathematical questions: RI=0.67, 0.70.

3. After giving a brief time for relaxation: RI=0.62, 0.62.

4. During and after asking a more difficult mathematical question: RI=0.71.

5. The person was relaxed with some humorous talk: RI=0.71.

6. After asking simple arithmetic questions: RI=0.67, 0.56, 0.63, 0.47.

7. After asking stressful personal question by physician: RI=0.64, 0.69, 0.64, 0.66.

8. After giving time for relaxation: RI=0.59, 0.54.

9. After asking difficult arithmetic questions: RI=0.72, 0.63, 0.62, 0.65, 0.67, 0.66, 0.65.

10. Return to baseline measurement (normal state): RI=0.57.

The patient was subjected to most of the same stressors as the patient in experiment 2. Initially the patient reported that he was stressed due to the anxiety of the trial. The patients RI increased only slightly when he was asked mathematical questions. The patient answered many of the questions incorrectly. After the measurements, the patient was asked about how he was feeling during the trial and what were the instances when he felt stressed. The patient reported that the difficult mathematical questions were not stressful, though he stated that he tried his best to answer them.

When the patient was asked personal questions (state 7), his RI increased. The patient reported that the personal questions were stressful, especially in the beginning of that phase of questions. This confirmed that the personal questions stressed the patient. Though the patient's RI increased, the increase in RI was slight, in an absolute sense, compared to the initial values. This suggests that the analysis of stress should be based on a comparison of local values (i.e., by comparing the stressed state with the states immediately before and after the stressed state).

The patient's baseline stress consistently declined during the course of the experiment (see states 1, 3, 8, and 10), indicating that the patient was become more relaxed as the trial proceeded and as he became more comfortable and familiar with the process.

Summary: Renal Doppler measurements were taken on the main renal artery. The patient did not need to hold his breath. Peaks and troughs were selected automatically, and RI was also calculated automatically. The patient's subjective stress experience and feedback about the experiment were recorded. Changes in RI correlated with the patient's self-reported stress level, such that RI increased with stress.

| State | Average RI | Inference |
|---|---|---|
| Normal | 0.61 | Initial state; some anxiety of trial |
| Relaxed | 0.57 | RI decreased |
| Mathematical Questions | 0.69 | Increased RI indicates stress |
| Difficult Math Questions | 0.66 | RI decreased |
| Personal Questions | 0.66 | Local RI increase is high |

Conclusions from Examples 1-3

The hypothesis for these experiments was that would RI increase with stress and decrease with relaxation. This hypothesis was generally confirmed. In most cases it was observed that increasing RI correlated with increasing self-reported stress. However, in some cases RI decreased when the patient was subjected to forced stress. Similarly, in some cases RI increased when the patient was subjected to forced relaxation. It is likely that in these latter cases, the forced stress/relaxation was merely ineffective as inducing the expected response. For example, in experiment 1 the patient actually became more relaxed when asked arithmetic questions that were intended to induce stress, while asking the same patient to relax was ineffective at reducing his RI. This is likely because when the patient in experiment 1 began the trial in a stressed state, such that his normal (baseline) stated was substantially stressed. Consequently, the forced relaxation method using talking and jokes was not enough to bring the patient out of the initial stressed state.

Asking mathematical questions was effective at inducing stress in certain situation. A question that was relatively difficult for the patient to answer induced stress and an increase in RI was observed. However, a question that was relatively easy for the patient actually reduced the patient's stress and a decrease in RI was observed. Asking personal questions was also effective at inducing stress in patients, and the changes in RI caused by personal questions tended to be larger than the changes caused by mathematical question. Consequently, changes in RI correlated with the difficult of the question asked, such that RI increased with the difficulty of the question. Similarly, it was observed that more difficult questions had a larger (more positive) stress factor, such that the change in RI increased with the difficulty of the question.

It was also observed that the patients recovered from particular stressors relatively quickly, indicating that the patients had fast-acting compensatory mechanisms for dealing with stress induced by mathematical and personal questions. Similarly, it indicates that mathematical and personal questions are only capable of inducing short-term stress responses. This also indicates that renal Doppler measurements should be taken continuously when asking these types of questions in order to increase the accuracy of the measurements.

Factors that may decrease the accuracy of Doppler measurements include: (1) physical motion of the person, especially breathing when taking measurements on intra-renal artery; (2) having the patient hold his breath, which may itself be stressful; (3) variations in the Doppler measurement angle between measurements; (4) manual selection of peaks in troughs in Doppler waveforms, which may be dependent on the accuracy and experience of the operating technician; or (5) delays between the time stress is induced and when a measurement is taken, which may cause a smaller change in RI to be observed because of fast-acting compensatory mechanisms. These factors may have affected the measurements in experiment 1. However, these factors were effectively eliminated in experiments 2 and 3 using the following techniques: (1) minimizing the effect of physical motion, particularly breathing, by taking measurements on the main renal artery; (2) allowing the patient to breath normally while taking measurements; (3) using equipment that can automatically select the peaks and troughs in Doppler waveforms; and (5) taking measurements continuously. Consequently, the results of experiments 2 and 3 are likely more accurate than the results of experiment 1. However, the results of all three experiments support the hypothesis that RI increases with stress and decreases with relaxation.

In experiments 2 and 3, it was observed that the RI of a patient increased significantly just before each question was asked. This reflected the patient's anxiety over the pending question. After the question was completed, RI remained elevated for difficult questions while the patient attempted to solve the question. However, for easy questions, RI quickly decreased after the question was completed. The shape of the Doppler waveform clearly changed when questions were asked, making it simple to identify and distinguish stressed and relaxed stated. Interestingly, it was observed that RI increased the most when a patient was asked to self-induce stress. RI decreased the most when a patient was asked to relax by using deep-breathing techniques, thus validating deep-breathing as an effective stress-reduction therapy. However, merely asking a patient to relax may not decrease their RI, and may in fact cause an increase in RI.

While asking difficult questions generally increased a patient's stress, it was observed that asking questions that were too hard (i.e., beyond the patient's ability to answer correctly) did not cause stress. This may be because the patient realizes his inability to answer the question and gives up trying to solve the question, thereby avoiding a stress response. In experiment 3, the patient was initially stressed when asked difficult mathematical question, but his RI quickly dropped after the first question as the patient effectively gave up trying to solve the questions correctly. This correlated with the patient's report that he did not feel stressed when asked difficult mathematical questions that he generally could not solve.

Renal Doppler sonography provides a fast and reliable way to detect stress. However, the stress causing methodology is not normalized. Different patients reacted differently to the same type of questions. Thus the questionnaire should be prepared based on the particular patient. For example, mathematical questions should be scaled based on the patients education level. A common method of solving some mental questions works differently on different persons. The normal (baseline) state of patient also has a significant impact on their stress response.

In conclusion, renal Doppler sonography may be used to accurately measure stress in a person. There is a strong correlation between a patient's RI and a patient's self-reported stress level. The relationship between RI and stress may be used to generate and validate algorithms used for calculating a stress index and stress factors. Furthermore, RI and self-reported stress data can be combined with data from other sensors to generate a stress model of the patient that correlates a variety of physiological, psychological, behavioral, or environmental data of the patient with the stress or RI of the patient.

Example 4

In this experiment, physiological, psychological, behavioral, and environmental data is collected from multiple subjects. The subjects conduct their daily activities normally while various sensors continuously monitor them. The patients wear a blood-pressure monitor, an actigraph, a pulse oximeter, the iPod Touch described above, and a data aggregation system. All of these are portable devices that the subjects can carry. Also, periodically the subject's renal blood velocity, blood glucose level, and cortisol level is measured. The subjects can report psychological and behavioral data using an iPod Touch application, similar to mood sensor 400. The iPod Touch also has custom software to verify the operation of the sensors and the data aggregation system. During the experimental period, the subject is exposed to stress therapies (e.g., stress management and counseling).

Data is collected from ten normotensive subjects for at least four hours a day over the course of two weeks (10 working days). Of the four hours of data collection, approximately two hours of data will be collected while the subject is at work and two hours of data will be collected after work. During the first week of data collection, the patient only engages in light relaxation during the two-hour post-work period each day. During the second week of data collection the patient engaged in stress management counseling during the post-work period each day.

The data is used to develop a stress model for each patient. The stress model correlates the physiological, psychological, behavioral, and environmental data collected during the experiment with the stress or RI of the subject. The renal Doppler measurements for a patient are used to determine the stress index of the patient. The stress index is then correlated with the physiological, psychological, behavioral, and environmental data collected during the experiment. A stress model for calculating the stress index of a person as a function of with the physiological, psychological, behavioral, and environmental data is then determined. Thus, the renal Doppler measurements are effectively used to validate the stress model of the person.

Display

Display system 190 may render, visualize, display, message, and publish to one or more users based on the one or more analysis outputs from analysis system 180. In particular embodiments, one or more subjects of one or more sensors 112 may be a user of display system 190. An analysis output from analysis system 180 may be transmitted to display system 190 over any suitable medium. Display system 190 may include any suitable I/O device that can enable communication between a person and display system 190. As an example and not by way of limitation, display system 190 may include a video monitor, speaker, touch screen, printer, another suitable I/O device or a combination of two or more of these. Display system 190 may be any computing device with a suitable I/O device, such as computer system 1600.

In particular embodiments, display system 190 may comprise one or more local display systems 130 or one or more remote display systems 140. Where display system 190 comprises multiple subsystems (e.g., local display systems 130 and remote display systems 140), display of analysis outputs may occur on one or more subsystems. As an example and not by way of limitation, local display systems 130 and remote display systems 140 may present identical displays based on the analysis output. As another example and not by way of limitation, local display systems 130 and remote display systems 140 may present different displays based on the analysis output. In particular embodiments, a user-input sensor in sensor array 110 may also function as display system 190. Any client system with a suitable I/O device may serve as a user-input sensor and display system 190. As an example and not by way of limitation, a smart phone with a touch screen may function both as a user-input sensor and as display system 190.

In particular embodiments, display system 190 may display an analysis output in real-time as it is received from analysis system 180. In various embodiments, real-time analysis of data streams from sensor array 110 by analysis system 180 allows a user to receive real-time information about the health status of a subject. It is also possible for the user to receive real-time feedback from display system 190 (e.g., warnings about health risks, recommending therapies, etc.).

Although this disclosure describes a display system 190 performing particular display-related processes using particular techniques, this disclosure contemplates a display system 190 performing any suitable display-related processes using any suitable techniques.

In particular embodiments, display system 190 may render and visualize data based on analysis output from analysis system 180. Display system 190 may render and visualize using any suitable means, including computer system 1400 with a suitable I/O device, such as a video monitor, speaker, touch screen, printer, another suitable I/O device or a combination of two or more of these.

Rendering is the process of generating an image from a model. The model is a description of an object in a defined language or data structure. The description may contain color, size, orientation, geometry, viewpoint, texture, lighting, shading, and other object information. The rendering may be any suitable image, such as a digital image or raster graphics image. Rendering may be performed on any suitable computing device.

Visualization is the process of creating images, diagrams, or animations to communicate information to a user. Visualizations may include diagrams, images, objects, graphs, charts, lists, maps, text, etc. Visualization may be performed on any suitable device that may present information to a user, including a video monitor, speaker, touch screen, printer, another suitable I/O device or a combination of two or more of these.

In some embodiments, rendering may be performed partially on analysis system 180 and partially on display system 190. In other embodiments, rendering is completely performed on analysis system 180, while visualization is performed on display system 190.

In particular embodiments, display system 190 may message and publish data based on analysis output from analysis system 180. Display system 190 may message and publish using any suitable means, including email, instant message, text message, audio message, page, MMS text, social network message, another suitable messaging or publishing means, or a combination of two or more of these.

In particular embodiments, display system 190 may publish some or all of the analysis output such that the publication may be viewed by one or more third-parties. In one embodiment, display system 190 may automatically publish the analysis output to one or more websites. As an example and not by way of limitation, a subject of a GPS sensor (such as, for example, a smart phone) may automatically have his location published to a social networking site (such as, for example, Facebook, Twitter, or Foursquare).

In particular embodiments, display system 190 may send or message some or all of the analysis output to one or more third-parties. In one embodiment, display system 190 may automatically send the analysis output to one or more healthcare providers. As an example and not by way of limitation, a subject wearing a portable blood glucose monitor may have all of the data from that sensor transmitted to his doctor. In another embodiment, display system 190 will only send the analysis output to a healthcare provider when one or more threshold criteria are met. As an example and not by way of limitation, a subject wearing a portable blood glucose monitor may not have any data from that sensor transmitted to his doctor unless his blood glucose data shows that he is severely hypoglycemic (e.g., below 2.8 mmol/l). In particular embodiments, display system 190 may message one or more alerts to a user or third-party based on the analysis output. An alert may contain a notice, warning, or recommendation for the user or third-party. As an example and not by way of limitation, a subject wearing a blood glucose monitor may receive an alert if his blood glucose level shows that he is moderately hypoglycemic (e.g., below 3.5 mmol/l) warning of the hypoglycemia and recommending that he eat something.

In particular embodiments, display system 190 may display one or more therapies to a user based on analysis output from analysis system 180. A therapy may be a recommended therapy for the user or a therapeutic feedback that provide a direct therapeutic benefit to the user. Display system 190 may deliver a variety of therapies, such as interventions, biofeedback, breathing exercises, progressive muscle relaxation exercises, presentation of personal media (e.g., music, personal pictures, etc.), offering an exit strategy (e.g., calling the user so he has an excuse to leave a stressful situation), references to a range of psychotherapeutic techniques, and graphical representations of trends (e.g., illustrations of health metrics over time), cognitive reframing therapy, and other therapeutic feedbacks. Although this disclosure describes display system 190 delivering particular therapies, this disclosure contemplates display system 190 delivering any suitable therapies.

Systems and Methods

Figure 16:
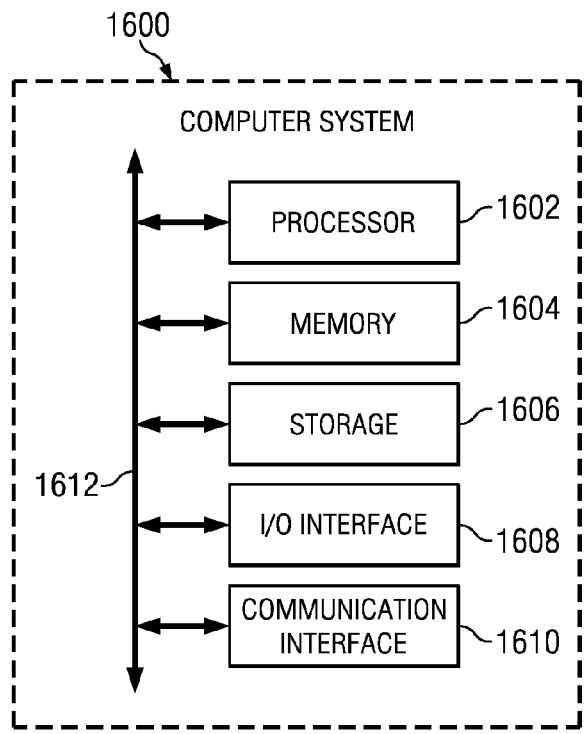
FIG. 16 illustrates an example computer system.

FIG. 16 illustrates an example computer system 1600. In particular embodiments, one or more computer systems 1600 perform one or more steps of one or more methods described or illustrated herein. In particular embodiments, one or more computer systems 1600 provide functionality described or illustrated herein. In particular embodiments, software running on one or more computer systems 1600 performs one or more steps of one or more methods described or illustrated herein or provides functionality described or illustrated herein. Particular embodiments include one or more portions of one or more computer systems 1600.

This disclosure contemplates any suitable number of computer systems 1600. This disclosure contemplates computer system 1600 taking any suitable physical form. As example and not by way of limitation, computer system 1600 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1600 may include one or more computer systems 1600; be unitary or distributed; span multiple locations; span multiple machines; span multiple data centers; or reside in a cloud, which may include one or more cloud components in one or more networks. Where appropriate, one or more computer systems 1600 may perform without substantial spatial or temporal limitation one or more steps of one or more methods described or illustrated herein. As an example and not by way of limitation, one or more computer systems 1600 may perform in real time or in batch mode one or more steps of one or more methods described or illustrated herein. One or more computer systems 1600 may perform at different times or at different locations one or more steps of one or more methods described or illustrated herein, where appropriate.

In particular embodiments, computer system 1600 includes a processor 1602, memory 1604, storage 1606, an input/output (I/O) interface 1608, a communication interface 1610, and a bus 1612. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1602 includes hardware for executing instructions, such as those making up a computer program. As an example and not by way of limitation, to execute instructions, processor 1602 may retrieve (or fetch) the instructions from an internal register, an internal cache, memory 1604, or storage 1606; decode and execute them; and then write one or more results to an internal register, an internal cache, memory 1604, or storage 1606. In particular embodiments, processor 1602 may include one or more internal caches for data, instructions, or addresses. This disclosure contemplates processor 1602 including any suitable number of any suitable internal caches, where appropriate. As an example and not by way of limitation, processor 1602 may include one or more instruction caches, one or more data caches, and one or more translation lookaside buffers (TLBs). Instructions in the instruction caches may be copies of instructions in memory 1604 or storage 1606, and the instruction caches may speed up retrieval of those instructions by processor 1602. Data in the data caches may be copies of data in memory 1604 or storage 1606 for instructions executing at processor 1602 to operate on; the results of previous instructions executed at processor 1602 for access by subsequent instructions executing at processor 1602 or for writing to memory 1604 or storage 1606; or other suitable data. The data caches may speed up read or write operations by processor 1602. The TLBs may speed up virtual-address translation for processor 1602. In particular embodiments, processor 1602 may include one or more internal registers for data, instructions, or addresses. This disclosure contemplates processor 1602 including any suitable number of any suitable internal registers, where appropriate. Where appropriate, processor 1602 may include one or more arithmetic logic units (ALUs); be a multi-core processor; or include one or more processors 1602. Although this disclosure describes and illustrates a particular processor, this disclosure contemplates any suitable processor.

In particular embodiments, memory 1604 includes main memory for storing instructions for processor 1602 to execute or data for processor 1602 to operate on. As an example and not by way of limitation, computer system 1600 may load instructions from storage 1606 or another source (such as, for example, another computer system 1600) to memory 1604. Processor 1602 may then load the instructions from memory 1604 to an internal register or internal cache. To execute the instructions, processor 1602 may retrieve the instructions from the internal register or internal cache and decode them. During or after execution of the instructions, processor 1602 may write one or more results (which may be intermediate or final results) to the internal register or internal cache. Processor 1602 may then write one or more of those results to memory 1604. In particular embodiments, processor 1602 executes only instructions in one or more internal registers or internal caches or in memory 1604 (as opposed to storage 1606 or elsewhere) and operates only on data in one or more internal registers or internal caches or in memory 1604 (as opposed to storage 1606 or elsewhere). One or more memory buses (which may each include an address bus and a data bus) may couple processor 1602 to memory 1604. Bus 1612 may include one or more memory buses, as described below. In particular embodiments, one or more memory management units (MMUs) reside between processor 1602 and memory 1604 and facilitate accesses to memory 1604 requested by processor 1602. In particular embodiments, memory 1604 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1604 may include one or more memories 1604, where appropriate. Although this disclosure describes and illustrates particular memory, this disclosure contemplates any suitable memory.

In particular embodiments, storage 1606 includes mass storage for data or instructions. As an example and not by way of limitation, storage 1606 may include an HDD, a floppy disk drive, flash memory, an optical disc, a magneto-optical disc, magnetic tape, or a Universal Serial Bus (USB) drive or a combination of two or more of these. Storage 1606 may include removable or non-removable (or fixed) media, where appropriate. Storage 1606 may be internal or external to computer system 1600, where appropriate. In particular embodiments, storage 1606 is non-volatile, solid-state memory. In particular embodiments, storage 1606 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1606 taking any suitable physical form. Storage 1606 may include one or more storage control units facilitating communication between processor 1602 and storage 1606, where appropriate. Where appropriate, storage 1606 may include one or more storages 1606. Although this disclosure describes and illustrates particular storage, this disclosure contemplates any suitable storage.

In particular embodiments, I/O interface 1608 includes hardware, software, or both providing one or more interfaces for communication between computer system 1600 and one or more I/O devices. Computer system 1600 may include one or more of these I/O devices, where appropriate. One or more of these I/O devices may enable communication between a person and computer system 1600. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1608 for them. Where appropriate, I/O interface 1608 may include one or more device or software drivers enabling processor 1602 to drive one or more of these I/O devices. I/O interface 1608 may include one or more I/O interfaces 1608, where appropriate. Although this disclosure describes and illustrates a particular I/O interface, this disclosure contemplates any suitable I/O interface.

In particular embodiments, communication interface 1610 includes hardware, software, or both providing one or more interfaces for communication (such as, for example, packet-based communication) between computer system 1600 and one or more other computer systems 1600 or one or more networks. As an example and not by way of limitation, communication interface 1610 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1610 for it. As an example and not by way of limitation, computer system 1600 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1600 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1600 may include any suitable communication interface 1610 for any of these networks, where appropriate. Communication interface 1610 may include one or more communication interfaces 1610, where appropriate. Although this disclosure describes and illustrates a particular communication interface, this disclosure contemplates any suitable communication interface.

In particular embodiments, bus 1612 includes hardware, software, or both coupling components of computer system 1600 to each other. As an example and not by way of limitation, bus 1612 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCI-X) bus, a serial advanced technology attachment (SATA) bus, a Video Electronics Standards Association local (VLB) bus, or another suitable bus or a combination of two or more of these. Bus 1612 may include one or more buses 1612, where appropriate. Although this disclosure describes and illustrates a particular bus, this disclosure contemplates any suitable bus or interconnect.

Herein, reference to a computer-readable storage medium encompasses one or more non-transitory, tangible computer-readable storage media possessing structure. As an example and not by way of limitation, a computer-readable storage medium may include a semiconductor-based or other integrated circuit (IC) (such, as for example, a field-programmable gate array (FPGA) or an application-specific IC (ASIC)), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. Herein, reference to a computer-readable storage medium excludes any medium that is not eligible for patent protection under 35 U.S.C. §101. Herein, reference to a computer-readable storage medium excludes transitory forms of signal transmission (such as a propagating electrical or electromagnetic signal per se) to the extent that they are not eligible for patent protection under 35 U.S.C. §101. A computer-readable non-transitory storage medium may be volatile, non-volatile, or a combination of volatile and non-volatile, where appropriate.

This disclosure contemplates one or more computer-readable storage media implementing any suitable storage. In particular embodiments, a computer-readable storage medium implements one or more portions of processor 1602 (such as, for example, one or more internal registers or caches), one or more portions of memory 1604, one or more portions of storage 1606, or a combination of these, where appropriate. In particular embodiments, a computer-readable storage medium implements RAM or ROM. In particular embodiments, a computer-readable storage medium implements volatile or persistent memory. In particular embodiments, one or more computer-readable storage media embody software. Herein, reference to software may encompass one or more applications, bytecode, one or more computer programs, one or more executables, one or more instructions, logic, machine code, one or more scripts, or source code, and vice versa, where appropriate. In particular embodiments, software includes one or more application programming interfaces (APIs). This disclosure contemplates any suitable software written or otherwise expressed in any suitable programming language or combination of programming languages. In particular embodiments, software is expressed as source code or object code. In particular embodiments, software is expressed in a higher-level programming language, such as, for example, C, Perl, or a suitable extension thereof. In particular embodiments, software is expressed in a lower-level programming language, such as assembly language (or machine code). In particular embodiments, software is expressed in JAVA. In particular embodiments, software is expressed in Hyper Text Markup Language (HTML), Extensible Markup Language (XML), or other suitable markup language.

Figure 17:
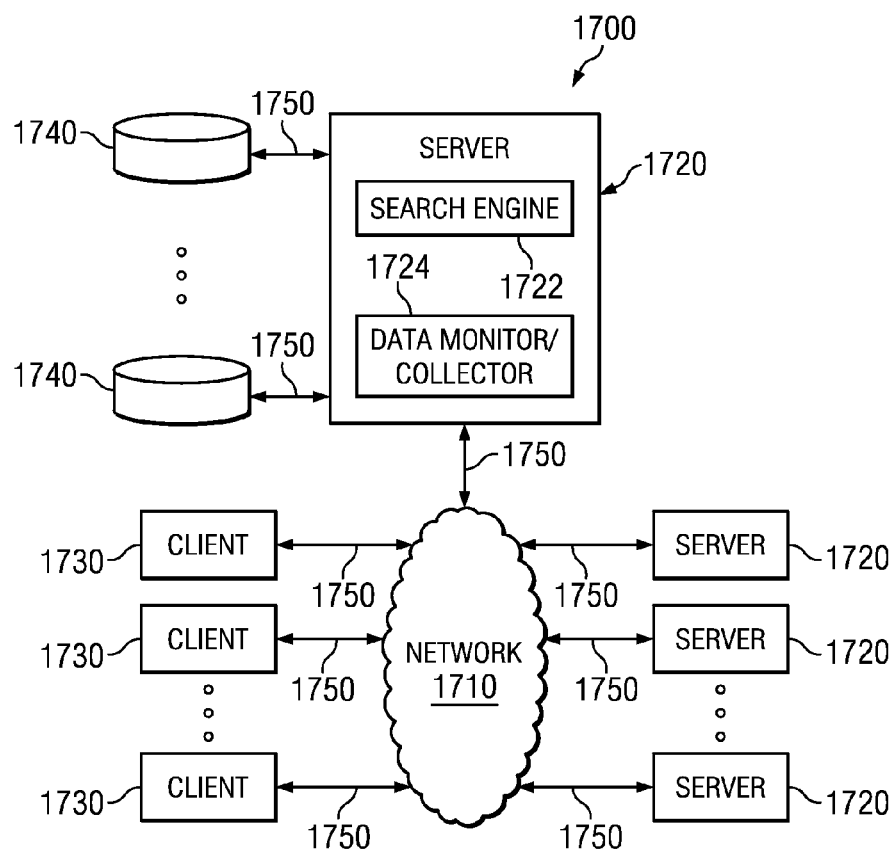
FIG. 17 illustrates an example network environment.

FIG. 17 illustrates an example network environment 1700. This disclosure contemplates any suitable network environment 1700. As an example and not by way of limitation, although this disclosure describes and illustrates a network environment 1700 that implements a client-server model, this disclosure contemplates one or more portions of a network environment 1700 being peer-to-peer, where appropriate. Particular embodiments may operate in whole or in part in one or more network environments 1700. In particular embodiments, one or more elements of network environment 1700 provide functionality described or illustrated herein. Particular embodiments include one or more portions of network environment 1700. Network environment 1700 includes a network 1710 coupling one or more servers 1720 and one or more clients 1730 to each other. This disclosure contemplates any suitable network 1710. As an example and not by way of limitation, one or more portions of network 1710 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 1710 may include one or more networks 1710.

Links 1750 couple servers 1720 and clients 1730 to network 1710 or to each other. This disclosure contemplates any suitable links 1750. As an example and not by way of limitation, one or more links 1750 each include one or more wireline (such as, for example, Digital Subscriber Line (DSL) or Data Over Cable Service Interface Specification (DOCSIS)), wireless (such as, for example, Wi-Fi or Worldwide Interoperability for Microwave Access (WiMAX)) or optical (such as, for example, Synchronous Optical Network (SONET) or Synchronous Digital Hierarchy (SDH)) links 1750. In particular embodiments, one or more links 1750 each includes an intranet, an extranet, a VPN, a LAN, a WLAN, a WAN, a MAN, a communications network, a satellite network, a portion of the Internet, or another link 1750 or a combination of two or more such links 1750. Links 1750 need not necessarily be the same throughout network environment 1700. One or more first links 1750 may differ in one or more respects from one or more second links 1750.

This disclosure contemplates any suitable servers 1720. As an example and not by way of limitation, one or more servers 1720 may each include one or more advertising servers, applications servers, catalog servers, communications servers, database servers, exchange servers, fax servers, file servers, game servers, home servers, mail servers, message servers, news servers, name or DNS servers, print servers, proxy servers, sound servers, standalone servers, web servers, or web-feed servers. In particular embodiments, a server 1720 includes hardware, software, or both for providing the functionality of server 1720. As an example and not by way of limitation, a server 1720 that operates as a web server may be capable of hosting websites containing web pages or elements of web pages and include appropriate hardware, software, or both for doing so. In particular embodiments, a web server may host HTML or other suitable files or dynamically create or constitute files for web pages on request. In response to a Hyper Text Transfer Protocol (HTTP) or other request from a client 1730, the web server may communicate one or more such files to client 1730. As another example, a server 1720 that operates as a mail server may be capable of providing e-mail services to one or more clients 1730. As another example, a server 1720 that operates as a database server may be capable of providing an interface for interacting with one or more data stores (such as, for example, data stores 1740 described below). Where appropriate, a server 1720 may include one or more servers 1720; be unitary or distributed; span multiple locations; span multiple machines; span multiple datacenters; or reside in a cloud, which may include one or more cloud components in one or more networks.

In particular embodiments, one or more links 1750 may couple a server 1720 to one or more data stores 1740. A data store 1740 may store any suitable information, and the contents of a data store 1740 may be organized in any suitable manner. As an example and not by way or limitation, the contents of a data store 1740 may be stored as a dimensional, flat, hierarchical, network, object-oriented, relational, XML, or other suitable database or a combination or two or more of these. A data store 1740 (or a server 1720 coupled to it) may include a database-management system or other hardware or software for managing the contents of data store 1740. The database-management system may perform read and write operations, delete or erase data, perform data deduplication, query or search the contents of data store 1740, or provide other access to data store 1740.

In particular embodiments, one or more servers 1720 may each include one or more search engines 1722. A search engine 1722 may include hardware, software, or both for providing the functionality of search engine 1722. As an example and not by way of limitation, a search engine 1722 may implement one or more search algorithms to identify network resources in response to search queries received at search engine 1722, one or more ranking algorithms to rank identified network resources, or one or more summarization algorithms to summarize identified network resources. In particular embodiments, a ranking algorithm implemented by a search engine 1722 may use a machine-learned ranking formula, which the ranking algorithm may obtain automatically from a set of training data constructed from pairs of search queries and selected Uniform Resource Locators (URLs), where appropriate.

In particular embodiments, one or more servers 1720 may each include one or more data monitors/collectors 1724. A data monitor/collection 1724 may include hardware, software, or both for providing the functionality of data collector/collector 1724. As an example and not by way of limitation, a data monitor/collector 1724 at a server 1720 may monitor and collect network-traffic data at server 1720 and store the network-traffic data in one or more data stores 1740. In particular embodiments, server 1720 or another device may extract pairs of search queries and selected URLs from the network-traffic data, where appropriate.

This disclosure contemplates any suitable clients 1730. A client 1730 may enable a user at client 1730 to access or otherwise communicate with network 1710, servers 1720, or other clients 1730. As an example and not by way of limitation, a client 1730 may have a web browser, such as MICROSOFT INTERNET EXPLORER or MOZILLA FIREFOX, and may have one or more add-ons, plug-ins, or other extensions, such as GOOGLE TOOLBAR or YAHOO TOOLBAR. A client 1730 may be an electronic device including hardware, software, or both for providing the functionality of client 1730. As an example and not by way of limitation, a client 1730 may, where appropriate, be an embedded computer system, an SOC, an SBC (such as, for example, a COM or SOM), a desktop computer system, a laptop or notebook computer system, an interactive kiosk, a mainframe, a mesh of computer systems, a mobile telephone, a PDA, a netbook computer system, a server, a tablet computer system, or a combination of two or more of these. Where appropriate, a client 1730 may include one or more clients 1730; be unitary or distributed; span multiple locations; span multiple machines; span multiple datacenters; or reside in a cloud, which may include one or more cloud components in one or more networks.

Miscellaneous

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context. Furthermore, "a", "an," or "the" is intended to mean "one or more," unless expressly indicated otherwise or indicated otherwise by context. Therefore, herein, "an A" or "the A" means "one or more A," unless expressly indicated otherwise or indicated otherwise by context.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, this disclosure encompasses any suitable combination of one or more features from any example embodiment with one or more features of any other example embodiment herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

REFERENCES

Albrecht, P., & Cohen, R. J. (1988). Estimation of heart rate power spectrum bands from real-world data. In Proceedings of computers in cardiology 1988 (pp. 311-314). IEEE.

Bernardi, L., Wdowczyk-Szulc, J., Valenti, C., Castoldi, S., Passino, C., Spadacini, G., et al. (2000, May). Effects of controlled breathing, mental activity and mental stress with or without verbalization on heart rate variability. J. Am. Coll. Cardiol., 35, 1462-1469.

Bigger, J. T., Jr., Fleiss, J. L., Steinman, R. C., Rolnitzky, L. M., Kleiger, R. E., & Rottman, J. N. (1992). Frequency domain measure of heart period variability and mortality after myocardial infarction. Circulation, 85, 164-171. Available from http://circ.ahajournals.org/cgi/reprint/85/1/164.

Clifford, G. D. (2002). Signal processing methods for heart rate variability. Unpublished doctoral dissertation.

Dikecligil, G. N., & Mujica-Parodi, L. R. (2010, June). Ambulatory and challenge-associated heart rate variability measures predict cardiac responses to real-world acute emotional stress. Biol. Psychiatry, 67, 1185-1190.

Egelund, N. (1982, July). Spectral analysis of heart rate variability as an indicator of driver fatigue. Ergonomics, 25, 663-672.

Filaire, E., Portier, H., Massart, A., Ramat, L., & Teixeira, A. (2010, March). Effect of lecturing to 200 students on heart rate variability and alpha-amylase activity. Eur. J. Appl. Physiol., 108, 1035-1043.

Hjortskov, N., Rissen, D., Blangsted, A. K., Fallentin, N., Lundberg, U., & Søgaard, K. (2004, June). The effect of mental stress on heart rate variability and blood pressure during computer work. Eur. J. Appl. Physiol., 92, 84-89.

Langelotz, C., Scharfenberg, M., Haase, O., & Schwenk, W. (2008, August). Stress and heart rate variability in surgeons during a 24-hour shift. Arch Surg, 143, 751-755.

Pagani, M., Lombardi, F., Guzzetti, S., Rimoldi, O., Furlan, R., Pizzinelli, P., et al. (1986). Power spectral analysis of heart rate and arterial pressure variabilities as a marker of sympathovagal interaction in man and conscious dog. Circulation Research., 59, 178-193. Available from http://circres.ahajournals.org/cgi/content/short/59/2/178.

Parati, G., Saul, J. P., Reinzo, M. D., & Mancia, G. (1995). Spectral analysis of blood pressure and heart rate variability in evaluating cardiovascular regulation. Hypertension, 25, 1276-1286. Available from http://hyper.ahajournals.org/cgi/content/full/25/6/1276.

Rottman, J. N., Steinman, R. C., Albrecht, P., Bigger, J. T., Jr., RoInitzky, L. M., & Fleiss, J. L. (1990). Efficient estimation of the heart period power spectrum suitable for physiologic or pharmacologic studies. American Journal of Cardiology, 66(20), 1522-1524.

Russoniello, C. V., O'Brien, K., & Parks, J. M. (2009). EEG, HRV and psychological correlates while playing Bejeweled II: A randomized controlled study. Stud Health Technol Inform, 144, 189-92. Available from http://www-.biomedsearch.com/nih/EEG-HRV-Psychological-Correlates-while/19592761.html Salahuddin, L., & Kim, D. (2006). Detection of acute stress by heart rate variability using a prototype mobile ECG sensor. Hybrid Information Technology, International Conference on, 2, 453-459.

Vempati, R. P., & Telles, S. (2000). Baseline occupational stress levels and physiological responses to a two day stress management program. Journal of Indian Psychology, 18(1), 33-37.

Wikipedia. (2010). Autonomic nervous system—Wikipedia, the free encyclopedia. Available from http://en.wikipedia.org/wiki/Autonomic nervous system.

Wikipedia. (2010). Kidney—Wikipedia, the free encyclopedia. Available from http://en.wikipedia.org/wiki/kidney.

Yang, H. K., Lee, J. W., Lee, K. H., Lee, Y. J., Kim, K. S., Choi, H. J., et al. (2008). Application for the wearable heart activity monitoring system: analysis of the autonomic function of HRV. Conf Proc IEEE Eng Med Biol Soc, 2008, 1258-1261.

All patent and literature references cite herein are incorporated by reference as if fully set forth.

What is claimed is:

1. A method for querying for self-reported mood or behavior data based on physiological sensor input comprising, one or more processors, associated with one or more computing devices, accessing one or more physiological data streams from one or more physiological sensors, the physiological data streams comprising physiological data of a person, the physiological data comprising at least renal-Doppler data, and one or more of heart-rate data, blood-pressure data, pulse-oximetry data, or accelerometer data;

the one or more of the processors accessing a stress model comprising baseline renal-Doppler data, and one or more of baseline heart-rate data of the person, baseline blood-pressure data of the person, baseline pulse-oximetry data of the person, or baseline accelerometer data of the person, wherein the baseline renal-Doppler data measures a stress response of the sympathetic nervous system, and the stress model correlates the baseline renal-Doppler data of the person with one or more of the baseline heart-rate data of the person, the baseline blood-pressure data of the person, the baseline pulse-oximetry data of the person, or the baseline accelerometer data of the person;

the one or more of the processors analyzing each physiological data stream in reference to a corresponding set of control parameters to determine whether one or more of the physiological data streams deviates from the set of control parameters, the set of control parameters being based on the stress model; and the one or more of the processors transmitting a query to a client system of the person if at least one of the physiological data streams deviates from its corresponding set of control parameters, wherein the query prompts the person to input self-reported mood data of the person or self-reported behavioral data of the person.

2. The method of claim 1, further comprising:
the one or more processors receiving one or more non-physiological data streams from one or more of the mood sensor or the behavioral sensor in response to the query, the non-physiological data streams comprising one or more self-reported mood data of the person or elf-reported behavioral data of the person.

3. The method of claim 1, further comprising:
the one or more processors analyzing each physiological data stream to identify an operating range for the sensor; and
the one or more processors generating for each physiological data stream the corresponding set of control parameters based on the operating range of the sensors.

4. The method of claim 1, further comprising:
the one or more processors accessing one or more environmental data streams from one or more environmental sensors, the environmental data streams comprising environmental data;
the one or more processors analyzing each environmental data stream in reference to a corresponding set of control parameters;
if at least one of the environmental data streams deviates from its corresponding set of control parameters, then transmitting a query to one or more of a mood sensor or a behavioral sensor for self-reported mood data of the person or self-reported behavioral data of the person.

5. The method of claim 4, wherein one or more of the environmental sensors comprises a barometer, a weather sensor, a pollen counter, a location sensor, a seismometer, an altimeter, a hydrometer, a decibel meter, a light meter, a thermometer, a wind sensor, or a traffic sensor.

6. The method of claim 4, wherein one or more of the environmental sensors is a physiological sensor configured to be affixed to a second person.

7. The method of claim 4, wherein one or more of the environmental sensors is a data feed.

8. The method of claim 7, wherein the data feed is selected from a group consisting of a stock-market ticker, a weather report, a news feed, a traffic-condition update, a public-health notice, an electronic calendar, and a social network news feed.

9. The method of claim 1, further comprising:
the one or more processors transmitting a query to an environment sensor for environmental data.

10. The method of claim 1, wherein one or more of the physiological sensors is configured to be affixed to the person's body.

11. The method of claim 1, wherein the control parameters specify one or more of a set point for the sensor, an operating range for the sensor, an operating threshold for the sensor, a sampling rate for the sensor, or a sample size for the sensor.

12. The method of claim 1, wherein the physiological sensors comprise one or more of a heart-rate monitor, a blood-pressure monitor, a pulse oximeter, or an accelerometer, and the physiological data streams comprise one or more of heart-rate data of the person from the heart-rate monitor, blood-pressure data of the person from the blood-pressure monitor, pulse oximetry data of the person from the pulse oximeter, or accelerometer data of the person from the accelerometer.

13. The method of claim 1, wherein:
the physiological sensors further comprise an electrocardiograph; and
the physiological data streams further comprise electrocardiograph data of the person from the electrocardiograph.

14. The method of claim 1, wherein:
the physiological sensors further comprise a glucocorticoid meter; and
the physiological data streams further comprise glucocorticoid data of the person from the glucocorticoid meter.

15. The method of claim 1, wherein:
the physiological sensors further comprise an electromyograph; and
the physiological data streams further comprise electromyograph data of the person from the electromyograph.

16. The method of claim 1, wherein:
the physiological sensors further comprise a respiration sensor; and
the data streams further comprise respiration data of the person from the respiration sensor.

17. The method of claim 1, wherein:
the physiological sensors further comprise a galvanic-skin-response sensor; and
the data streams further comprise galvanic-skin-response data of the person from the galvanic-skin-response sensor.

18. An apparatus for querying for self-reported mood or behavior data based on physiological sensor input comprising: one or more processors; and a memory coupled to the processors comprising instructions executable by the processors, the processors operable when executing the instructions to:
access one or more physiological data streams from one or more physiological sensors, the physiological data streams comprising physiological data of a person, the physiological data comprising at least renal-Doppler data, and one or more of heart-rate data, blood-pressure data, pulse-oximetry data, or accelerometer data;
access a stress model comprising baseline renal-Doppler data, and one or more of baseline heart-rate data of the person, baseline blood-pressure data of the person, baseline pulse-oximetry data of the person, or baseline accelerometer data of the person, wherein the baseline renal-Doppler data measures a stress response of the sympathetic nervous system, and the stress model correlates the baseline renal-Doppler data of the person with one or more of the baseline heart-rate data of the person, the baseline blood-pressure data of the person, the baseline pulse-oximetry data of the person, or the baseline accelerometer data of the person;
analyze each physiological data stream in reference to a corresponding set of control parameters to determine whether one or more of the physiological data streams deviates from the set of control parameters, the set of control parameters being based on the stress model; and
transmit a query to one or more of a mood sensor or a behavioral sensor for self-reported mood data of the person or self-reported behavioral data of the person if at least one of the physiological data streams deviates from its corresponding set of control parameters, wherein the query prompts the person to input self-reported mood data of the person or self-reported behavioral data of the person.

19. The apparatus of claim 18, the apparatus further operable when executing instructions to:
receive one or more non-physiological data streams from one or more of the mood sensor or the behavioral sensor in response to the query, the non-physiological data streams comprising one or more of self-reported mood data of the person or self-reported behavioral data of the person.

20. The apparatus of claim 18, the apparatus further operable when executing instructions to:
analyze each physiological data stream to identify an operating range for the sensor; and
generate for each physiological data stream the corresponding set of control parameters based on the operating range of the sensors.

21. The apparatus of claim 18, the apparatus further operable when executing instructions to:
access one or more environmental data streams from one or more environmental sensors, the environmental data streams comprising environmental data;
analyze each environmental data stream in reference to a corresponding set of control parameters;
if at least one of the environmental data streams deviates from its corresponding set of control parameters, then transmit a query to one or more of a mood sensor or a behavioral sensor for self-reported mood data of the person or self-reported behavioral data of the person.

22. The apparatus of claim 21, wherein one or more of the environmental sensors comprises a barometer, a weather sensor, a pollen counter, a location sensor, a seismometer, an altimeter, a hydrometer, a decibel meter, a light meter, a thermometer, a wind sensor, or a traffic sensor.

23. The apparatus of claim 21, wherein one or more of the environmental sensors is a physiological sensor configured to be affixed to a second person.

24. The apparatus of claim 21, wherein one or more of the environmental sensors is a data feed.

25. The apparatus of claim 24, wherein the data feed is selected from a group consisting of a stock-market ticker, a weather report, a news feed, a traffic-condition update, a public-health notice, an electronic calendar, and a social network news feed.

26. The apparatus of claim 18, the apparatus further operable when executing instructions to:
transmit a query to an environment sensor for environmental data.

27. The apparatus of claim 18, wherein one or more of the physiological sensors is configured to be affixed to the person's body.

28. The apparatus of claim 18, wherein the control parameters specify one or more of a set point for the sensor, an operating range for the sensor, an operating threshold for the sensor, a sampling rate for the sensor, or a sample size for the sensor.

29. The apparatus of claim 18, wherein the physiological sensors comprise one or more of a heart-rate monitor, a blood-pressure monitor, a pulse oximeter, or an accelerometer, and the physiological data streams comprise one or more of heart-rate data of the person from the heart-rate monitor, blood-pressure data of the person from the blood-pressure monitor, pulse oximetry data of the person from the pulse oximeter, or accelerometer data of the person from the accelerometer.

30. The apparatus of claim 18, wherein:
the physiological sensors further comprise an electrocardiograph; and
the physiological data streams further comprise electrocardiograph data of the person from the electrocardiograph.

31. The apparatus of claim 18, wherein:
the physiological sensors further comprise a glucocorticoid meter; and
the physiological data streams further comprise glucocorticoid data of the person from the glucocorticoid meter.

32. The apparatus of claim 18, wherein:
the physiological sensors further comprise an electromyograph; and
the physiological data streams further comprise electromyograph data of the person from the electromyograph.

33. The apparatus of claim 18, wherein:
the physiological sensors further comprise a respiration sensor; and
the data streams further comprise respiration data of the person from the respiration sensor.

34. The apparatus of claim 18, wherein:
the physiological sensors further comprise a galvanic-skin-response sensor; and
the data streams further comprise galvanic-skin-response data of the person from the galvanic-skin-response sensor.

35. One or more computer-readable non-transitory storage media embodying software for querying for self-reported mood or behavior data based on physiological sensor input that is operable when executed to:
access one or more physiological data streams from one or more physiological sensors, the physiological data streams comprising physiological data of a person, the physiological data comprising at least renal-Doppler data, and one or more of heart-rate data, blood-pressure data, pulse-oximetry data, or accelerometer data;
access a stress model comprising baseline renal-Doppler data, and one or more of baseline heart-rate data of the person, baseline blood-pressure data of the person, baseline pulse-oximetry data of the person, or baseline accelerometer data of the person, wherein the baseline renal-Doppler data measures a stress response of the sympathetic nervous system, and the stress model correlates the baseline renal-Doppler data of the person with one or more of the baseline heart-rate data of the person, the baseline blood-pressure data of the person, the baseline pulse-oximetry data of the person, or the baseline accelerometer data of the person;
analyze each physiological data stream in reference to a corresponding set of control parameters to determine whether one or more of the physiological data streams deviates from the set of control parameters, the set of control parameters being based on the stress model; and
transmit a query to one or more of a mood sensor or a behavioral sensor for self-reported mood data of the person or self-reported behavioral data of the person if at least one of the physiological data streams deviates from its corresponding set of control parameters, wherein the query prompts the person to input self-reported mood data of the person or self-reported behavioral data of the person.

36. The media of claim 35, the media embodying instructions further operable when executed to:
receive one or more non-physiological data streams from one or more of the mood sensor or the behavioral sensor in response to the query, the non-physiological data streams comprising one or more of self-reported mood data of the person or self-reported behavioral data of the person.

37. The media of claim 35, the media embodying instructions further operable when executed to:
analyze each physiological data stream to identify an operating range for the sensor; and
generate for each physiological data stream the corresponding set of control parameters based on the operating range of the sensors.

38. The media of claim 35, the media embodying instructions further operable when executed to:
access one or more environmental data streams from one or more environmental sensors, the environmental data streams comprising environmental data;
analyze each environmental data stream in reference to a corresponding set of control parameters;
if at least one of the environmental data streams deviates from its corresponding set of control parameters, then transmit a query to one or more of a mood sensor or a behavioral sensor for self-reported mood data of the person or self-reported behavioral data of the person.

39. The media of claim 38, wherein one or more of the environmental sensors comprises a barometer, a weather sensor, a pollen counter, a location sensor, a seismometer, an altimeter, a hydrometer, a decibel meter, a light meter, a thermometer, a wind sensor, or a traffic sensor.

40. The media of claim 38, wherein one or more of the environmental sensors is a physiological sensor configured to be affixed to a second person.

41. The media of claim 38, wherein one or more of the environmental sensors is a data feed.

42. The media of claim 41, wherein the data feed is selected from a group consisting of a stock-market ticker, a weather report, a news feed, a traffic-condition update, a public-health notice, an electronic calendar, and a social network news feed.

43. The media of claim 35, the media embodying instructions further operable when executed to:
transmit a query to an environment sensor for environmental data.

44. The media of claim 35, wherein one or more of the physiological sensors is configured to be affixed to the person's body.

45. The media of claim 35, wherein the control parameters specify one or more of a set point for the sensor, an operating range for the sensor, an operating threshold for the sensor, a sampling rate for the sensor, or a sample size for the sensor.

46. The media of claim 35, wherein the physiological sensors comprise one or more of a heart-rate monitor, a blood-pressure monitor, a pulse oximeter, or an accelerometer, and the physiological data streams comprise one or more of heart-rate data of the person from the heart-rate monitor, blood-pressure data of the person from the blood-pressure monitor, pulse oximetry data of the person from the pulse oximeter, or accelerometer data of the person from the accelerometer.

47. The media of claim 35, wherein:
the physiological sensors further comprise an electrocardiograph; and
the physiological data streams further comprise electrocardiograph data of the person from the electrocardiograph.

48. The media of claim 35, wherein:
the physiological sensors further comprise a glucocorticoid meter; and
the physiological data streams further comprise glucocorticoid data of the person from the glucocorticoid meter.

49. The media of claim 35, wherein:
the physiological sensors further comprise an electromyograph; and
the physiological data streams further comprise electromyograph data of the person from the electromyograph.

50. The media of claim 35, wherein:
the physiological sensors further comprise a respiration sensor; and
the data streams further comprise respiration data of the person from the respiration sensor.

51. The media of claim 35, wherein:
the physiological sensors further comprise a galvanic-skin-response sensor; and
the data streams further comprise galvanic-skin-response data of the person from the galvanic-skin-response sensor.

52. A system for querying for self-reported mood or behavior data based on physiological sensor input comprising:
means for accessing one or more physiological data streams from one or more physiological sensors, the physiological data streams comprising physiological data of a person, the physiological data comprising at least renal-Doppler data, and one or more of heart-rate data, blood-pressure data, pulse-oximetry data, or accelerometer data;
means for accessing a stress model comprising baseline renal-Doppler data, and one or more of baseline heart-rate data of the person, baseline blood-pressure data of the person, baseline pulse-oximetry data of the person, or baseline accelerometer data of the person, wherein the baseline renal-Doppler data measures a stress response of the sympathetic nervous system, and the stress model correlates the baseline renal-Doppler data of the person with one or more of the baseline heart-rate data of the person, the baseline blood-pressure data of the person, the baseline pulse-oximetry data of the person, or the baseline accelerometer data of the person;
means for analyzing each physiological data stream in reference to a corresponding set of control parameters to determine whether one or more of the physiological data streams deviates from the set of control parameters, the set of control parameters being based on the stress model; and
means for transmitting a query to a client system of the person if at least one of the physiological data streams deviates from its corresponding set of control parameters, wherein the query prompts the person to input self-reported mood data of the person or self-reported behavioral data of the person.

53. The system of claim 52, further comprising:
means for receiving one or more non-physiological data streams from one or more of the mood sensor or the behavioral sensor in response to the query, the non-physiological data streams comprising one or more of self-reported mood data of the person or self-reported behavioral data of the person.

54. The system of claim 52, further comprising:
means for analyzing each physiological data stream to identify an operating range for the sensor; and
means for generating for each physiological data stream the corresponding set of control parameters based on the operating range of the sensors.

55. The system of claim 52, further comprising:
means for accessing one or more environmental data streams from one or more environmental sensors, the environmental data streams comprising environmental data;
means for analyzing each environmental data stream in reference to a corresponding set of control parameters;
if at least one of the environmental data streams deviates from its corresponding set of control parameters, then means for transmitting a query to one or more of a mood sensor or a behavioral sensor for self-reported mood data of the person or self-reported behavioral data of the person.

56. The system of claim 55, wherein one or more of the environmental sensors comprises a barometer, a weather sensor, a pollen counter, a location sensor, a seismometer, an altimeter, a hydrometer, a decibel meter, a light meter, a thermometer, a wind sensor, or a traffic sensor.

57. The system of claim 55, wherein one or more of the environmental sensors is a physiological sensor configured to be affixed to a second person.

58. The system of claim 55, wherein one or more of the environmental sensors is a data feed.

59. The system of claim 58, wherein the data feed is selected from a group consisting of a stock-market ticker, a weather report, a news feed, a traffic-condition update, a public-health notice, an electronic calendar, and a social network news feed.

60. The system of claim 52, further comprising:
means for transmitting a query to an environment sensor for environmental data.

61. The system of claim 52, wherein one or more of the physiological sensors is configured to be affixed to the person's body.

62. The system of claim 52, wherein the control parameters specify one or more of a set point for the sensor, an operating range for the sensor, an operating threshold for the sensor, a sampling rate for the sensor, or a sample size for the sensor.

63. The system of claim 52, wherein the physiological sensors comprise one or more of a heart-rate monitor, a blood-pressure monitor, a pulse oximeter, or an accelerometer, and the physiological data streams comprise one or more of heart-rate data of the person from the heart-rate monitor, blood-pressure data of the person from the blood-pressure monitor, pulse oximetry data of the person from the pulse oximeter, or accelerometer data of the person from the accelerometer.

64. The system of claim 52, wherein:
the physiological sensors further comprise an electrocardiograph; and
the physiological data streams further comprise electrocardiograph data of the person from the electrocardiograph.

65. The system of claim 52, wherein:
the physiological sensors further comprise a glucocorticoid meter; and the physiological data streams further comprise glucocorticoid data of the person from the glucocorticoid meter.

66. The system of claim 52, wherein:

the physiological sensors further comprise an electromyograph; and the physiological data streams further comprise electromyograph data of the person from the electromyograph.

67. The system of claim 52, wherein:

the physiological sensors further comprise a respiration sensor; and the data streams further comprise respiration data of the person from the respiration sensor.

68. The system of claim 52, wherein:

the physiological sensors further comprise a galvanic-skin-response sensor; and the data streams further comprise galvanic-skin-response data of the person from the galvanic-skin-response sensor.

\* \* \* \* \*